(12) United States Patent
Taylor et al.

(10) Patent No.: US 9,249,129 B2
(45) Date of Patent: Feb. 2, 2016

(54) MORPHOLINO SUBSTITUTED UREA DERIVATIVES AS MTOR INHIBITORS

(75) Inventors: Jessica Taylor, Dorking (GB); Daniel Paul Hardy, Baldock (GB); Rosemary Lynch, Cambridge (GB); Helen Sarah Niblock, Kidlington (GB); Andrew David Cansfield, Harston (GB)

(73) Assignee: CELLZOME LIMITED, Cambridge (GB)

( * ) Notice: Subject to any disclaimer, the term of this patent is extended or adjusted under 35 U.S.C. 154(b) by 325 days.

(21) Appl. No.: 13/582,429

(22) PCT Filed: Mar. 4, 2011

(86) PCT No.: PCT/EP2011/053286
§ 371 (c)(1),
(2), (4) Date: Jan. 14, 2013

(87) PCT Pub. No.: WO2011/107585
PCT Pub. Date: Sep. 9, 2011

(65) Prior Publication Data
US 2013/0196982 A1    Aug. 1, 2013

Related U.S. Application Data

(60) Provisional application No. 61/416,386, filed on Nov. 23, 2010.

(30) Foreign Application Priority Data

Mar. 4, 2010 (EP) .................................. 10155483

(51) Int. Cl.
| | |
|---|---|
| A61K 31/5377 | (2006.01) |
| C07D 413/14 | (2006.01) |
| C07D 239/42 | (2006.01) |
| C07D 401/04 | (2006.01) |
| C07D 413/04 | (2006.01) |
| C07D 498/08 | (2006.01) |

(52) U.S. Cl.
CPC .......... *C07D 413/14* (2013.01); *A61K 31/5377* (2013.01); *C07D 239/42* (2013.01); *C07D 401/04* (2013.01); *C07D 413/04* (2013.01); *C07D 498/08* (2013.01)

(58) Field of Classification Search
CPC ......................... A61K 31/5377; C07D 413/14
USPC ........................................ 514/235.8; 544/122
See application file for complete search history.

(56) References Cited

U.S. PATENT DOCUMENTS

| | | | |
|---|---|---|---|
| 8,163,763 | B2 | 4/2012 | Bergeron et al. |
| 8,785,457 | B2 | 7/2014 | Lynch et al. |
| 2004/0191836 | A1 | 9/2004 | Abraham |
| 2014/0163023 | A1 | 6/2014 | Lynch et al. |
| 2014/0288066 | A1 | 9/2014 | Lynch et al. |
| 2014/0296234 | A1 | 10/2014 | Lynch et al. |
| 2014/0378438 | A1 | 12/2014 | Lynch et al. |

FOREIGN PATENT DOCUMENTS

| | | |
|---|---|---|
| EP | 1 054 004 A1 | 11/2000 |
| WO | 9835985 | 8/1998 |
| WO | 9902166 | 1/1999 |
| WO | WO 99/02166 A1 | 1/1999 |
| WO | 0047212 | 8/2000 |
| WO | 0132651 | 5/2001 |
| WO | 0160814 | 8/2001 |
| WO | WO 2006/117560 A1 | 11/2006 |
| WO | 2006134056 | 12/2006 |
| WO | 2008015013 | 2/2008 |
| WO | 2008023159 | 2/2008 |
| WO | WO 2008/023159 A1 | 2/2008 |
| WO | 2008115974 | 9/2008 |

(Continued)

OTHER PUBLICATIONS

Fura, A. DDT, 2006, 11, pp. 133-142.*
Anari et al. DDT, 2005, 10, pp. 711-717.*
Nedderman, A. N. R. Biopharm. Drug Dispos. 2009, 30, pp. 152-162.*
Tsang, et al., "Targeting mammalian target of rapamycin (mTOR) for health and diseases", Drug Discovery Today, 2007, 12: 112-124.
Schmelzle, et al., "TOR, a central controller of cell growth", Cell, 2000, 103: 253-262.
Sarbassov, et al., "Prolonged rapamycin treatment inhibits mTORC2 assembly and Akt/PKB", Molecular Cell, 2006, 22: 159-168.
Faivre, et al., "Current development of mTOR inhibitors as anticancer agents", Nat. Rev. Drug. Discov., 2006, 5(8): 671-688.
Thoreen, et al., "An ATP-competitive Mammalian Target of Rapamycin Inhibitor Reveals Rapamycin-resistant Funtions of mTORC1", J. Biol. Chem., 2009, 284(12): 8023-32.

(Continued)

*Primary Examiner* — Rebecca Anderson
(74) *Attorney, Agent, or Firm* — Margaret M. Tomaska; Edward R. Gimmi

(57) ABSTRACT

The invention relates to compounds of formula (I)

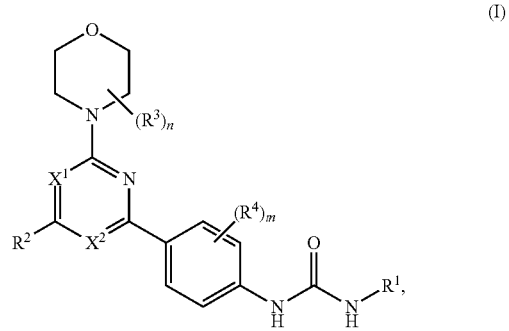

wherein $X^1$, $X^2$, $R^1$ to $R^4$, m, and n have the meaning as cited in the description and the claims. The compounds are useful as inhibitors of mTOR for the treatment or prophylaxis of mTOR related diseases and disorders. The invention also relates to pharmaceutical compositions including the compounds, the preparation of such compounds as well as the use as medicaments.

21 Claims, No Drawings

(56) References Cited

FOREIGN PATENT DOCUMENTS

| WO | 2008116129 | 9/2008 |
|---|---|---|
| WO | WO 2008/129380 A1 | 10/2008 |
| WO | 2009007748 | 1/2009 |
| WO | 2009007749 | 1/2009 |
| WO | 2009007750 | 1/2009 |
| WO | 2009007751 | 1/2009 |
| WO | 2009008992 | 1/2009 |
| WO | WO 2009/007751 A2 | 1/2009 |
| WO | 2009049242 | 4/2009 |
| WO | 2009098021 | 8/2009 |
| WO | WO 2010/014939 A1 | 2/2010 |
| WO | WO 2010/052569 A2 | 5/2010 |
| WO | 2010103094 | 9/2010 |
| WO | WO 2010/103094 A1 | 9/2010 |
| WO | 2010120994 | 10/2010 |
| WO | 2010120998 | 10/2010 |
| WO | WO 2010/120994 A2 | 10/2010 |
| WO | 2011011716 | 1/2011 |
| WO | WO 2011/011716 A1 | 1/2011 |
| WO | WO 2012/136622 A1 | 10/2012 |
| WO | WO 2013/041652 A1 | 3/2013 |
| WO | WO 2013/050508 A1 | 4/2013 |

OTHER PUBLICATIONS

Feldman, et al., "Active-site inhibitors of mTOR target Rapamycin-resistant outputs of mTORC1 andmTORC2", PLOS Biology, 2009, 7(2): e38.

Richard, et al., "Recent advances in the development of selective, ATP-competitive inhibitors of mTOR", Current Opinion Drug Discovery & Development, 2011, 13(4): 428-440.

Knight, et al., "Isoform-specific phosphoinositide 3-kinase inhibitors from an arylmorpholine scaffold", Bioorganic and Medicinal Chemistry, 2004, 12: 4749-4759.

Firestein, "Evolving concepts of rheumatoid arthritis", Nature, 2003, 423: 356-361.

Asakura, et al., "Recent advances in basic and clinical aspects of inflammatory bowel disease: which steps in the mucosal inflammation should we block for the treatment of inflammatory bowel disease?", World J Gastroenterol, 2007,13(15): 2145-9.

Schon, et al., "Psoriasis", New Engl. J. Med., 2005, 352: 1899-1912.

D'Cruz, et al., "Systemic lupus erthematosus", Lancet, 2007, 369(9561): 587-596.

Hemmer, et al., "New concepts in the immunopathogenesis of multiple sclerosis", Nat. Rev. Neuroscience, 2002, 3: 291-301.

Hanahan, et al., "The Hallmarks of Cancer", Cell, 2000, 100: 57-70.

Garcia-Echeverria, et al., "Drug discovery approaches targeting the PI3K/Akt pathway in cancer", Oncogene, 2008, 27: 5511-5526.

Sato, et al., "Single amino-acid changes that confer constitutive activation of mTOR are discovered in human cancer", Oncogene, 2010, 29(18): 2746-2752.

Xue, et al., "Palomid 529, a novel small-molecule drug, is a TORC1/TORC2 inhibitor that reduces tumor growth, tumor angiogenesis, and vascular permeability", Cancer Research, 2008, 68(22): 9551-9557.

Rosner, et al., "The mTOR pathway and its role in human genetic diseases", Mutation Research, 2008, 659(3) 284-292.

Serruys, et al., "Coronary-artery stents", N. Engl. J. Med, 2006, 354(5): 483-95.

Shah, et al., "Inappropriate activation of the TSC/Rheb/mTOR/S6K cassette induces IRS1/2 depletion, insulin resistance and cell survival deficiencies", Curr. Biol, 2004, 14(18): 1650-1656.

Yeh, et al., "Rapamycin inhibits clonal expansion and adipogenic differentiation of 3T3-L1 cells", PNAS USA, 1995,92(24): 11086-90.

Ravikumar, et al., "Inhibition of mTOR inducces autophagy and reduces toxicity of polyglutamine expansions in fly and mouse models of Huntinton disease", Nat Genet., 2004, 36(6): 585-95.

Berger, et al., "Rapamycin alleviates toxicity of different aggregate-prone proteins", Hum. Mol Genet., 2006, 15(3): 433-42.

Pan, et al., "Neuroprotection of rapamycin in lactacystin-induced neurodegeneration via autophagy enhancement", Neurobiol. Dis., 2008, 32(1): 16-25.

Mizushima, et al., "Autophagy fights disease through cellular self-digestion", Nature, 2008, 451(7182): 1069-75.

Moorman, et al., "Rapamycin-resistant mTORC1 kinase activity is required for herpesvirus replication", J. Virol., 2010, 84(10): 5260-9.

Bantscheff, et al., "Quantitative chemical proteomics reveals mechanisms of action of clinical ABL kinase inhibitors", Nat Biotechnol., 2007, 25(9): 1035-1044.

Manning, et al., "The protein kinase complement of the human genome", Science, 2002, 298(5600): 1912-1934.

Kersey, et al., "The International Protein Index: an integrated database for proteomics", Proteomics, 2004, 4(7): 1985-1988.

Anari, et al., "Bridging cheminformatic metabolite prediction and tanden mass spectrometry" , DDT, vol. 10, pp. 711-717 (2005).

Custer, et al., "The Role of Genetic Toxicology in Drug Discovery and Optimization", Current Drug Metabolosim, vol. 9, pp. 978-985 (2008).

Folkes, et al., "The identification of 2-81H-Indazol-4-yl)-6-(4-methanesulfonyl-p iperazin-1-ylmethyl)-4-morpholin-4-yl-thieno[3,2-d]pyrimidine (GDC-0941) as a potent, selective, orally bioavailable inhibitor of Class I PI3 Kinase for the treatment of cancer", Journal of Medicinal Chemistry, vol. 51, pp. 5522-5532 (2008).

Fura, A., "Role of pharmacologically active metabolites in drug discovery and development", DDT, vol. 11, pp. 133-142 (2006).

Knight, Za, et al., "Isoform-specific phosphoninositide 3-kinase inhibitors from an arylmorpholine scaffold", Bioorganic & Medicinal Chemistry, vol. 12, pp. 4749-4759 (2004).

Mizushima, N., et al., "Autophagy fights disease through cellular self-digestion," Nature, vol. 451, pp. 1069-1075 (2008).

Mortelmans, et al., "The Ames Salmonella/microsome mutagenicity assay", Mutation Research, vol. 455, pp. 29-60 (2000).

Nedderman, A. N. R., "Metabolites in Safety Testing: Metabolite Identification Strategies in Discovery and Development", Biopharm. Drug Dispos., vol. 30, pp. 153-162 (2009).

Podlipnik, et al., "DFG-in and DFG-out homology models of TrkB kinase receptor: Induced-fit and ensemble docking", Journal of Molecular Graphics and Modelling, vol. 29, pp. 309-320 (2010).

Ravikumar, et al , "Inhibition of mTOR induces autophagy and reduces toxicity of polyglutamine expansions in fly and mouse models of Huntington disease," Nature Genetics, vol. 36, No. 6, pp. 585-95 (2004).

Thoreen, et al., "An ATP-competitive Mammalian Target of Rapamycin Inhibitor Reveals Rapamycin-resistant Functions of mTORC1", Journal of Biological Chemistry, vol. 284, No. 12, pp. 8023-8032 (2009).

Verheijen, et al., "Discovery of 2-arylthieno[3,2-d]pyrimidines containing 8-oxa-3-azabicyclo[3.2.1]octane in the 4-position as potent inhibitors of mTOR with selectivity over PI3K", Bioorganic & Medicinal Chemistry Letters, vol. 20, No. 1, pp. 375-379 (2010).

\* cited by examiner

MORPHOLINO SUBSTITUTED UREA DERIVATIVES AS MTOR INHIBITORS

CROSS REFERENCE TO RELATED APPLICATIONS

The present application is a National Stage Application claiming the priority of co-pending PCT Application No. PCT/EP2011/053286 filed Mar. 4, 2001, which in turn claims priority from European Patent Application No. 10155483.0 filed Mar. 4, 2010, and U.S. Provisional Application No. 61/416,386, filed Nov. 23, 2010. Applicants claim the benefits of 35 U.S.C. §120 as to the PCT application and priority under 35 U.S.C. §119 as to the said European Patent application and the U.S. Provisional Application.

The present invention relates to a novel class of kinase inhibitors, including pharmaceutically acceptable salts, prodrugs and metabolites thereof, which are useful for modulating protein kinase activity for modulating cellular activities such as signal transduction, proliferation, and cytokine secretion. More specifically the invention provides compounds which inhibit, regulate and/or modulate kinase activity, in particular mTOR activity, and signal transduction pathways relating to cellular activities as mentioned above. Furthermore, the present invention relates to pharmaceutical compositions comprising said compounds, e.g. for the treatment of diseases such as immunological, inflammatory, autoimmune, allergic disorders, or proliferative diseases such as cancer and processes for preparing said compounds.

Kinases catalyze the phosphorylation of proteins, lipids, sugars, nucleosides and other cellular metabolites and play key roles in all aspects of eukaryotic cell physiology. Especially, protein kinases and lipid kinases participate in the signaling events which control the activation, growth, differentiation and survival of cells in response to extracellular mediators or stimuli such as growth factors, cytokines or chemokines. In general, protein kinases are classified in two groups, those that preferentially phosphorylate tyrosine residues and those that preferentially phosphorylate serine and/or threonine residues.

Inappropriately high protein kinase activity is involved in many diseases including cancer, metabolic diseases and autoimmune/inflammatory disorders. This can be caused either directly or indirectly by the failure of control mechanisms due to mutation, overexpression or inappropriate activation of the enzyme. In all of these instances, selective inhibition of the kinase is expected to have a beneficial effect.

mTOR ("mammalian target of rapamycin", also known as FRAP or RAFT1) has become a recent focus of drug discovery efforts (Tsang et al., 2007, Drug Discovery Today 12, 112-124). It was discovered that the mTOR protein is the drug target for the immunosuppressive effect of rapamycin, a drug that is used to prevent transplant rejection. Rapamycin works through a gain-of-function mechanism by binding to the intracellular protein "FK-506-binding protein of 12 kDA" (FKBP12) to generate a drug-receptor complex that then binds to and inhibits mTOR. Thus, rapamycin induces the formation of the ternary complex consisting of rapamycin and the two proteins FKBP12 and mTOR.

The mTOR protein is a large kinase of 289 kDA which occurs in all eukaryotic organisms sequenced so far (Schmelzle and Hall, 2000, Cell 103, 253-262). The sequence of the carboxy-terminal "phosphatidylinositol 3-kinase (PI3K)-related kinase" (PIKK) domain is highly conserved between species and exhibits serine and threonine kinase activity but no detectable lipid kinase activity. The intact PIKK domain is required for all known functions of mTOR.

The FKBP12-rapamycin-binding (FRB) domain is located close to the PIKK domain and forms a hydrophobic pocket that binds to the rapamycin bound to FKBP12. The FRB domain does not appear to inhibit the enzymatic activity of the kinase domain directly. One explanation is that FKBP12-rapamycin prevents the interaction of mTOR with its substrates due to steric hindrance. The N-terminus of mTOR consists of approximately 20 tandem repeats of 37 to 43 amino acids termed HEAT repeats. The HEAT repeats interact with protein binding partners such as Raptor.

mTOR can form at least two distinct proteins complexes, mTORC1 and mTORC2. In the mTORC1 protein complex mTOR interacts with the proteins Raptor and mLST8/GβL and regulates cell growth by phosphorylating effectors such as p70S6K and 4E-BP1 to promote mRNA translation and protein synthesis. The mTORC1 complex is responsible for sensing nutrient signals (for example the availability of amino acids) in conjunction with insulin signaling. The activity of mTOR in mTORC1 can be inhibited by rapamycin.

The second protein complex, mTORC2, consists of the proteins mTOR, Rictor, mLST8/GβL and Sin 1 and is involved in the organization of actin. The mTORC2 was originally described as rapamycin insensitive. A recent publication demonstrated that rapamycin affects the function of mTORC2 after prolonged treatment through an indirect mechanism by interfering with the assembly of the mTORC2 protein complex (Sarbassov et al., 2006, Molecular Cell 22, 159-168).

The biological function of mTOR is that of a central regulator of various extracellular and intracellular signals, including growth factors, nutrients, energy and stress. Growth factor and hormone (e.g. insulin) induced mTOR activation is mediated by PI3 kinases, Akt, and the tuberous sclerosis protein complex (TSC). For example, mTOR acts as a central regulator of cell proliferation, angiogenesis, and cell metabolism (Tsang et al., 2007, Drug Discovery Today 12, 112-124). In addition to its immunosuppressive effects rapamycin (Sirolimus) is a potent inhibitor of the proliferation of vascular smooth muscle cells and was approved by the FDA as an anti-restenosis drug used in coronary stents. In addition, it was observed that rapamycin displays anti-tumour activity in several in vitro and animal models (Faivre et al., 2006. Nat. Rev. Drug. Discov. 5(8):671-688).

Because of the therapeutic potential of rapamycin several pharmaceutical companies started to develop rapamycin analogs to improve the pharmacokinetic properties of the molecule (Tsang et al., 2007, Drug Discovery Today 12, 112-124). For example, CCI779 (temsirolimus) represents a more water-soluble ester derivative of rapamycin for intravenous and oral formulation. CCI779 has antitumor activity either alone or in combination with cytotoxic agents in cell lines. RAD001 (everolimus) is a hydroxyethyl ether derivative of rapamycin that is developed for oral administration. AP23573 (deferolimus) is developed for either oral or intravenous administration.

In general, the rapamycin derivatives act through the same molecular mechanism, the induction of the ternary rapamycin-FKBP12-mTOR complex. It is conceivable that the function of mTOR could be equally or even more effectively inhibited by inhibitors of the kinase function. For example, this could be achieved by identifying compounds that interact with the ATP-binding pocket of the mTOR kinase domain. For example Torin1 is a potent and selective ATP-competitive mTOR inhibitor that directly binds to both mTOR complexes and impairs cell growth and proliferation more efficiently than rapamycin (Thoreen et al., 2009. J Biol. Chem. 284(12): 8023-32; Feldman et al., 2009. PLOSBiology 7(2):e38).

Diseases and disorders associated with mTOR are further described, e.g. in WO-A 2008/116129, WO-A 2008/115974, WO-A 2008/023159, WO-A 2009/007748, WO-A 2009/007749, WO-A 2009/007750, WO-A 2009/007751, WO-A 2011/011716.

Several mTOR inhibitors have been reported in the literature which may be useful in the medical field, for example as anticancer agents (Faivre et al., 2006. Nat. Rev. Drug. Discov. 5(8):671-688). In WO-A 2008/116129 imidazolopyrimidine analogs are described as mixed mTOR and PI3K kinase inhibitors. Pyrazolopyrimidine analogs are described as mixed mTOR and PI3K kinase inhibitors in WO-A 2008/115974. Further pyrimidine derivatives as mTOR kinase and/or PI3K enzyme active compounds are disclosed in WO-A 2008/023159, WO-A 2009/007748, WO-A 2009/007749, WO-A 2009/007750, WO-A 2009/007751, WO-A 2010/103094, WO-A 2010/120994 and WO-A 2010/120998.

It is expected that a selective mTOR inhibitor that inhibits mTOR with greater potency than other kinases may have advantageous therapeutic properties because inhibition of other kinases may cause unwanted side effects (Richard et al., 2011. Current Opinion Drug Discovery and Development 13(4):428-440). Especially selectivity versus members of the phosphatidylinositol 3 kinase (PI3K) family (for example PI3Kα, PI3Kβ, PI3Kγ, and PI3Kδ) and PI3K related kinases (for example DMA-PK, ATM and ATR) may be important.

Even though mTOR inhibitors are known in the art there is a need for providing additional mTOR inhibitors having at least partially more effective pharmaceutically relevant properties, like activity, selectivity, and ADME properties.

Accordingly, the present invention provides compounds of formula (I)

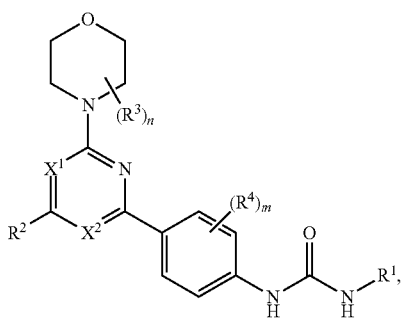

(I)

or a pharmaceutically acceptable salt, prodrug or metabolite thereof, wherein $R^1$ is H; $T^1$; or $C_{1-6}$ alkyl; wherein $C_{1-6}$ alkyl is optionally substituted with one or more $R^5$, which are the same or different;

$R^5$ is halogen; CN; $OR^6$; $C(O)N(R^6R^{6a})$; $N(R^{6a})C(O)R^6$; or $N(R^6R^{6a})$;

$T^1$ is phenyl; 4 to 7 membered heterocyclyl; or $C_{3-7}$ cycloalkyl, wherein $T^1$ is optionally substituted with one or more $R^{5a}$, which are the same or different;

$R^{5a}$ is halogen; CN; $OR^6$; $N(R^6R^{6a})$; or $C_{1-6}$ alkyl, wherein $C_{1-6}$ alkyl is optionally substituted with one or more $R^{5b}$, which are the same or different;

$R^{5b}$ is halogen; or $OR^6$;

$R^6$, $R^{6a}$ are independently selected from the group consisting of H; and $C_{1-6}$ alkyl, wherein $C_{1-6}$ alkyl is optionally substituted with one or more halogen, which are the same or different;

$R^2$ is H; or $T^2$;

$T^2$ is phenyl or 5 to 6 membered aromatic heterocyclyl, wherein $T^2$ is optionally substituted with 1, 2 or 3 $R^7$, which are the same or different;

$R^7$ is halogen; CN; $OR^8$; $CO(O)R^8$; $C(O)N(R^8R^{8a})$; $S(O)_2N(R^8R^{8a})$; $S(O)N(R^8R^{8a})$; $S(O)_2R^8$; $S(O)R^8$; $N(R^8R^{8a})$; $N(R^8)C(O)R^{8a}$; $N(R^8)S(O)_2R^{8a}$; $N(R^8)S(O)R^{8a}$; $N(R^8)C(O)N(R^{8a}R^{8b})$; $N(R^8)C(O)OR^{8a}$; $OC(O)N(R^8R^{8a})$; or $C_{1-6}$ alkyl; wherein $C_{1-6}$ alkyl is optionally substituted with one or more $R^9$, which are the same or different;

$R^8$, $R^{8a}$, $R^{8b}$ are independently selected from the group consisting of H; $C_{1-6}$ alkyl; and 5 to 6 membered heterocyclyl, wherein $C_{1-6}$ alkyl is optionally substituted with one or more $R^9$, which are the same or different and wherein 5 to 6 membered heterocyclyl is optionally substituted with one or more $R^{9a}$, which are the same or different;

$R^9$ is halogen; CN; $C(O)OR^{10}$; $OR^{10}$; $C(O)R^{10}$; $C(O)N(R^{10}R^{10a})$; $S(O)_2N(R^{10}R^{10a})$; $S(O)N(R^{10}R^{10a})$; $S(O)_2R^{10}$; $N(R^{10}R^{10a})$; $OC(O)R^{10}$; $N(R^{10})C(O)R^{10a}$; $N(R^{10})S(O)_2R^{10a}$; $N(R^{10})S(O)R^{10a}$; $N(R^{10})C(O)N(R^{10a}R^{10b})$; $N(R^{10})C(O)OR^{10a}$; $OC(O)N(R^{10}R^{10a})$; or 5 to 6 membered heterocyclyl, wherein 5 to 6 membered heterocyclyl is optionally substituted with one or more $R^{11}$, which are the same or different;

$R^{9a}$ is halogen; CN; $C(O)OR^{10}$; $OR^{10}$; oxo ($=$O), where the ring is at least partially saturated; $C(O)R^{10}$; $C(O)N(R^{10}R^{10a})$; $S(O)_2N(R^{10}R^{10a})$; $S(O)N(R^{10}R^{10a})$; $S(O)_2R^{10}$; $N(R^{10}R^{10a})$; $NO_2$; $OC(O)R^{10}$; $N(R^{10})C(O)R^{10a}$; $N(R^{10})S(O)_2R^{10a}$; $N(R^{10})S(O)R^{10a}$; $N(R^{10})C(O)N(R^{10a}R^{10b})$; $N(R^{10})C(O)OR^{10a}$; $OC(O)N(R^{10}R^{10a})$; or $C_{1-6}$ alkyl, wherein $C_{1-6}$ alkyl is optionally substituted with one or more $R^{11a}$, which are the same or different;

$R^{10}$, $R^{10a}$, $R^{10b}$ are independently selected from the group consisting of H; and $C_{1-6}$ alkyl, wherein $C_{1-6}$ alkyl is optionally substituted with one or more halogen, which are the same or different;

$R^{11}$, $R^{11a}$ are independently selected from the group consisting of halogen; and $C_{1-6}$ alkyl, wherein $C_{1-6}$ alkyl is optionally substituted with one or more halogen, which are the same or different;

Each $R^3$ is independently $C_{1-6}$ alkyl, wherein $R^3$ is optionally substituted with one or more halogen, which are the same or different;

Optionally two $R^3$ are joined together with the atoms to which they are attached to form a ring $T^3$;

$T^3$ is $C_{3-7}$ cycloalkyl; 4 to 7 membered heterocyclyl; or phenyl, wherein $T^3$ is optionally substituted with one or more $C_{1-6}$ alkyl, which are the same or different and optionally substituted with one or more halogen, which are the same or different;

Each $R^4$ is independently halogen;

m is 0, 1 or 2 n is 0, 1 or 2

One of $X^1$, $X^2$ is $C(R^{12})$ and the other is N;

$R^{12}$ is H; halogen; CN; or $C_{1-6}$ alkyl, wherein $C_{1-6}$ alkyl is optionally substituted with one or more halogen, which are the same or different.

In case a variable or substituent can be selected from a group of different variants and such variable or substituent occurs more than once the respective variants can be the same or different.

Within the meaning of the present invention the terms are used as follows:

"Alkyl" means a straight-chain or branched carbon chain. Each hydrogen of an alkyl carbon may be replaced by a substituent as further specified herein.

"$C_{1-4}$ alkyl" means an alkyl chain having 1-4 carbon atoms, e.g. if present at the end of a molecule: methyl, ethyl, n-propyl, isopropyl, n-butyl, isobutyl, sec-butyl tert-butyl, or e.g. —CH$_2$—, —CH$_2$—CH$_2$—, —CH(CH$_3$)—, —C(CH$_2$)—, —CH$_2$—CH$_2$—CH$_2$—, —CH(C$_2$H$_5$)—, —C(CH$_3$)$_2$—, when two moieties of a molecule are linked by the alkyl group. Each hydrogen of a C$_{1-4}$ alkyl carbon may be replaced by a substituent as further specified herein.

"C$_{1-6}$ alkyl" means an alkyl chain having 1-6 carbon atoms, e.g. if present at the end of a molecule: C$_{1-4}$ alkyl, methyl, ethyl, n-propyl, isopropyl, n-butyl, isobutyl, sec-butyl; tert-butyl, n-pentyl, n-hexyl, or e.g. —CH$_2$—, —CH$_2$—CH$_2$—, —CH(CH$_3$)—, —CH$_2$—CH$_2$—CH$_2$—, —CH(C$_2$H$_5$)—, —C(CH$_3$)$_2$—, when two moieties of a molecule are linked by the alkyl group. Each hydrogen of a C$_{1-6}$ alkyl carbon may be replaced by a substituent as further specified herein.

"C$_{3-7}$ cycloalkyl" or "C$_{3-7}$ cycloalkyl ring" means a cyclic alkyl chain having 3-7 carbon atoms, e.g. cyclopropyl, cyclobutyl, cyclopentyl, cyclohexyl, cyclohexenyl, cycloheptyl. Each hydrogen of a cycloalkyl carbon may be replaced by a substituent as further specified herein.

"Halogen" means fluoro, chloro, bromo or iodo. It is generally preferred that halogen is fluoro or chloro.

"4 to 7 membered heterocyclyl" or "4 to 7 membered heterocycle" means a ring with 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 4 to 7 membered heterocycles are azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine or homopiperazine. The term "5 to 6 membered heterocyclyl" or "5 to 6 membered heterocycle" is defined accordingly.

"8 to 11 membered heterobicyclyl" or "8 to 11 membered heterobicycle" means a heterocyclic system of two rings with 8 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 8 to 11 membered heterobicycle are indole, indoline, benzofuran, benzothiophene, benzoxazole, benzisoxazole, benzothiazole, benzisothiazole, benzimidazole, benzimidazo line, quinoline, quinazoline, dihydroquinazoline, quinoline, dihydroquinoline, tetrahydroquinoline, decahydroquinoline, isoquino line, decahydroisoquino line, tetrahydroisoquinoline, dihydroisoquinoline, benzazepine, purine or pteridine. The term 8 to 11 membered heterobicycle also includes spiro structures of two rings like 1,4-dioxa-8-azaspiro[4.5]decane or bridged heterocycles like 8-aza-bicyclo[3.2.1]octane.

"5 to 6 membered aromatic heterocyclyl" or "5 to 6 membered aromatic heterocycle" means a heterocycle derived from cyclopentadienyl or benzene, where at least one carbon atom is replaced by a heteoatom selected from the group consisting of sulfur (including —S(O)—, —S(O)$_2$—), oxygen and nitrogen (including =N(O)—). Examples for such heterocycles are furan, thiophene, pyrrole, imidazole, pyrazole, oxazole, isoxazole, thiazole, isothiazole, thiadiazole, pyranium, pyridine, pyridazine, pyrimidine, triazole, tetrazole.

Preferred compounds of formula (I) are those compounds in which one or more of the residues contained therein have the meanings given below, with all combinations of preferred substituent definitions being a subject of the present invention. With respect to all preferred compounds of the formula (I) the present invention also includes all tautomeric and stereoisomeric forms and mixtures thereof in all ratios, and their pharmaceutically acceptable salts.

In preferred embodiments of the present invention, the substituents mentioned below independently have the following meaning. Hence, one or more of these substituents can have the preferred or more preferred meanings given below.

Preferably, R$^1$ is H; or C$_{1-6}$ alkyl, wherein C$_{1-6}$ alkyl is optionally substituted with one or more R$^5$, which are the same or different; or C$_{3-7}$ cycloalkyl, wherein C$_{3-7}$ cycloalkyl is optionally substituted with one or more R$^{5a}$, which are the same or different. More preferably, R$^1$ is H; optionally substituted C$_{1-6}$ alkyl; optionally substituted C$_{3-7}$ cycloalkyl; or optionally substituted CH$_2$—C$_{3-7}$ cycloalkyl. Also more preferably, R$^1$ is H; unsubstituted C$_{1-6}$ alkyl; or unsubstituted C$_{3-7}$ cycloalkyl. Also more preferably, R$^1$ is H; unsubstituted C$_{1-6}$ alkyl; cyclopropyl; or CH$_2$-cyclopropyl. Also more preferably, R$^1$ is H; unsubstituted C$_{1-6}$ alkyl; or cyclopropyl. Also more preferably, R$^1$ is H; cyclopropyl; methyl; ethyl; n-propyl; fluoroethyl; or hydroxyethyl. Preferably, R$^1$ is pyridine, wherein pyridine is optionally substituted with one or more R$^{5a}$, which are the same or different.

In one preferred embodiment R$^1$ is H. In another preferred embodiment R$^1$ is C$_{1-6}$ alkyl, which is unsubstituted, especially methyl, ethyl, propyl. In another preferred embodiment R$^1$ is substituted C$_{1-6}$ alkyl, especially hydroxyethyl, fluoroethyl, difluoroethyl, aminoethyl, acetamidoethyl, hydroxypropyl, hydroxybutyl, aminocarbonylmethyl. In another preferred embodiment R$^1$ is unsubstituted C$_{3-7}$ cycloalkyl, especially cyclopropyl. In another preferred embodiment R$^1$ is substituted C$_{3-7}$ cycloalkyl, especially hydroxymethylcyclobutyl, hydroxycyclopentyl, methoxycyclobutyl. In another preferred embodiment R$^1$ is pyridyl, oxetanyl.

Preferably, R$^5$ is halogen; CN; OR$^6$; C(O)N(R$^6$R$^{6a}$); or N(R$^6$R$^{6a}$).

Preferably, R$^{5a}$ is halogen; CN; OR$^6$; N(R$^6$R$^{6a}$); or C$_{1-6}$ alkyl, wherein C$_{1-6}$ alkyl is optionally substituted with one or more halogen, which are the same or different;

Preferably, R$^2$ is T$^2$. In one preferred embodiment T$^2$ is unsubstituted. In another preferred embodiment T$^2$ is substituted.

Preferably, T$^2$ (more preferably, phenyl; pyridyl; or pyrazolyl, even more preferably, phenyl) is unsubstituted or substituted with 1 or 2 R$^7$, which are the same or different.

Preferably, R$^7$ is halogen; CN; S(O)R$^8$; S(O)$_2$R$^8$; N(R$^8$)SO$_2$R$^{8a}$; SO$_2$N(R$^8$R$^{8a}$); N(R$^8$)C(O)R$^{8a}$; C(O)N(R$^8$R$^{8a}$); CO(O)R$^8$; or CH$_2$R$^9$. More preferably, R$^7$ is F; CN; S(O)$_2$CH$_3$; NHSO$_2$CH$_3$; NHC(O)CH$_3$; SO$_2$NHCH$_3$; SO$_2$N(CH$_3$)$_2$; C(O)NH$_2$; CO(O)H; S(O)$_2$CH$_2$CH$_3$; S(O)$_2$pyrrolidine or CH$_2$OH. Preferably, R$^7$ is halogen; CN; S(O)$_2$R$^8$; N(R$^8$)SO$_2$R$^{8a}$; SO$_2$N(R$^8$R$^{8a}$); N(R$^8$)C(O)R$^{8a}$; C(O)N(R$^8$R$^{8a}$); CO(O)R$^8$; or CH$_2$R$^9$. More preferably, R$^7$ is F; CN; S(O)$_2$CH$_3$; NHSO$_2$CH$_3$; NHC(O)CH$_3$; SO$_2$NHCH$_3$; SO$_2$N(CH$_3$)$_2$; C(O)NH$_2$; CO(O)H; or CH$_2$OH. More preferably, R$^7$ is S(O)$_2$R$^9$.

Preferably, R$^2$ is H.

Preferably, $T^3$ is $C_{3-7}$ cycloalkyl; or 4 to 7 membered heterocyclyl, wherein $T^3$ is optionally substituted with one or more $C_{1-6}$ alkyl, which are the same or different and optionally substituted with one or more halogen, which are the same or different.

Preferably, $R^3$ is methyl. More preferably, $R^3$ is ortho to the ring nitrogen of the morpholino ring. Preferably, n is 0; n is 1 and $R^3$ is methyl; or n is 2 and the two $R^3$ are joined together with the morpholine ring to form an 8-oxa-3-azabicyclo[3.2.1]octan-3-yl ring. Even more preferably, $R^3$ is selected to give formula (Ia) or (Ib)

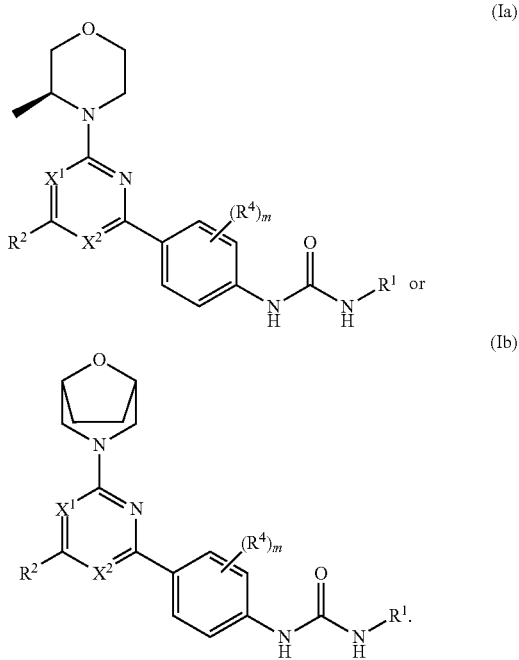

More preferably, $R^3$ is selected to give formula (Ia).

Preferably, $R^4$ is F.

Preferably, m, n are independently selected from the group consisting of 0; and 1. Preferably, m is 0; or 1. Preferably, n is 0; or 1, more preferably 1. Also preferably n, $R^3$ in formula (I) are selected to give formula (Ib).

Preferably, $R^5$ is halogen; CN; $OR^6$; or $N(R^6R^{6a})$.

Preferably, $X^1$ is N. In another preferred embodiment $X^2$ is N.

Preferably, $R^{12}$ is H.

Compounds of formula (I) in which some or all of the above-mentioned groups have the preferred meanings are also an object of the present invention.

Further preferred compounds of the present invention are selected from the group consisting of 1-cyclopropyl-3-(4-(2-morpholino-6-(pyridin-3-yl)pyrimidin-4-yl)phenyl)urea;

(S)-1-ethyl-3-(4-(6-(5-fluoro-2-(methylsulfonyl)phenyl)-2-(3-methylmorpholino)pyrimidin-4-yl)phenyl)urea;

(S)-1-cyclopropyl-3-(4-(4-(3-methylmorpholino)-6-(pyridin-3-yl)pyrimidin-2-yl)phenyl)urea;

(S)-1-cyclopropyl-3-(4-(2-(3-methylmorpholino)-6-(2-(methylsulfonyl)phenyl)pyrimidin-4-yl)phenyl)urea;

(S)-1-cyclopropyl-3-(4-(6-(3-methylmorpholino)-2-(3-(methylsulfonyl)phenyl)pyrimidin-4-yl)phenyl)urea;

(S)-1-cyclopropyl-3-(4-(4-(3-methylmorpholino)-6-(2-(methylsulfonyl)phenyl)pyrimidin-2-yl)phenyl)urea;

(S)-1-cyclopropyl-3-(4-(2-(3-methylmorpholino)-6-(pyridin-3-yl)pyrimidin-4-yl)phenyl)urea;

(S)-1-(4-(6-(2-cyanophenyl)-2-(3-methylmorpholino)pyrimidin-4-yl)phenyl)-3-ethylurea;

(S)—N-(2-(6-(4-(3-ethylureido)phenyl)-2-(3-methylmorpholino)pyrimidin-4-yl)phenyl)methanesulfonamide;

(S)—N-(2-(6-(4-(3-ethylureido)phenyl)-2-(3-methylmorpholino)pyrimidin-4-yl)phenyl)acetamide;

(S)-2-(6-(4-(3-ethylureido)phenyl)-2-(3-methylmorpholino)pyrimidin-4-yl)benzoic acid;

(S)-2-(6-(4-(3-ethylureido)phenyl)-2-(3-methylmorpholino)pyrimidin-4-yl)benzamide;

(S)-1-ethyl-3-(4-(2-(3-methylmorpholino)-6-(pyridin-4-yl)pyrimidin-4-yl)phenyl)urea;

(S)-2-(6-(4-(3-ethylureido)phenyl)-2-(3-methylmorpholino)pyrimidin-4-yl)-N,N-dimethylbenzenesulfonamide;

(S)-1-ethyl-3-(4-(2-(3-methylmorpholino)-6-(5-(methylsulfonyl)pyridin-3-yl)pyrimidin-4-yl)phenyl)urea;

(S)-1-ethyl-3-(4-(6-(2-(hydroxymethyl)phenyl)-2-(3-methylmorpholino)pyrimidin-4-yl)phenyl)urea;

(S)-1-ethyl-3-(4-(6-(3-methylmorpholino)-2-phenylpyrimidin-4-yl)phenyl)urea;

(S)-1-ethyl-3-(4-(2-(3-methylmorpholino)-6-(1H-pyrazol-3-yl)pyrimidin-4-yl)phenyl)urea;

2-(6-(4-(3-ethylureido)phenyl)-2-morpholinopyrimidin-4-yl)-N-methylbenzenesulfonamide;

1-ethyl-3-(4-(6-(2-(methylsulfonyl)phenyl)-2-morpholinopyrimidin-4-yl)phenyl)urea;

(S)-1-cyclopropyl-3-(4-(2-(6-fluoropyridin-3-yl)-6-(3-methylmorpholino)pyrimidin-4-yl)phenyl)urea;

(S)-1-cyclopropyl-3-(4-(6-(3-methylmorpholino)-2-(5-(methylsulfonyl)pyridin-3-yl)pyrimidin-4-yl)phenyl)urea;

(S)-1-cyclopropyl-3-(4-(2-(5-fluoropyridin-3-yl)-6-(3-methylmorpholino)pyrimidin-4-yl)phenyl)urea;

(S)-1-cyclopropyl-3-(4-(2-(3-fluoropyridin-4-yl)-6-(3-methylmorpholino)pyrimidin-4-yl)phenyl)urea;

(S)-1-cyclopropyl-3-(4-(4-(3-methylmorpholino)-6-(pyridin-4-yl)pyrimidin-2-yl)phenyl)urea;

1-cyclopropyl-3-(4-(4-morpholinopyrimidin-2-yl)phenyl)urea;

1-methyl-3-(4-(4-morpholinopyrimidin-2-yl)phenyl)urea;

1-cyclopropyl-3-(4-(2-morpholinopyrimidin-4-yl)phenyl)urea;

1-ethyl-3-(4-(2-morpholinopyrimidin-4-yl)phenyl)urea;

1-methyl-3-(4-(2-morpholinopyrimidin-4-yl)phenyl)urea;

1-(4-(2-morpholinopyrimidin-4-yl)phenyl)-3-propylurea;

1-(4-(4-morpholinopyrimidin-2-yl)phenyl)-3-propylurea;

1-(4-(4-morpholinopyrimidin-2-yl)phenyl)urea;

(S)-1-methyl-3-(4-(4-(3-methylmorpholino)pyrimidin-2-yl)phenyl)urea;

(S)-1-cyclopropyl-3-(4-(4-(3-methylmorpholino)pyrimidin-2-yl)phenyl)urea;

1-ethyl-3-(4-(4-morpholinopyrimidin-2-yl)phenyl)urea;

(S)-1-ethyl-3-(4-(4-(3-methylmorpholino)pyrimidin-2-yl)phenyl)urea;

(S)-1-ethyl-3-(4-(2-(3-methylmorpholino)pyrimidin-4-yl)phenyl)urea;

(S)-1-cyclopropyl-3-(4-(2-(3-methylmorpholino)pyrimidin-4-yl)phenyl)urea;

(S)-1-cyclopropyl-3-(4-(6-(5-fluoro-2-(methylsulfonyl)phenyl)-2-(3-methylmorpholino)pyrimidin-4-yl)phenyl)urea;

(S)-1-(4-(6-(5-fluoro-2-(methylsulfonyl)phenyl)-2-(3-methylmorpholino)pyrimidin-4-yl)phenyl)-3-(2-hydroxyethyl)urea;

(S)-1-cyclopropyl-3-(4-(4-(3-methylmorpholino)-6-(pyridin-2-yl)pyrimidin-2-yl)phenyl)urea;
(S)-1-(2-hydroxyethyl)-3-(4-(4-(3-methylmorpholino)-6-(pyridin-2-yl)pyrimidin-2-yl)phenyl)urea;
(S)-1-(4-(6-(5-fluoro-2-(methylsulfonyl)phenyl)-2-(3-methylmorpholino)pyrimidin-4-yl)phenyl)-3-(2-fluoroethyl)urea;
1-cyclopropyl-3-(4-(2-((S)-3-methylmorpholino)-6-(2-(methylsulfinyl)pyridin-3-yl)pyrimidin-4-yl)phenyl)urea;
(S)-1-cyclopropyl-3-(4-(2-(3-methylmorpholino)-6-(2-(methylsulfonyl)pyridin-3-yl)pyrimidin-4-yl)phenyl)urea;
(S)-1-(2,2-difluoroethyl)-3-(4-(6-(5-fluoro-2-(methylsulfonyl)phenyl)-2-(3-methylmorpholino)pyrimidin-4-yl)phenyl)urea;
1-(4-(4-(8-oxa-3-azabicyclo[3.2.1]octan-3-yl)pyrimidin-2-yl)phenyl)-3-cyclopropylurea;
1-(4-(4-(8-oxa-3-azabicyclo[3.2.1]octan-3-yl)pyrimidin-2-yl)phenyl)-3-ethylurea;
1-(4-(4-(8-oxa-3-azabicyclo[3.2.1]octan-3-yl)pyrimidin-2-yl)phenyl)-3-(2-hydroxyethyl)urea;
1-(4-(4-(8-oxa-3-azabicyclo[3.2.1]octan-3-yl)pyrimidin-2-yl)phenyl)-3-(2,2-difluoroethyl)urea;
1-(4-(4-(8-oxa-3-azabicyclo[3.2.1]octan-3-yl)pyrimidin-2-yl)phenyl)-3-(2-fluoroethyl)urea;
(S)-1-(2-hydroxyethyl)-3-(4-(4-(3-methylmorpholino)pyrimidin-2-yl)phenyl)urea;
(S)-1-(2,2-difluoroethyl)-3-(4-(4-(3-methylmorpholino)pyrimidin-2-yl)phenyl)urea;
(S)-1-(2-fluoroethyl)-3-(4-(4-(3-methylmorpholino)pyrimidin-2-yl)phenyl)urea;
1-(4-(2-(8-oxa-3-azabicyclo[3.2.1]octan-3-yl)pyrimidin-4-yl)phenyl)-3-ethylurea;
1-(4-(2-(8-oxa-3-azabicyclo[3.2.1]octan-3-yl)pyrimidin-4-yl)phenyl)-3-cyclopropylurea;
(S)-1-(2-hydroxyethyl)-3-(4-(2-(3-methylmorpholino)pyrimidin-4-yl)phenyl)urea;
1-(4-(2-(8-oxa-3-azabicyclo[3.2.1]octan-3-yl)pyrimidin-4-yl)phenyl)-3-(2-hydroxyethyl)urea;
(S)-1-(4-(4-(3-methylmorpholino)pyrimidin-2-yl)phenyl)-3-(pyridin-4-yl)urea;
1-(4-(4-(8-oxa-3-azabicyclo[3.2.1]octan-3-yl)pyrimidin-2-yl)phenyl)-3-(pyridin-4-yl)urea;
1-(4-(6-(5-fluoro-2-(methylsulfonyl)phenyl)-2-morpholinopyrimidin-4-yl)phenyl)-3-(2-hydroxyethyl)urea;
(S)-1-cyclopropyl-3-(3-fluoro-4-(4-(5-fluoropyridin-3-yl)-6-(3-methylmorpholino)pyrimidin-2-yl)phenyl)urea;
(S)-1-(4-(6-(5-fluoro-2-(methylsulfonyl)phenyl)-2-(3-methylmorpholino)pyrimidin-4-yl)phenyl)-3-(3-hydroxypropyl)urea;
(S)-1-(3-fluoro-4-(4-(5-fluoropyridin-3-yl)-6-(3-methylmorpholino)pyrimidin-2-yl)phenyl)-3-(2-hydroxyethyl)urea;
(S)-1-cyclopropyl-3-(3-fluoro-4-(4-(5-fluoro-2-(methylsulfonyl)phenyl)-6-(3-methylmorpholino)pyrimidin-2-yl)phenyl)urea;
(S)-1-(3-fluoro-4-(4-(5-fluoropyridin-3-yl)-6-(3-methylmorpholino)pyrimidin-2-yl)phenyl)-3-(2-fluoroethyl)urea;
(S)-1-(3-fluoro-4-(4-(5-fluoro-2-(methylsulfonyl)phenyl)-6-(3-methylmorpholino)pyrimidin-2-yl)phenyl)-3-(2-fluoroethyl)urea;
(S)-1-(4-(6-(5-fluoro-2-(methylsulfonyl)phenyl)-2-(3-methylmorpholino)pyrimidin-4-yl)phenyl)-3-(1-hydroxy-2-methylpropan-2-yl)urea;
(S)-2-(3-(4-(6-(5-fluoro-2-(methylsulfonyl)phenyl)-2-(3-methylmorpholino)pyrimidin-4-yl)phenyl)ureido)acetamide;
1-(4-(6-(5-fluoro-2-(methylsulfonyl)phenyl)-2-((S)-3-methylmorpholino)pyrimidin-4-yl)phenyl)-3-(2-hydroxypropyl)urea;
(S)-1-(3-fluoro-4-(4-(5-fluoro-2-(methylsulfonyl)phenyl)-6-(3-methylmorpholino)pyrimidin-2-yl)phenyl)-3-(2-hydroxyethyl)urea;
1-(4-(6-(5-fluoro-2-(methylsulfonyl)phenyl)-2-((S)-3-methylmorpholino)pyrimidin-4-yl)phenyl)-3-((R)-1-hydroxypropan-2-yl)urea;
1-(4-(6-(5-fluoro-2-(methylsulfonyl)phenyl)-2-((S)-3-methylmorpholino)pyrimidin-4-yl)phenyl)-3-((S)-1-hydroxypropan-2-yl)urea;
(S)-1-(4-(6-(5-fluoro-2-(methylsulfonyl)phenyl)-2-(3-methylmorpholino)pyrimidin-4-yl)phenyl)-3-(1-(hydroxymethyl)cyclobutyl)urea;
1-(4-(6-(5-fluoro-2-(methylsulfonyl)phenyl)-2-((S)-3-methylmorpholino)pyrimidin-4-yl)phenyl)-3-((1S,2S)-2-hydroxycyclopentyl)urea;
(S)-1-cyclopropyl-3-(4-(4-(5-fluoro-2-(methylsulfonyl)phenyl)-6-(3-methylmorpholino)pyrimidin-2-yl)phenyl)urea;
(S)-1-(4-(4-(5-fluoro-2-(methylsulfonyl)phenyl)-6-(3-methylmorpholino)pyrimidin-2-yl)phenyl)-3-(2-hydroxyethyl)urea;
(S)-1-(4-(6-(5-fluoro-2-(methylsulfonyl)phenyl)-2-(3-methylmorpholino)pyrimidin-4-yl)phenyl)-3-(3-methoxycyclobutyl)urea;
(S)-1-(2-hydroxyethyl)-3-(4-(4-(3-methylmorpholino)-6-(2-(methylsulfonyl)phenyl)pyrimidin-2-yl)phenyl)urea;
1-(4-(2-(8-oxa-3-azabicyclo[3.2.1]octan-3-yl)-6-(5-fluoro-2-(methylsulfonyl)phenyl)pyrimidin-4-yl)phenyl)-3-cyclopropylurea;
1-(4-(6-(5-fluoro-2-(methylsulfonyl)phenyl)-2-((S)-3-methylmorpholino)pyrimidin-4-yl)phenyl)-3-((R)-2-hydroxypropyl)urea;
1-(4-(6-(5-fluoro-2-(methylsulfonyl)phenyl)-2-((S)-3-methylmorpholino)pyrimidin-4-yl)phenyl)-3-((S)-2-hydroxypropyl)urea;
(S)-1-(2-aminoethyl)-3-(4-(6-(5-fluoro-2-(methylsulfonyl)phenyl)-2-(3-methylmorpholino)pyrimidin-4-yl)phenyl)urea;
(S)—N-(2-(3-(4-(6-(5-fluoro-2-(methylsulfonyl)phenyl)-2-(3-methylmorpholino)pyrimidin-4-yl)phenyl)ureido)ethyl)acetamide;
(S)-1-(4-(6-(5-fluoro-2-(methylsulfonyl)phenyl)-2-(3-methylmorpholino)pyrimidin-4-yl)phenyl)-3-(oxetan-3-yl)urea;
(S)-1-cyclopropyl-3-(4-(6-(2-(ethylsulfonyl)phenyl)-2-(3-methylmorpholino)pyrimidin-4-yl)phenyl)urea; and
(S)-1-cyclopropyl-3-(4-(2-(3-methylmorpholino)-6-(2-(pyrrolidin-1-ylsulfonyl)phenyl)pyrimidin-4-yl)phenyl)urea.

Prodrugs of the compounds of the present invention are also within the scope of the present invention.

"Prodrug" means a derivative that is converted into a compound according to the present invention by a reaction with an enzyme, gastric acid or the like under a physiological condition in the living body, e.g. by oxidation, reduction, hydrolysis or the like, each of which is carried out enzymatically. Examples of a prodrug are compounds, wherein the amino group in a compound of the present invention is acylated, alkylated or phosphorylated to form, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated. These compounds can be produced from compounds of the present invention according to well-known methods.

Metabolites of compounds of formula (I) are also within the scope of the present invention.

The term "metabolites" refers to all molecules derived from any of the compounds according to the present invention in a cell or organism, preferably mammal.

Preferably the term relates to molecules which differ from any molecule which is present in any such cell or organism under physiological conditions The structure of the metabolites of the compounds according to the present invention will be obvious to any person skilled in the art, using the various appropriate methods.

Where tautomerism, like e.g. keto-enol tautomerism, of compounds of general formula (I) may occur, the individual forms, like e.g. the keto and enol form, are comprised separately and together as mixtures in any ratio. The same applies for stereoisomers, like e.g. enantiomers, cis/trans isomers, conformers and the like.

Especially, compounds of formula (I), wherein the morpholino ring is substituted with one $R^3$ in 3-position are encompassed by the present invention as isomers or enantiomers or mixtures thereof concerning the respective chiral carbon center.

If desired, isomers can be separated by methods well known in the art, e.g. by liquid chromatography. The same applies for enantiomers by using e.g. chiral stationary phases. Additionally, enantiomers may be isolated by converting them into diastereomers, i.e. coupling with an enantiomerically pure auxiliary compound, subsequent separation of the resulting diastereomers and cleavage of the auxiliary residue. Alternatively, any enantiomer of a compound of formula (I) may be obtained from stereoselective synthesis using optically pure starting materials.

The compounds of formula (I) may exist in crystalline or amorphous form. Furthermore, some of the crystalline forms of the compounds of formula (I) may exist as polymorphs, which are included within the scope of the present invention. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (ssNMR).

In case the compounds according to formula (I) contain one or more acidic or basic groups, the invention also comprises their corresponding pharmaceutically or toxicologically acceptable salts, in particular their pharmaceutically utilizable salts. Thus, the compounds of the formula (I) which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the formula (I) which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the formula (I) simultaneously contain acidic and basic groups in the molecule, the invention also includes, in addition to the salt forms mentioned, inner salts or betaines (zwitterions). The respective salts according to the formula (I) can be obtained by customary methods which are known to the person skilled in the art like, for example by contacting these with an organic or inorganic acid or base in a solvent or dispersant, or by anion exchange or cation exchange with other salts. The present invention also includes all salts of the compounds of the formula (I) which, owing to low physiological compatibility, are not directly suitable for use in pharmaceuticals but which can be used, for example, as intermediates for chemical reactions or for the preparation of pharmaceutically acceptable salts.

Throughout the invention, the term "pharmaceutically acceptable" means that the corresponding compound, carrier or molecule is suitable for administration to humans. Preferably, this term means approved by a regulatory agency such as the EMEA (Europe) and/or the FDA (US) and/or any other national regulatory agency for use in animals, preferably in humans.

The present invention furthermore includes all solvates of the compounds according to the invention.

If desired, the effects of the claimed compounds on mTOR activity may e.g. be tested using transiently expressed epitope-tagged mTOR in a mammalian cell line such as HEK293 that is immunoprecipitated with a monoclonal antibody directed against the epitope tag (Knight et al. 2004, Bioorganic and Medicinal Chemistry 12, 4749-4759). Another assay employs mTOR protein enriched from cells or tissue lysates using conventional protein purification methods. In this assay a GST-fusion protein of the P70 S6 kinase is used as a substrate. The phosphorylation of P70 S6 is detected using a primary phospho-specific antibody (directed against phosphorylated threonine 389) and an enzyme linked secondary anti-body in an ELISA assay (US-A 2004/0191836).

According to the present invention, the expression "mTOR" or "mTOR kinase" means the mTOR protein (Tsang et al., 2007, Drug Discovery Today 12, 112-124). The gene encoding mTOR is located on human chromosome map locus 1p36.2 and it is widely expressed in human tissues.

As shown in the examples, compounds of the invention were tested for their selectivity for mTOR over other kinases. As shown, tested compounds bind mTOR more selectively than the kinases PI3 Kdelta or DNA-PK (see table 2 below). Consequently, the compounds of the present invention are considered to be useful for the prevention or treatment of diseases and disorders associated with mTOR, e.g. immunological, inflammatory, autoimmune, or allergic disorders, or proliferative diseases, transplant rejection, Graft-versus-Host-Disease, cardiovascular diseases, metabolic diseases or neurodegenerative diseases.

Therefore, the present invention provides pharmaceutical compositions comprising a compound of formula (I) or a pharmaceutically acceptable salt thereof as active ingredient together with a pharmaceutically acceptable carrier, optionally in combination with one or more other pharmaceutical compositions.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water is a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E.W. Martin. Such compositions will contain a therapeutically effective amount of the therapeutic, preferably in purified form, together with a suitable amount of carrier so as to provide the form for proper administration to the patient. The formulation should suit the mode of administration.

A pharmaceutical composition of the present invention may comprise one or more additional compounds as active ingredients like one or more compounds of formula (I) not being the first compound in the composition or mTOR inhibitors. Further bioactive compounds for may be steroids, leukotriene antagonists, cyclosporine or rapamycin.

The compounds of the present invention or pharmaceutically acceptable salt(s) thereof and the other pharmaceutically active agent(s) may be administered together or separately and, when administered separately, this may occur separately or sequentially in any order. When combined in the same formulation it will be appreciated that the two compounds must be stable and compatible with each other and the other components of the formulation. When formulated separately they may be provided in any convenient formulation, conveniently in such manner as are known for such compounds in the art.

It is further included within the present invention that the compound of formula (I), or a pharmaceutically acceptable salt thereof, or a pharmaceutical composition comprising a compound of formula (I) is administered in combination with another drug or pharmaceutically active agent and/or that the pharmaceutical composition of the invention further comprises such a drug or pharmaceutically active agent.

In this context, the term "drug or pharmaceutically active agent" includes a drug or pharmaceutical agent that will elicit the biological or medical response of a tissue, system, animal or human that is being sought, for instance, by a researcher or clinician.

"Combined" or "in combination" or "combination" should be understood as a functional coadministration, wherein some or all compounds may be administered separately, in different formulations, different modes of administration (for example subcutaneous, intravenous or oral) and different times of administration. The individual compounds of such combinations may be administered either sequentially in separate pharmaceutical compositions as well as simultaneously in combined pharmaceutical compositions.

For example, in rheumatoid arthritis therapy, combination with other chemotherapeutic or antibody agents is envisaged. Suitable examples of pharmaceutically active agents which may be employed in combination with the compounds of the present invention and their salts for rheumatoid arthritis therapy include: immunosuppresants such as amtolmetin guacil, mizoribine and rimexolone; anti-TNFα agents such as etanercept, infliximab, Adalimumab, Anakinra, Abatacept, Rituximab; tyrosine kinase inhibitors such as leflunomide; kallikrein antagonists such as subreum; interleukin 11 agonists such as oprelvekin; interferon beta 1 agonists; hyaluronic acid agonists such as NRD-101 (Aventis); interleukin 1 receptor antagonists such as anakinra; CD8 antagonists such as amiprilose hydrochloride; beta amyloid precursor protein antagonists such as reumacon; matrix metalloprotease inhibitors such as cipemastat and other disease modifying antirheumatic drugs (DMARDs) such as methotrexate, sulphasalazine, cyclosporin A, hydroxychoroquine, auranofin, aurothioglucose, gold sodium thiomalate and penicillamine.

In particular, the treatment defined herein may be applied as a sole therapy or may involve, in addition to the compounds of the invention, conventional surgery or radiotherapy or chemotherapy. Accordingly, the compounds of the invention can also be used in combination with existing therapeutic agents for the treatment proliferative diseases such as cancer. Suitable agents to be used in combination include:

(i) antiproliferative/antineoplastic drugs and combinations thereof, as used in medical oncology such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea and gemcitabine); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like paclitaxel and taxotere); and topoisomerase inhibitors (for example epipodophyllotoxins like etoposide and teniposide, amsacrine, topotecan and camptothecins);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxy-quinazoline (AZD0530) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825), and metalloproteinase inhibitors like marimastat and inhibitors of urokinase plasminogen activator receptor function);

(iv) inhibitors of growth factor function: for example such inhibitors include growth factor antibodies and growth factor receptor antibodies (for example the anti-erbB2 antibody trastuzumab [Herceptin™] and the anti-erbB1 antibody cetuximab [C225]); such inhibitors also include, for example, tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD 1839), V/-(3-ethynylphenyl)-6,7-bis(2-methoxyethoxy)quinazolin-4-amine (erlotinib, OSI-774) and 6-acrylamido-V/-(3-chloro-4-fluorophenyl)-7-(3-morpholinopropoxy)-quinazolin-4-amine (CI-1033) and erbB2 tyrosine kinase inhibitors such as lapatinib), inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)) and inhibitors of cell signalling through MEK and/or Akt kinases;

(v) antiangiogenic agents such as those which inhibit the effects of vascular endothelial growth factor, for example the anti-vascular endothelial cell growth factor antibody bevacizumab (Avastin™) and VEGF receptor tyrosine kinase inhibitors such as 4-(4-bromo-2-fiuoroanilino)-6-methoxy-7-(1-methylpiperidin-4-ylmethoxy)quinazo line (ZD6474; Example 2 within WO 01/32651), 4-(4-fluoro-2-methylindol-5-yloxy)-6-methoxy-7-(3-pyrrolidin-1-yl-propoxy)quinazoline (AZD2171; Example 240 within WO 00/47212), vatalanib (PTK787; WO 98/35985) and SU11248 (sunitinib; WO 01/60814), and compounds that work by other mechanisms (for example linomide, inhibitors of integrin αvβ3 function and angio statin);

(vi) vascular damaging agents such as combretastatin A4 and compounds disclosed in International Patent Application WO 99/02166;

(vii) antisense therapies, for example those which are directed to the targets listed above, such as ISIS 2503, an anti-ras antisense agent;

(viii) gene therapy approaches, including approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapeutic approaches, including ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Further combination treatments are described in WO-A 2009/008992, incorporated herein by reference.

Accordingly, the individual compounds of such combinations may be administered either sequentially in separate pharmaceutical compositions as well as simultaneously in combined pharmaceutical compositions.

The pharmaceutical compositions of the present invention include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of formula (I) can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally, for example, as liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula (I) may also be administered parenterally. Solutions or suspensions of these active compounds can be prepared in water suitably mixed with a surfactant such as hydroxypropyl-cellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of formula (I) are administered orally.

The effective dosage of active ingredient employed may vary depending on the particular compound employed, the mode of administration, the condition being treated and the severity of the condition being treated. Such dosage may be ascertained readily by a person skilled in the art.

A therapeutically effective amount of a compound of the present invention will normally depend upon a number of factors including, for example, the age and weight of the animal, the precise condition requiring treatment and its severity, the nature of the formulation, and the route of administration. However, an effective amount of a compound of formula (I) for the treatment of an inflammatory disease, for example rheumatoid arthritis (RA), will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a pharmaceutically acceptable salt, prodrug or metabolite thereof, may be determined as a proportion of the effective amount of the compound of formula (I) per se. It is envisaged that similar dosages would be appropriate for treatment of the other conditions referred to above.

As used herein, the term "effective amount" means that amount of a drug or pharmaceutical agent that will elicit the biological or medical response of a tissue, system, animal or human that is being sought, for instance, by a researcher or clinician.

Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Another aspect of the present invention is a compound of the present invention or a pharmaceutically acceptable salt thereof for use as a medicament.

Another aspect of the present invention is a compound of the present invention or a pharmaceutically acceptable salt thereof for use in a method of treating or preventing a disease or disorder associated with mTOR.

In the context of the present invention, a disease or disorder associated with mTOR is defined as a disease or disorder where mTOR is involved.

In a preferred embodiment, the diseases or disorder associated with mTOR is an immunological, inflammatory, autoimmune, or allergic disorder or disease or a transplant rejection or a Graft-versus host disease.

Consequently, another aspect of the present invention is a compound or a pharmaceutically acceptable salt thereof of the present invention for use in a method of treating or preventing an immunological, inflammatory, autoimmune, or allergic disorder or disease or a transplant rejection or a Graft-versus host disease.

According to the present invention, an autoimmune disease is a disease which is at least partially provoked by an immune reaction of the body against own components, e.g. proteins, lipids or DNA.

In a preferred embodiment, the autoimmune disease is selected from the group consisting of rheumatoid arthritis (RA), inflammatory bowel disease (IBD; Crohns's disease and ulcerative colitis), psoriasis, systemic lupus erythematosus (SLE), and multiple sclerosis (MS).

Rheumatoid arthritis (RA) is a chronic progressive, debilitating inflammatory disease that affects approximately 1% of the world's population. RA is a symmetric polyarticular arthritis that primarily affects the small joints of the hands and feet. In addition to inflammation in the synovium, the joint lining, the aggressive front of tissue called pannus invades and destroys local articular structures (Firestein 2003, Nature 423:356-361).

Inflammatory bowel disease (IBD) is characterized by a chronic relapsing intestinal inflammation. IBD is subdivided into Crohn's disease and ulcerative colitis phenotypes. Crohn disease involves most frequently the terminal ileum and colon, is transmural and discontinuous. In contrast, in ulcerative colitis, the inflammation is continuous and limited to rectal and colonic mucosal layers. In approximately 10% of cases confined to the rectum and colon, definitive classification of Crohn disease or ulcerative colitis cannot be made and are designated 'indeterminate colitis.' Both diseases include extraintestinal inflammation of the skin, eyes, or joints. Neutrophil-induced injuries may be prevented by the use of neutrophils migration inhibitors (Asakura et al., 2007, World J. Gastroenterol. 13(15):2145-9).

Psoriasis is a chronic inflammatory dermatosis that affects approximately 2% of the population. It is characterized by red, scaly skin patches that are usually found on the scalp, elbows, and knees, and may be associated with severe arthritis. The lesions are caused by abnormal keratinocyte proliferation and infiltration of inflammatory cells into the dermis and epidermis (Schöll et al., 2005, New Engl. J. Med. 352: 1899-1912).

Systemic lupus erythematosus (SLE) is a chronic inflammatory disease generated by T cell-mediated B-cell activation, which results in glomerulonephritis and renal failure. Human SLE is characterized at early stages by the expansion of long-lasting autoreactive CD4+ memory cells (D'Cruz et al., 2007, Lancet 369(9561):587-596).

Multiple sclerosis (MS) is an inflammatory and demyelating neurological disease. It has bee considered as an autoimmune disorder mediated by CD4+ type 1 T helper cells, but recent studies indicated a role of other immune cells (Hemmer et al., 2002, Nat. Rev. Neuroscience 3, 291-301).

Graft-versus-host disease (GVDH) is a major complication in allogeneic bone marrow transplantation. GVDH is caused by donor T cells that recognize and react to recipient differences in the histocompatibility complex system, resulting in significant morbidity and mortality.

Transplant rejection (allograft transplant rejection) includes, without limitation, acute and chronic allograft rejection following for example transplantation of kidney, heart, liver, lung, bone marrow, skin and cornea. It is known that T cells play a central role in the specific immune response of allograft rejection.

In a further preferred embodiment, the disease or disorder associated with mTOR is a proliferative disease, especially cancer.

Diseases and disorders associated especially with mTOR are proliferative disorders or diseases, especially cancer.

Therefore, another aspect of the present invention is a compound or a pharmaceutically acceptable salt thereof of the present invention for use in a method of treating or preventing a proliferative disease, especially cancer.

Cancer comprises a group of diseases characterized by uncontrolled growth and spread of abnormal cells. All types of cancers generally involve some abnormality in the control of cell growth, division and survival, resulting in the malignant growth of cells. Key factors contributing to said malignant growth of cells are independence from growth signals, insensitivity to anti-growth signals, evasion of apoptosis, limitless replicative potential, sustained angiogenesis, tissue invasion and metastasis, and genome instability (Hanahan and Weinberg, 2000. The Hallmarks of Cancer. Cell 100, 57-70).

Typically, cancers are classified as hematological cancers (for example leukemias and lymphomas) and solid cancers such as sarcomas and carcinomas (for example cancers of the brain, breast, lung, colon, stomach, liver, pancreas, prostate, ovary).

Especially cancers in which the PI3K/Akt signal transduction pathway is activated, for example due to inactivation of the tumour suppressor PTEN or activating mutations in PIK3A, the gene encoding the catalytic phosphoinositide-3 kinase subunit p110α (p110alpha) are expected to respond to treatment with mTOR inhibitors (Garcia-Echeverria and Sellers, 2008, Oncogene 27, 5511-5526). Examples of cancers with a high incidence of PTEN mutations and/or activation of PI3K/Akt are endometrial carcinoma, glioblastoma, head and neck cancer, colon cancer, pancreatic cancer, gastric cancer, hepatocarcinoma, ovarian cancer, thyroid carcinoma, renal cell cancer, breast cancer, prostate cancer and gastrointestinal stromal tumours (GIST). The most promising results with mTOR inhibitors have been obtained in renal cell carcinoma (RCC), mantle cell lymphoma and endometrial cancers (Faivre et al., 2006. Nat. Rev. Drug. Discov. 5(8):671-688). In addition, mTOR inhibitors may be useful for the treatment of leukemias Including ALL and CML, multiple myeloma and lymphomas.

In addition, cancers harbouring activating mTOR mutations, for example single amino acid changes that confer constitutive activation of mTOR such as S2215Y or R2505P, may be treated with mTOR inhibitors (Sato et al., 2010, Oncogene 29(18):2746-2752).

mTOR plays an important role in angiogenesis, the formation of new blood vessels to provide oxygen and nutrients to growing and dividing cells. In this context mTOR controls the production of the HIF1-α and HIF 1-β proteins, which are subunits of hypoxia-inducible factor (HIF), a transcription factor that controls the expression of genes whose products play a role in angiogenesis, cell proliferation, motility and survival. Two important proteins induced by HIF are vascular endothelial growth factors (VEGFs) and angiopoietin-2. Recently it has been reported that a small molecule mTOR inhibitor can reduce tumour growth, tumour angiogenesis an vascular permeability (Xue et al., 2008. Cancer Research 68(22): 9551-9557).

In addition to tumourigenesis, there is evidence that mTOR plays a role in harmatoma syndromes. Recent studies have shown that the tumour suppressor proteins such as TSC1, TSC2, PTEN and LKB1 tightly control mTOR signalling. Loss of these tumour suppressor proteins leads to a range of hamartoma conditions as a result of elevated mTOR signalling (Rosner et al., 2008. Mutation Research 659(3):284-292). Syndromes with an established molecular link to dysregulation of mTOR include Peutz-Jeghers syndrome (PJS), Cowden disease, Bannayan-Riley-Ruvalcaba syndrome (BRRS), Proteus syndrome, Lhermitte-Duclos disease and Tuberous sclerosis (TSC). Patients with these syndromes characteristically develop benign hamartomatous tumours in multiple organs. Other tumour suppressor proteins having an influence on mTOR activity are VHL, NF1 and PKD whose loss can trigger von Hippel-Lindau disease, Neurofibromatosis type 1, and Polycystic kidney disease respectively. Proliferative diseases or disorders comprise a group of diseases characterized by increased cell multiplication. One example is restenosis caused by the overgrowth of vascular smooth muscle (VSM) cells after coronary angioplasty with stents. To circumvent this issue, drug-eluting stents have been developed to inhibit the growth of VSM cells. Rapamycin-coated stents effectively reduce restenosis and have been approved by the FDA (Serruys et al., 2006. N. Engl. J. Med. 354(5): 483-95).

In a further preferred embodiment, the disease or disorder associated with mTOR is a cardiovascular disease, a metabolic disease or a neurodegenerative disease.

Therefore, another aspect of the present invention is a compound or a pharmaceutically acceptable salt thereof of the present invention for use in a method of treating or preventing a cardiovascular disease, a metabolic disease or a neurodegenerative disease.

Recent studies have revealed a role of mTOR in cardiovascular diseases, for example elevated mTOR kinase activity has been associated with cardiac hypertrophy (heart enlargement), which is a major risk factor for heart failure. At the cellular level, cardiac hypertrophy is characterized by an increase in cell size and enhanced protein synthesis. Although there are various hypertrophic stimuli, such as neurohormones and peptide growth factors, and several protein kinase cascades are involved in cardiac hypertrophy, it is likely that all forms of hypertrophic stimuli activate the general protein translational machinery in an mTOR dependent manner. Remarkably, inhibition of mTOR by rapamycin prevents cardiac hypertrophy in numerous transgenic mouse models. In addition, stress-induced cardiac hypertrophy is dependent on mTOR in mice. These results indicate that mTOR is crucial for the abnormal cardiac overgrowth, and that mTOR inhibitors may be usefull for the treatment of human cardiac hypertrophy (Tsang et al., 2007, Drug Discovery Today 12, 112-124).

Metabolic diseases that may be treated with mTOR inhibitors comprise type 1 diabetes, type 2 diabetes, and obesity (Tsang et al., 2007, Drug Discovery Today 12, 112-124). Type 1 diabetes is caused by loss of insulin production due to destruction of pancreatic β-cells. Clinical studies using immunosuppressive regimen that contain rapamycin to prevent rejection of islet transplants have shown significant efficacy in type 1 diabetic patients. Type 2 diabetes arises when insulin secretion from pancreatic β-cells fails to compensate for the peripheral insulin resistance (or insensitivity to insulin) in skeletal muscle, liver and fat cells. Recent data indicate that sustained activation of mTOR signalling is a crucial event that renders insulin-receptors substrate (IRS) irresponsive to insulin. Moreover, it has been demonstrated that rapamycin restores the sensitivity of IRS to insulin (Shah et al., 2004. Curr. Biol. 14(18):1650-1656). Therefore, mTOR inhibitors are potentially useful in the management of type 2 diabetes. Obesity is a metabolic disease with a steadily increasing health risk worldwide. Recent evidence suggests that mTOR plays a role in lipid metabolism. During adipogenesis the expression of mTOR increases dramatically from barely detectable in preadipocytes to highly expressed in fully differentiated adipocytes, and rapamycin inhibits adipocyte differentiation (Yeh et al., 1995. Proc. Natl. Acad. Sci. USA. 92(24):11086-90).

Recent reports suggest that mTOR inhibitors may be useful to treat neurodegenerative diseases such as Huntingtons's, Alzheimer's and Parkinson's disease. Huntingtons's disease is a neurodegenerative disorder caused by a mutant form of the protein huntingtin with abnormally long glutamine repeats at the amino-terminus. The mutant protein aggregates in neuronal cells and can cause nerve cell damage and toxicity. Rapamycin attenuates the accumulation of huntingtin and cell death, and protects against neurodegeneration in animal models of Huntington's disease (Ravikumar et al., 2004. Nat Genet. 36(6):585-95). In addition, rapamycin induces an autophagy response that has been suggested to play a role in the clearance of huntingtin aggregates.

Intracellular protein aggregates also occur in other neurodegenerative diseases, for example Alzheimer's disease. The Tau protein is frequently found in brains of Alzheimer's patients and is thought to contribute to the formation of neurofibrillary tangles (for example in tauopathies such as fronto-temporal dementia). In a fly model rapamycin reduces the concentration of tau protein and lowers the toxicity caused by tau accumulation (Berger et al., 2006. Hum Mol Genet. 2006 Feb. 1; 15(3):433-42). Therefore, mTOR inhibitors may be useful in preventing the accumulation of toxic tau protein in Alzheimer's patients.

Parkinson's disease (PD) is a neurodegenerative disease associated with the accumulation and aggregation of misfolded proteins. Preventing aggregation or disaggregating misfolded proteins may provide a therapeutic benefit by slowing or preventing the progression of PD. The ubiquitin-proteasome system (UPS) is an important degradation mechanism acting on aggregated proteins. It was reported that rapamycin provides neuroprotection against dopaminergic neuronal cell death induced by the proteasome inhibitor lactacystin. It was suggested that the rapamycin effect is partially mediated by autophagy enhancement through enhanced degradation of misfolded proteins (Pan et al., 2008. Neurobiol. Dis. 32(1):16-25). Therefore compounds that can enhance autophagy may represent a promising strategy to treat PD patients.

In a further preferred embodiment, the disease or disorder associated with mTOR is an autophagy associated disease.

Therefore, another aspect of the present invention is a compound or a pharmaceutically acceptable salt thereof of the present invention for use in a method of treating or preventing an autophagy associated disease.

Autophagy is a lysosome-dependent process whereby proteins or damaged organelles within a cell are degraded (Mizushima et al., 2008. Nature 451(7182):1069-75). During this process an autophagosome with a double membrane encloses the component of the cell to be degraded. Then the autophagosome fuses with a lysosome which for example degrades proteins leading to the recycling of amino acids. Autophagy is primarily involved in the degradation of long-lived proteins, protein aggregates, and cellular organelles and other cellular components. In addition to its physiological function autophagy could be expoited for the treatment of a variety of diseases caused by misfolded proteins aggregates, for example neurodegenerative diseases such as Huntington's, Alzheimer's or Parkinon's disease. Further autophagy associated diseases are described in W0-A2009/049242, incorporated herein with reference.

Autophagy inducing compound refers to a compound that induces autophagy in a cell. Autophagy associated disease refers to a disease that can be treated by the induction of autophagy. It has recently been shown that an ATP-competitive mTOR kinase inhibitor can induce autophagy (Thoreen et al., 2009. J. Biol. Chem. 284(12):8023-32). Interestingly, ATP competitive mTOR kinase inhibitors seem to induce autophagy more effectively than rapamycin in mammalian cells. Taken together, compounds of the present invention may be useful to induce autophagy in cells and to treat autophagy associated diseases.

In a further preferred embodiment, the disease or disorder is a viral infection.

Therefore, another aspect of the present invention is a compound or a pharmaceutically acceptable salt thereof of the present invention for use in a method of treating or preventing a viral infection.

All viruses require cellular ribosomes to translate their mRNAs. For example, Human cytomegalovirus (HCMV) infection has been shown to activate the mTORC1 signaling pathway. Treatment of infected cells with Torinl, a mTOR inhibitor that targets the catalytic site of mTOR kinase, blocks the production of virus progeny. In addition, it was shown that Torinl inhibits the replication of representative members of the alpha-, beta-, and gammaherpesvirus families, demonstrating the potential of mTOR kinase inhibitors as broad-spectrum antiviral agents (Moorman and Shenk, 2010. J. Viol. 84(10):5260-9). Further viral infections that may be treated or prevented by mTOR inhibitors are described in WO-A 2011/011716 incoporated herin with reference.

Yet another aspect of the present invention is the use of a compound of the present invention or a pharmaceutically acceptable salt thereof for the manufacture of a medicament for the treatment or prophylaxis of diseases and disorders associated with mTOR.

Yet another aspect of the present invention is the use of a compound of the present invention or a pharmaceutically acceptable salt thereof for the manufacture of a medicament for treating or preventing an immunological, inflammatory, autoimmune, or allergic disorder or disease or a transplant rejection or a Graft-versus host disease.

Yet another aspect of the present invention is the use of a compound of the present invention or a pharmaceutically acceptable salt thereof for the manufacture of a medicament for treating or preventing a proliferative disease, especially cancer.

Yet another aspect of the present invention is the use of a compound of the present invention or a pharmaceutically acceptable salt thereof for the manufacture of a medicament for treating or preventing a cardiovascular disease, a metabolic disease or a neurodegenerative disease.

Yet another aspect of the present invention is the use of a compound of the present invention or a pharmaceutically acceptable salt thereof for the manufacture of a medicament for treating or preventing an autophagy associated disease.

Yet another aspect of the present invention is the use of a compound of the present invention or a pharmaceutically acceptable salt thereof for the manufacture of a medicament for treating or preventing a viral infection.

In the context of these uses of the invention, diseases and disorders associated with mTOR are as defined above.

Yet another aspect of the present invention is a method for treating, controlling, delaying or preventing in a mammalian patient in need thereof one or more conditions selected from the group consisting of diseases and disorders associated with mTOR, wherein the method comprises the administration to said patient a therapeutically effective amount of a compound according to present invention or a pharmaceutically acceptable salt thereof.

Yet another aspect of the present invention is a method for treating, controlling, delaying or preventing in a mammalian patient in need thereof one or more conditions selected from the group consisting of an immunological, inflammatory, autoimmune, or allergic disorder or disease or a transplant rejection or a Graft-versus host disease, wherein the method comprises the administration to said patient a therapeutically effective amount of a compound according to present invention or a pharmaceutically acceptable salt thereof.

Yet another aspect of the present invention is a method for treating, controlling, delaying or preventing in a mammalian patient in need thereof a proliferative disease, especially cancer, wherein the method comprises the administration to said patient a therapeutically effective amount of a compound according to present invention or a pharmaceutically acceptable salt thereof.

Yet another aspect of the present invention is a method for treating, controlling, delaying or preventing in a mammalian patient in need thereof one or more conditions selected from the group consisting of a cardiovascular disease, a metabolic disease or a neurodegenerative disease, wherein the method comprises the administration to said patient a therapeutically effective amount of a compound according to present invention or a pharmaceutically acceptable salt thereof.

Yet another aspect of the present invention is a method for treating, controlling, delaying or preventing in a mammalian patient in need thereof an autophagy associated disease, wherein the method comprises the administration to said patient a therapeutically effective amount of a compound according to present invention or a pharmaceutically acceptable salt thereof.

Yet another aspect of the present invention is a method for treating, controlling, delaying or preventing in a mammalian patient in need thereof a viral infection, wherein the method comprises the administration to said patient a therapeutically effective amount of a compound according to present invention or a pharmaceutically acceptable salt thereof.

In the context of these methods of the invention, diseases and disorders associated with mTOR are as defined above.

As used herein, the term "treating" or "treatment" is intended to refer to all processes, wherein there may be a slowing, interrupting, arresting, or stopping of the progression of a disease, but does not necessarily indicate a total elimination of all symptoms.

All embodiments discussed above with respect to the pharmaceutical composition of the invention also apply to the above mentioned first or second medical uses or methods of the invention.

In general compounds of the present invention may be prepared according to a method comprising the steps of
(a) reacting a compound of formula (II)

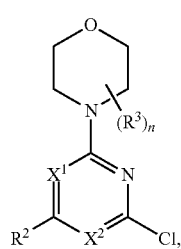

(II)

wherein $R^3$, n, $X^1$, $X^2$ have the meaning as indicated above and $R^{2'}$ is H when $R^2$ is H, or $R^{2'}$ is Cl when $R^2$ is $T^2$ with a compound of formula (III)

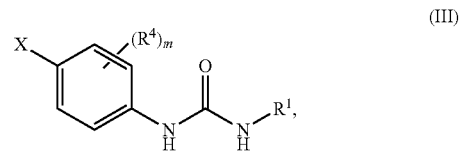

(III)

wherein $R^1$, $R^4$, m have the meaning as indicated above and X is a boronic acid or ester in a Suzuki reaction to yield a compound of formula (I), wherein $R^2$ is H; or when $R^2$ is $T^2$ (a') reacting the compound of formula (II) in two Suzuki reactions with a compound of formula $R^2$—X, wherein X is a boronic acid or boronic ester, and subsequently with a compound of formula (III) to yield a compound of formula (I), wherein $R^2$ is $T^2$.

It will be appreciated that novel intermediates described herein form another embodiment of the present invention.

EXAMPLES

Abbreviations

| | |
|---|---|
| amu | Atomic mass units |
| Boc | Tert-butyl carboxylate |
| br | Broad |
| brine | Saturated aqueous solution of sodium chloride |
| CPME | Cyclopentyl methyl ether |
| d | Doublet |
| $d^6$-DMSO | Deuterated dimethylsulfoxide |
| DCM | Dichloromethane |
| dd | Double doublet |
| DIPEA | Diisopropylethylamine |
| DME | 1,2-Dimethoxyethane |
| DMF | N,N-Dimethylformamide |
| DMSO | Dimethylsulfoxide |
| EDC | N-Ethyl-N'-(3-dimethylaminopropyl)carbodiimide hydrochloride |
| Et | Ethyl |
| $Et_3N$ | Triethylamine |
| EtOAc | Ethyl acetate |
| EtOH | Ethanol |
| g | Grams |
| h | Hour(s) |
| $H_2O$ | Water |
| HCl | Hydrogen chloride |
| HOBt | 1-Hydroxybenzotriazole |
| HPLC | High Performance Liquid Chromatography |
| $^iPr$ | Isopropyl |
| LCMS | Liquid Chromotography Mass Spectrometry |
| m | Multiplet |
| MeCN | Acetonitrile |
| MeOH | Methanol |
| min | Minute(s) |
| mL | Millilitres |
| mm | Millimetres |
| mmol | Millimoles |
| mp-TsOH | Polystyrene resin supported p-toluenesulfonic acid |
| $Na_2CO_3$ | Sodium carbonate |
| $Na_2SO_4$ | Sodium sulfate |
| $NaHCO_3$ | Sodium hydrogen carbonate |
| $NH_3$ | Ammonia |
| NMR | Nuclear magnetic resonance |
| ° C. | Degrees celsius |
| $Pd(PPh_3)_2(Cl)_2$ | Bis(triphenylphosphine)palladium(II)chloride |
| prep. | Preparative |
| PTFE | Poly(tetrafluoroethene) |
| q | Quartet |
| qn | Quintet |

-continued

| | |
|---|---|
| Rt | Retention time |
| RT | Room Temperature |
| s | Singlet |
| sat | Saturated |
| spec | Spectrometry |
| t | Triplet |
| TFA | Trifluoroacetic acid |
| THF | Tetrahydrofuran |
| uM | Micromolar |

Analytical Methods

Analysis was performed on an Agilent 1100 system with following conditions.
Solvents: A=Water with 0.1% formic acid
B=Acetonitrile with 0.1% formic acid
C=Water with 0.1% ammonia
D=Acetonitrile with 0.1% ammonia
Temperature: 40° C.
Wavelength: 254 nm and 210 nm Mass spec data were gathered in positive electrospray ionisation mode from 150 and 700 amu.

Method A
Column: Phenomenex Gemini-C18, 4.6×150 mm, 5 microns
Gradient Conditions:

| Time (min) | % A | % B |
|---|---|---|
| 0.00 | 95.0 | 5.0 |
| 11.00 | 5.0 | 95.0 |
| 13.00 | 5.0 | 95.0 |
| 13.01 | 95.0 | 5.0 |
| 14.00 | 95.0 | 5.0 |

Flow Rate: 1 ml/min
Method B
Column: Phenomenex Gemini-C18, 3.0×30 mm, 3 microns
Gradient Conditions:

| Time (min) | % A | % B |
|---|---|---|
| 0.00 | 95.0 | 5.0 |
| 3.00 | 5.0 | 95.0 |
| 4.50 | 5.0 | 95.0 |
| 4.60 | 95.0 | 5.0 |
| 5.00 | 95.0 | 5.0 |

Flow Rate: 1.2 ml/min
Method C
Column: Phenomenex Gemini-C18, 3.0×30 mm, 3 microns
Gradient Conditions:

| Time (min) | % C | % D |
|---|---|---|
| 0.00 | 95.0 | 5.0 |
| 3.00 | 0.0 | 100.0 |
| 4.50 | 0.0 | 100.0 |
| 4.60 | 95.0 | 5.0 |
| 5.00 | 95.0 | 5.0 |

Flow Rate: 1.2 ml/min

Alternatively analysis was performed on a Waters uPLC-SQD system
Temperature: 40° C.
Wavelength: Photodiode array detection 210-400 nm The mass spec data are gathered in positive or negative mode, scanning for masses between 150 and 700 amu.

Method D
Column: Waters Acquity UPLC BEH C18, 2.1×30 mm, 1.7 microns
Solvents: A1=Water with 0.1% formic acid
B1=Acetonitrile with 0.1% formic acid
Gradient Conditions:

| Time (min) | % A1 | % B1 |
|---|---|---|
| 0.00 | 95.0 | 5.0 |
| 0.20 | 95.0 | 5.0 |
| 1.00 | 5.0 | 95.0 |
| 1.50 | 5.0 | 95.0 |
| 1.70 | 95.0 | 5.0 |
| 2.70 | 95.0 | 5.0 |

Flow Rate: 0.5 ml/min
NMR

NMR spectra were obtained on a Brucker DPX400 machine

Microwave

Microwave reactions were carried out in a Biotage Initiator Microwave Synthesizer Preparative LCMS Conditions Samples were purified on a Waters—ZQ prep system using the following conditions:
Column: Phenomenex Gemini C18 100×30 mm 5 μm
Solvents: Low pH
A=Water+0.1% Formic acid
B=(95% Acetonitrile: 5% Water)+0.1% Formic acid
High pH
C=Water with 0.1% ammonia
D=(95%: 5%, acetonitrile: water) with 0.1% ammonia
Flow Rate: 35 ml/min
Temperature: Room temperature
Wavelength: Photo Diode Array 190-600 nm.
Mass spec.: The mass spec. data were gathered in positive and negative mode, from 150 to 700 amu, using atmospheric pressure and electrospray ionisation modes.
Gradient conditions: Variable depending on the retention time of each compound.
Flash Chromatography Purification Flash chromatography was generally carried out using Biotage Isolute Flash silica cartridges utilising either Flash Master II, Flash Master Personal or Isolera equipment.

Experimental

Intermediate 1A (S)-4-(2,6-dichloropyrimidin-4-yl)-3-methylmorpholine

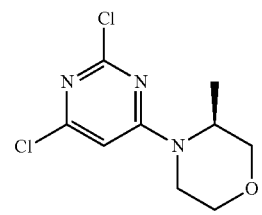

Intermediate 1B (S)-4-(4,6-dichloropyrimidin-2-yl)-3-methylmorpholine

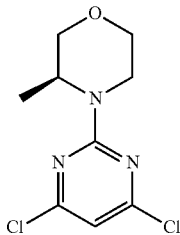

To a solution of trichloropyrimidine (5.04 g, 27.3 mol) in DCM (50 mL) cooled to 0° C. was added DIPEA (4.79 mL, 27.3 mol), followed by 3-(S)-methylmorpholine (3.11 g, 30.5 mol) dropwise. The reaction mixture was allowed to warm to RT and stirred for 3 h whereupon it was diluted with DCM, washed with water and brine, dried over magnesium sulfate, filtered and the solvent removed in vacuo. The residue was purified by flash chromatography (5-10% EtOAc in petroleum ether (40-60)) to yield the two isomers.

Intermediate 1A as a white solid 4.66 g, 69%. LCMS (method B), (M+H+) 248, Rt=2.48 min.

Intermediate 1B as white crystals 1.5 g, 22%. LCMS (method B), (M+H+) 248, Rt=3.00 min.

Intermediate 2

(S)-1-(4-(6-chloro-2-(3-methylmorpholino)pyrimidin-4-yl)phenyl)-3-ethylurea

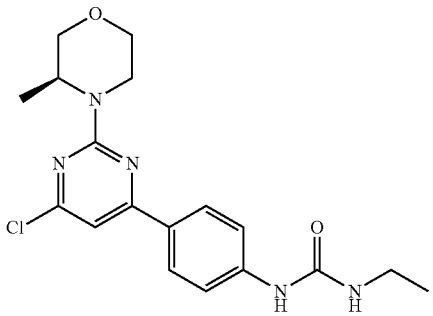 [SMILES: CCNC(=O)Nc1ccc(-c2cc(Cl)nc(N3CCOC[C@@H]3C)n2)cc1]

(S)-4-(4,6-dichloropyrimidin-2-yl)-3-methylmorpholine (Intermediate 1B) (992 mg, 4.0 mmol), 4-(3-ethylureido)phenyl boronic acid pinacol ester (1.05 g, 3.6 mmol), cesium carbonate (3.9 g, 12.0 mmol) and bis(diphenylphosphino)-ferrocenedichloropalladium(II)-DCM-complex (163 mg, 0.2 mmol) in dioxane/water (1:3, 2.4 mL) were irradiated in a Biotage microwave for 40 min at 110° C. The reaction mixture was concentrated in vacuo, the residue suspended in water (150 mL) and the pH adjusted from 10 to 7 with HCl (2M aq solution). EtOAc (150 mL) was added and aqueous layer removed. The organic layer was washed with brine (70 mL) and then concentrated in vacuo to leave a brown solid which was purified by flash chromatography (0-5% MeOH in DCM over 30 min) to yield an orange solid, 630 mg, 42%.

LCMS (method B), (M+H+) 376, Rt=2.88 min.

Intermediate 3

(S)-4-(2-chloropyrimidin-4-yl)-3-methylmorpholine

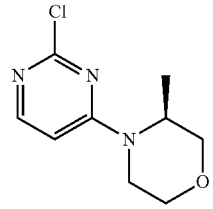

To a solution of 2,4-dichloropyrimidine (5.00 g, 0.034 mol) and DIPEA (8.00 mL, 0.046 mol) in 2-propanol (60 mL) at 0° C. was added (S)-3-methylmorpholine (3.73 g, 0.037 mol) dropwise. The reaction mixture was stirred at 0° C. for 30 min and then allowed to warm to RT and stirred for a further 16 h. Solvent was removed in vacuo and the residue was then partitioned between water and EtOAc. The phases were separated and the organic layer washed with brine, dried over magnesium sulfate, filtered and the solvent removed in vacuo to yield a yellow oil (6.54 g, 91%).

$^1$H NMR (d$_6$-DMSO) δ 8.10 (d, 1H), 6.80 (d, 1H), 4.33 (s, 1H), 4.07-3.95 (m, 1H), 3.91 (dd, 1H), 3.70 (d, 1H), 3.57 (dd, 1H), 3.42 (td, 1H), 3.15 (td, 1H), 1.18 (dd, 3H);

LCMS (method C), (M+H+) 214, Rt=2.08 min.

Intermediate 4

(S)-4-(6-chloro-2-(methylthio)pyrimidin-4-yl)-3-methylmorpholine

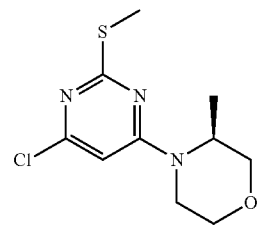 [SMILES: CSc1nc(Cl)cc(N2CCOC[C@@H]2C)n1]

To a solution of 4,6-dichloro-2-(methylthio)pyrimidine (585 mg, 3.0 mmol) in DCM (5 mL) was added DIPEA (1.5 mL, 9.0 mmol), followed by 3-(S)-methylmorpholine (909 mg, 9.0 mmol) dropwise. The reaction mixture was stirred at 40° C. overnight whereupon it was washed with water (10 mL), passed through a PTFE hydrophobic frit and the solvent removed in vacuo to yield a colourless oil (850 mg) used without further purification.

LCMS (method B), (M+H+) 260, Rt=2.58 min.

Intermediate 5

(S)-4-(6-(5-fluoropyridin-3-yl)-2-(methylthio)pyrimidin-4-yl)-3-methylmorpholine

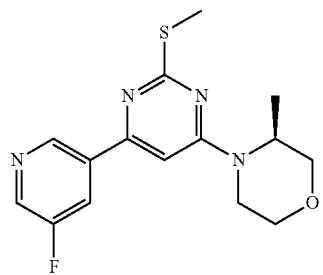 [SMILES: CSc1nc(-c2cncc(F)c2)cc(N2CCOC[C@@H]2C)n1]

A mixture of (S)-4-(6-chloro-2-(methylthio)pyrimidin-4-yl)-3-methylmorpholine (intermediate 4) (850 mg, 3.0 mmol crude), 5-fluoropyridine-3-boronic acid pinacol ester (703 mg, 3.15 mmol), bis(diphenylphosphino)-ferrocenedichloropalladium(II):DCM complex (125 mg, 0.15 mmol) and sodium carbonate (954 mg, 9.0 mmol) in DME/H₂O/EtOH (7:3:2, 12 mL) was heated in the microwave at 100° C. for 60 min. The mixture was then diluted with DCM (80 mL), washed with water (150 mL), the organic layer passed through a PTFE hydrophobic frit and the solvent removed in vacuo to yield a dark brown oil (1.0 g) used without future purification.

LCMS (method B), (M+H+) 321, Rt=2.65 min.

Intermediate 6

(S)-4-(6-(5-fluoropyridin-3-yl)-2-(methylsulfonyl)pyrimidin-4-yl)-3-methylmorpholine

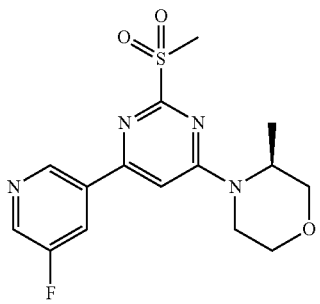 [SMILES: C[C@H]1COCCN1c1cc(-c2cncc(F)c2)nc(S(C)(=O)=O)n1]

To a solution of (S)-4-(6-(5-fluoropyridin-3-yl)-2-(methylthio)pyrimidin-4-yl)-3-methylmorpholine (intermediate 5) (1.0 g, 3.0 mmol) in DCM (40 mL) was added meta-chloroperbenzoic acid (1.62 g, 6.6 mmol) portion wise. The reaction mixture was stirred at room temperature overnight whereupon it was quenched with DMSO (0.2 mL) and stirred for 3 hours. The reaction mixture was washed with water (40 mL), passed through a PTFE hydrophobic frit and the solvent removed in vacuo to yield a orange solid (2.22 g) used without further purification.

LCMS (method B), (M+H+) 353, Rt=2.09 min.

Intermediate 7

(S)-4-(2-chloro-6-(5-fluoropyridin-3-yl)pyrimidin-4-yl)-3-methylmorpholine

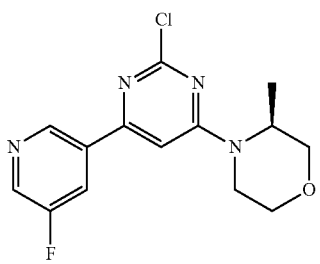 [SMILES: C[C@H]1COCCN1c1cc(-c2cncc(F)c2)nc(Cl)n1]

(S)-4-(6-(5-fluoropyridin-3-yl)-2-(methylsulfonyl)pyrimidin-4-yl)-3-methylmorpholine (intermediate 6) (132 mg, 0.19 mmol) was heated in phosphorus oxychloride (8 mL) overnight at 95° C. The reaction mixture was allowed to cool to room temperature and then portion wise added to ice water (100 mL) and left to stir for 1 hour. Carefully, NaOH pellets were added to basify the mixture. The resulting aqueous layer was extracted with DCM (100 mL), passed through a PTFE hydrophobic frit and the solvent removed in vacuo to yield a brown gum (110 mg) used without further purification.

LCMS (method B), (M+H+) 309, Rt=2.52 min.

Intermediate 8

(S)-4-(6-(5-fluoro-2-(methylthio)phenyl)-2-(methylthio)pyrimidin-4-yl)-3-methylmorpholine

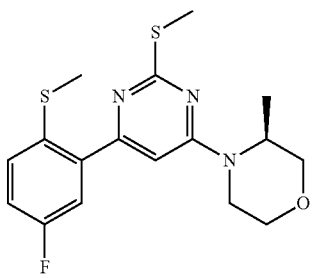 [SMILES: CSc1nc(-c2cc(F)ccc2SC)cc(N2CCOC[C@@H]2C)n1]

Method as described for intermediate 5 using 2-fluoro-2-(methylthio)phenyl boronic acid.

LCMS (method B), (M+H+) 366, Rt=2.80 min.

Intermediate 9

(S)-4-(6-(5-fluoro-2-(methylsulfonyl)phenyl)-2-(methylsulfonyl)pyrimidin-4-yl)-3-methylmorpholine

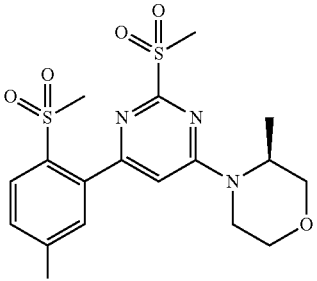

Method as described for intermediate 6 using (S)-4-(6-(5-fluoro-2-(methylthio)phenyl)-2-(methylthio)pyrimidin-4-yl)-3-methylmorpholine (intermediate 8).

LCMS (method B), (M+H+) 430, Rt=2.17 min

Intermediate 10

(S)-4-(2-chloro-6-(5-fluoro-2-(methylsulfonyl)phenyl)pyrimidin-4-yl)-3-methylmorpholine

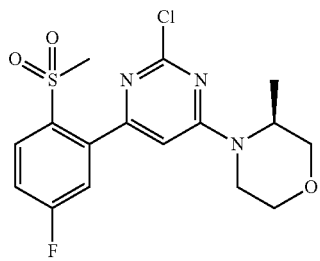 [SMILES: C[C@H]1COCCN1c1cc(-c2cc(F)ccc2S(C)(=O)=O)nc(Cl)n1]

Method as described for intermediate 7 using (S)-4-(6-(5-fluoro-2-(methylsulfonyl)phenyl)-2-(methylsulfonyl)pyrimidin-4-yl)-3-methylmorpholine (intermediate 9) followed by purification by flash chromatography (0-80% Petroleum Ether/EtOAc) to yield a green gum (320 mg, 20%).

LCMS (method B), (M+H+) 386, Rt=2.55 min.

Intermediate 11

1-cyclopropyl-3-(3-fluoro-4-(4,4,5,5-tetramethyl-1,3,2-dioxaborolan-2-yl)phenyl)urea

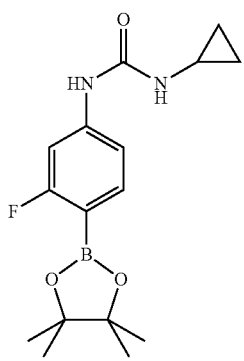 [SMILES: CC1(C)OB(c2ccc(NC(=O)NC3CC3)cc2F)OC1(C)C]

To a stirred solution of 4-amino-2-fluorophenyl boronic acid pinacol ester (1.185 g, 5.0 mmol) in DCM (17 ml) was added isocyanato cyclopropane (830 mg, 10.0 mmol) and stirred overnight at 37° C. The reaction mixture was washed with water (20 mL), passed through a PTFE hydrophobic frit and the solvent removed in vacuo to yield a white solid (1.56 g) used without further purification.

LCMS (method B), (M+H+) 321, Rt=2.50 min.

Intermediate 12 phenyl(3-fluoro-4-(4,4,5,5-tetramethyl-1,3,2-dioxaborolan-2-yl)phenyl)carbamate

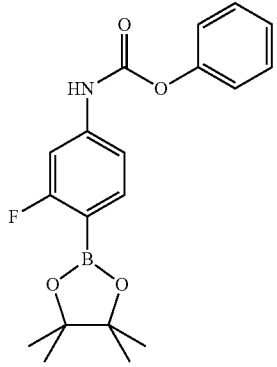 [SMILES: CC1(C)OB(c2ccc(NC(=O)Oc3ccccc3)cc2F)OC1(C)C]

To a stirred solution of 4-amino-2-fluorophenyl boronic acid pinacol ester (3.0 g, 12.7 mmol) in THF (10 ml) was added sodium hydrogen carbonate (1.6 g, 19.0 mmol) followed by phenyl chloroformate (1.9 ml, 15.2 mmol) and stirred overnight at room temperature. The reaction mixture was partitioned between DCM and water, the organic phase recovered, dried over $Mg_2SO_4$ and filtered before being concentrated in-vacuo to afford a white solid (4.95 g, quantitative).

LCMS (method B), (M+H+) 357, Rt=3.08 min.

Intermediate 13

1-(3-fluoro-4-(4,4,5,5-tetramethyl-1,3,2-dioxaborolan-2-yl)phenyl)-3-(2-hydroxyethyl)urea

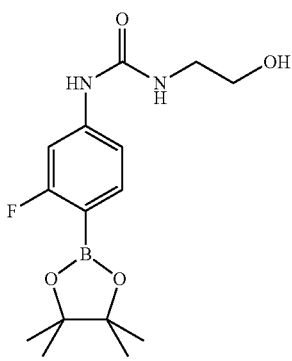 [SMILES: CC1(C)OB(c2ccc(NC(=O)NCCO)cc2F)OC1(C)C]

To a stirred solution of phenyl(3-fluoro-4-(4,4,5,5-tetramethyl-1,3,2-dioxaborolan-2-yl)phenyl)carbamate (intermediate 12) (1.0 g, 2.8 mmol) in DMF (2 mL) was added triethylamine (1.3 mL, 9.0 mmol) followed by ethanolamine (0.84 mL, 14.0 mmol) and stirred at 50° C. for 2 hours. The reaction mixture was concentrated in-vacuo to afford a white solid (1.84 g, quantitative).

LCMS (method B), (M+H+) 325, Rt=2.21 min.

Intermediate 14

1-(3-fluoro-4-(4,4,5,5-tetramethyl-1,3,2-dioxaborolan-2-yl)phenyl)-3-(2-fluoroethyl)urea

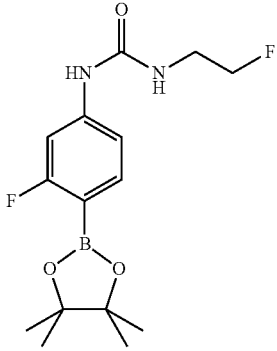 [SMILES: CC1(C)OB(c2ccc(NC(=O)NCCF)cc2F)OC1(C)C]

Method as described for intermediate 13 using 2-fluoroethylamine to afford a white solid (5.73 g, quantitative).
LCMS (method B), (M+H+) 327, Rt=2.49 min.

Intermediate 15

(S)-4-(4-chloropyrimidin-2-yl)-3-methylmorpholine

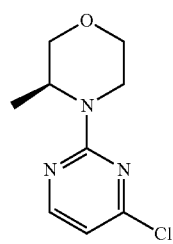

Method as described for intermediate 3 isolating the minor product to afford a light yellow gum (240 mg, 4%).
LCMS (method B), (M+H+) 214, Rt=2.39 min.

Intermediate 16

(S)-4-(4-chloro-6-(5-fluoro-2-(methylsulfonyl)phenyl)pyrimidin-2-yl)-3-methylmorpholine

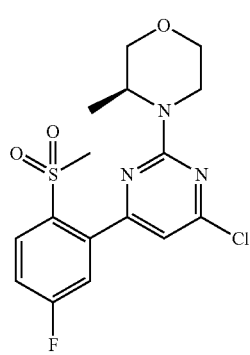 [SMILES: C[C@H]1COCCN1c1nc(Cl)cc(-c2cc(F)ccc2S(C)(=O)=O)n1]

Method as described for example 2 using (S)-4-(4,6-dichloropyrimidin-2-yl)-3-methylmorpholine (intermediate 1B) to afford a yellow solid (510 mg, 33%).
LCMS (method B), (M+H+) 386, Rt=2.78 min.

Intermediate 17 phenyl(4-(4,4,5,5-tetramethyl-1,3,2-dioxaborolan-2-yl)phenyl)carbamate

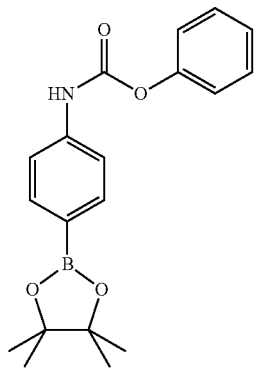 [SMILES: CC1(C)OB(c2ccc(NC(=O)Oc3ccccc3)cc2)OC1(C)C]

Method as described for intermediate 12 using 4-(4,4,5,5-tetramethyl-1,3,2-dioxaborolan-2-yl)aniline to afford a white solid (4.71 g) used without further purification.
LCMS (method B), (M+H+) 307, Rt=2.17 min.

Intermediate 18

1-(2-hydroxyethyl)-3-(4-(4,4,5,5-tetramethyl-1,3,2-dioxaborolan-2-yl)phenyl)urea

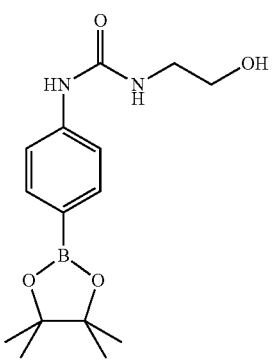 [SMILES: CC1(C)OB(c2ccc(NC(=O)NCCO)cc2)OC1(C)C]

Method as described for intermediate 13 using phenyl(4-(4,4,5,5-tetramethyl-1,3,2-dioxaborolan-2-yl)phenyl)carbamate (intermediate 17) and ethanolamine to afford a yellow gum (7.6 g) used without further purification.
LCMS (method B), (M+H+) 307, Rt=2.17 min.

Intermediate 19

1-(2-fluoroethyl)-3-(4-(4,4,5,5-tetramethyl-1,3,2-dioxaborolan-2-yl)phenyl)urea

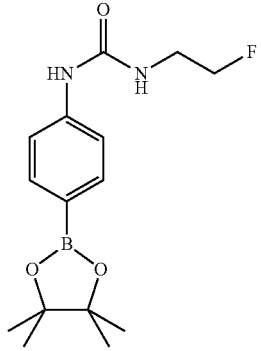 [SMILES: CC1(C)OB(c2ccc(NC(=O)NCCF)cc2)OC1(C)C]

Method as described for intermediate 13 using phenyl(4-(4,4,5,5-tetramethyl-1,3,2-dioxaborolan-2-yl)phenyl)carbamate (intermediate 17) and 2-fluoroethylamine to afford a pink wax (3.8 g) used without further purification.
LCMS (method B), (M+H+) 309, Rt=2.44 min.

Intermediate 20

1-(2,2-difluoroethyl)-3-(4-(4,4,5,5-tetramethyl-1,3,2-dioxaborolan-2-yl)phenyl)urea

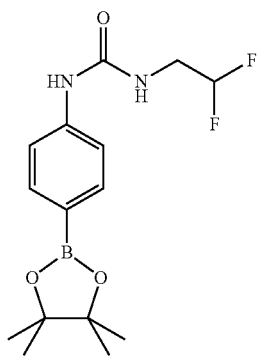 [SMILES: CC1(C)OB(c2ccc(NC(=O)NCC(F)F)cc2)OC1(C)C]

Method as described for intermediate 13 using phenyl(4-(4,4,5,5-tetramethyl-1,3,2-dioxaborolan-2-yl)phenyl)carbamate (intermediate 17) and 2,2-difluoroethylamine to afford a pink oil (505 mg, 48%).
LCMS (method B), (M+H+) 327, Rt=2.55 min.

Intermediate 21

(S)-4-(2-chloro-6-(pyridin-2-yl)pyrimidin-4-yl)-3-methylmorpholine

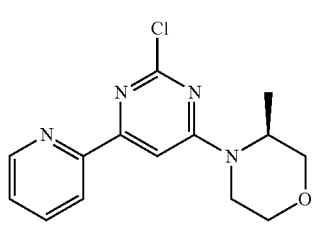 [SMILES: C[C@H]1COCCN1c1cc(-c2ccccn2)nc(Cl)n1]

Method as described for intermediate 3 using 2,4-dichloro-6-pyridine-2-ylpyrimidine and 3S-methlymorpholine to afford a pink solid (380 mg, 74%).
LCMS (method B), (M+H+) 291, Rt=2.49 min.

Intermediate 22

(S)-1-(4-(6-chloro-2-(3-methylmorpholino)pyrimidin-4-yl)phenyl)-3-cyclopropylurea

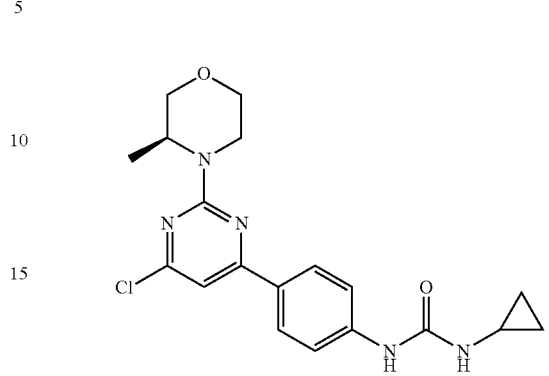

Method as described for intermediate 5 using (S)-4-(4,6-dichloropyrimidin-2-yl)-3-methylmorpholine (intermediate 1B) and 4-(3-cyclopropylureido)phenyl boronic acid pinacol ester to afford an orange solid (400 mg, 31%).
LCMS (method B), (M+H+) 388, Rt=2.75 min.

Intermediate 23

(S)-1-cyclopropyl-3-(4-(2-(3-methylmorpholino)-6-(2-(methylthio)pyridin-3-yl)pyrimidin-4-yl)phenyl)urea

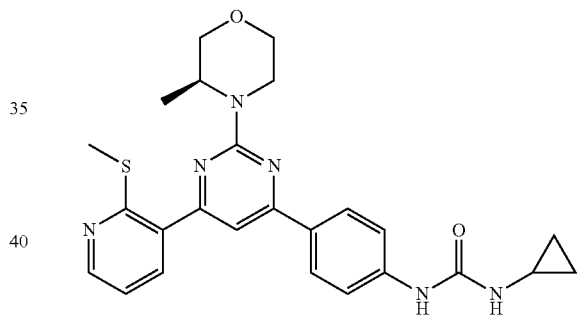

Method as described for intermediate 5 using (S)-1-(4-(6-chloro-2-(3-methylmorpholino)pyrimidin-4-yl)phenyl)-3-cyclopropylurea (intermediate 22) and 2-(methylsulfanyl)pyridine-3-boronic acid pinacol ester to afford a yellow solid (160 mg, 65%).
LCMS (method B), (M+H+) 477, Rt=2.87 min.

Intermediate 24

3-(2-chloropyrimidin-4-yl)-8-oxa-3-azabicyclo[3.2.1]octane

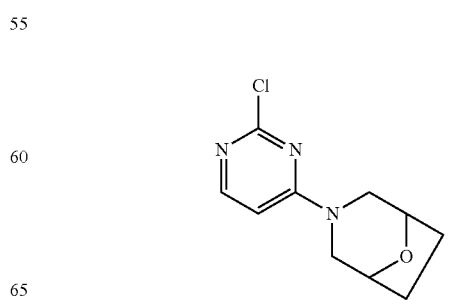

Method as described for intermediate 3 using 8-oxa-3-azabicyclo[3,2,1]octane hydrochloride. Purified using flash chromatography (70-100% EtOAc in Petroleum Ether 40-60 over 20 min) to yield a white powder. (710 mg, 67%)
LCMS (method B), (M+H+) 225, Rt=1.83 min.

Intermediate 25

2-chloro-4-(4-nitrophenyl)pyrimidine

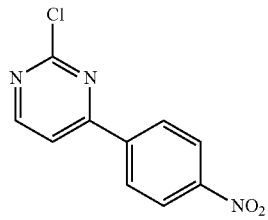 [SMILES: O=[N+]([O-])c1ccc(-c2ccnc(Cl)n2)cc1]

Method as described for intermediate 5 using 4,4,5,5-tetramethyl-2-(4-nitrophenyl)-1,3,2-dioxaborolane and 2,4-dichloropyrimidine. The mixture was purified using flash chromatography (0-100% EtOAc in petroleum ether 40-60) to afford the title compound (1.45 g, 53%)
LCMS (method B), (M+H+) 236, Rt=2.50 min.

Intermediate 26

4-(2-(8-oxa-3-azabicyclo[3.2.1]octan-3-yl)pyrimidin-4-yl)aniline

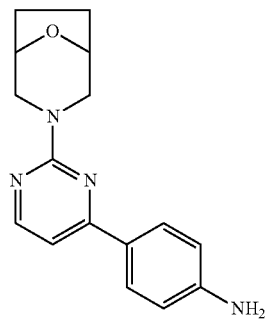 [SMILES: Nc1ccc(-c2ccnc(N3CC4CCC(C3)O4)n2)cc1]

Step (i)
2-chloro-4-(4-nitrophenyl)pyrimidine (intermediate 25), 8-oxa-3-azabicyclo[3,2,1]octane hydrochloride (149 mg, 3.56 mmol) and triethylamine (618 µl, 4.46 mmol) were combined in DMF (5 ml) and stirred at 50° C. overnight. The mixture was then diluted using EtOAc, washed with brine, dried over magnesium sulfate, filtered and the solvent removed in vacuo. (817 mg, 88%)
LCMS (method B), (M+H+) 301.1, Rt=2.78 min.
Step (ii)
The above crude mixture was dissolved in EtOH (20 ml) and Pd/C (10%) (82 mg) was added and stirred at room temperature under hydrogen overnight. The reaction mixture was filtered through a celite545 cake and washed with methanol. The mixture was concentrated in vacuo yielding the title compound as a brown solid. (699 mg, 95%)
LCMS (method B), (M+H+) 283, Rt=1.66 min.

Intermediate 27 phenyl(4-(2-(8-oxa-3-azabicyclo[3.2.1]octan-3-yl)pyrimidin-4-yl)phenyl)carbamate

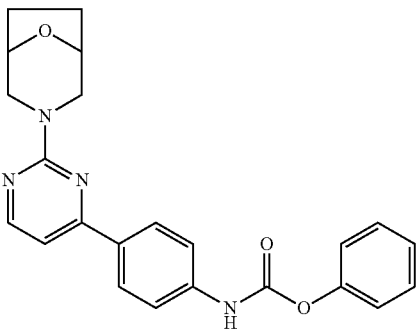 [SMILES: O=C(Nc1ccc(-c2ccnc(N3CC4CCC(C3)O4)n2)cc1)Oc1ccccc1]

4-(2-(8-oxa-3-azabicyclo[3.2.1]octan-3-yl)pyrimidin-4-yl)aniline (intermediate 26) (471 mg, 1.51 mmol) was stirred with sodium hydrogen carbonate (190 mg, 2.26 mmol) and phenyl chloroformate (285 µl, 2.26 mmol) in DCM (5 ml) at room temperature overnight. The reaction mixture was diluted with EtOAc, washed with brine and the organics were concentrated in vacuo. The resulting yellow solid was purified by flash chromatography (0-100% EtOAc:Petroleum Ether 40-60) to afford the title compound. (60 mg, 10%)
LCMS (method B), (M+H+) 403.2, Rt=2.70 min.

Intermediate 28

(S)-4-(2-(3-methylmorpholino)pyrimidin-4-yl)aniline

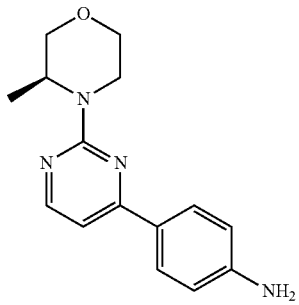 [SMILES: C[C@H]1COCCN1c1nccc(-c2ccc(N)cc2)n1]

Method as described for intermediate 26 using (S)-3-methylmorpholine. (699 mg, 95%).
LCMS (method B), (M+H+) 271, Rt=1.67 min.

Intermediate 29

(S)-phenyl(4-(2-(3-methylmorpholino)pyrimidin-4-yl)phenyl)carbamate

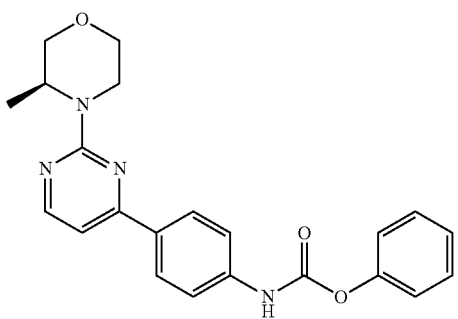 [SMILES: C[C@H]1COCCN1c1nccc(-c2ccc(NC(=O)Oc3ccccc3)cc2)n1]

Method as described for intermediate 27 using (S)-4-(2-(3-methylmorpholino)pyrimidin-4-yl)aniline (intermediate 28). Yielding without chromatography (450 mg) used without further purification.

LCMS (method B), (M+H+) 391, Rt=2.77 min.

Intermediate 30

1-(pyridin-4-yl)-3-(4-(4,4,5,5-tetramethyl-1,3,2-dioxaborolan-2-yl)phenyl)urea

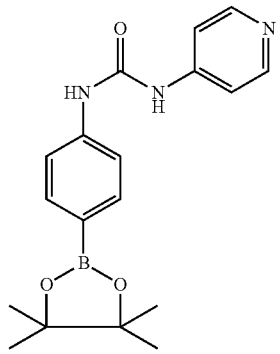 [SMILES: CC1(C)OB(c2ccc(NC(=O)Nc3ccncc3)cc2)OC1(C)C]

2-(4-isocyanatophenyl)-4,4,5,5-tetramethyl-1,3,2-dioxaborolane (1 g, 4.1 mmol) was dissolved in dry THF and stirred with pyridin-4-amine (460 mg, 4.9 mmol) and triethylamine (1.13 ml, 8.2 mmol) at 60° C. for 3 hours. The mixture was cooled and then purified by flash chromatography (0-100% EtOAc in Petroleum ether 40-60, followed by 0-10% MeOH in EtOAc) to afford the title compound. (875 mg, 63%) uPLC (method D), (M+H+) 340, Rt=0.89 mins Intermediate 31

(S)-4-(6-(5-fluoro-2-(methylsulfonyl)phenyl)-2-(3-methylmorpholino)pyrimidin-4-yl)aniline

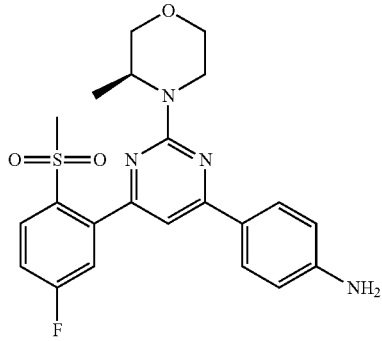 [SMILES: C[C@H]1COCCN1c1nc(-c2ccc(N)cc2)cc(-c2cc(F)ccc2S(C)(=O)=O)n1]

Method as described for intermediate 5 using (S)-4-(4-chloro-6-(5-fluoro-2-(methylsulfonyl)phenyl)pyrimidin-2-yl)-3-methylmorpholine (intermediate 16) (451 mg, 1.17 mmol) and 4-(4,4,5,5-tetramethyl-1,3,2-dioxaborolan-2-yl) aniline (256 mg, 1.17 mmol). The mixture was purified using flash chromatography (30-100% EtOAc in petroleum ether 40-60) to afford the title compound (298 mg, 58%)

LCMS (method B), (M+H+) 443, Rt=2.59 min.

Intermediate 32

(S)-phenyl(4-(6-(5-fluoro-2-(methylsulfonyl)phenyl)-2-(3-methylmorpholino)pyrimidin-4-yl)phenyl) carbamate

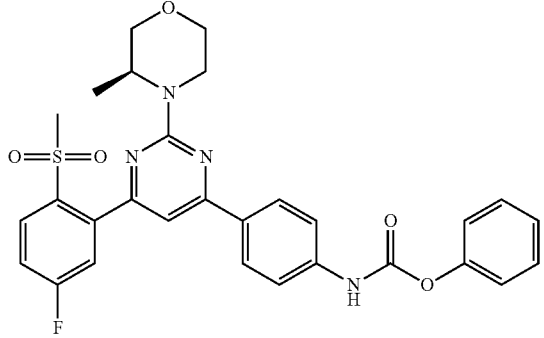 [SMILES: C[C@H]1COCCN1c1nc(-c2ccc(NC(=O)Oc3ccccc3)cc2)cc(-c2cc(F)ccc2S(C)(=O)=O)n1]

Method as described for intermediate 27 using (S)-4-(6-(5-fluoro-2-(methylsulfonyl)phenyl)-2-(3-methylmorpholino)pyrimidin-4-yl)aniline (intermediate 31) to afford the title compound as a yellow solid. (1.24 g, 90%)

LCMS (method B), (M+H+) 563.2, Rt=3.11 min

Intermediate 33

(S)-4-(4-(5-fluoro-2-(methylsulfonyl)phenyl)-6-(3-methylmorpholino)pyrimidin-2-yl)aniline

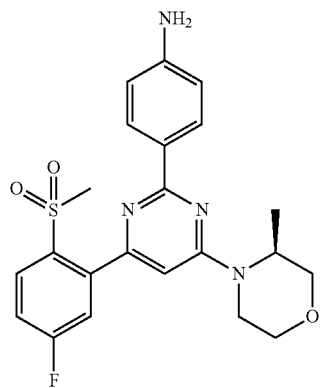 [SMILES: C[C@H]1COCCN1c1cc(-c2cc(F)ccc2S(C)(=O)=O)nc(-c2ccc(N)cc2)n1]

(S)-4-(2-chloro-6-(5-fluoro-2-(methylsulfonyl)phenyl) pyrimidin-4-yl)-3-methylmorpholine (intermediate 10) (350 mg, 0.91 mmol), 4-(4,4,5,5-tetramethyl-1,3,2-dioxaborolan-2-yl)aniline (239 mg, 1.09 mmol), Pd(PPh$_3$)$_2$Cl$_2$.DCM (37 mg, 0.05 mmol) and Na$_2$CO$_3$ (145 mg, 1.36 mmol) were dissolved in a mixture of DME:H$_2$O (4:1) and stirred at 120° C. under microwave for 30 mins. The reaction mixture was partitioned between H$_2$O and DCM. The organic layer was recovered, dried over MgSO$_4$, filtered and the solvent removed in vacuo to yield the title compound as a brown solid (128 mg, 0.29 mmol, 32% yield).

$^1$H NMR (d$_6$-DMSO) δ 8.16-8.10 (m, 1H), 7.99 (d, 2H), 7.62-7.54 (m, 1H), 7.54-7.49 (dd, 1H), 6.69 (s, 1H), 7.58 (d, 2H), 4.58-4.47 (br s, 1H), 4.30-4.21 (br s, 1H), 4.12-4.04 (q,

1H), 4.02-3.93 (dd, 1H), 3.75 (d, 1H), 3.68-3.60 (dd, 1H), 3.49 (s, 3H), 3.23-3.18 (dd, 1H), 3.17 (d, 2H), 1.24 (d, 3H).
LCMS (method A) (M+H+) 443; Rt=7.08 min Intermediate 34

(S)-phenyl(4-(4-(5-fluoro-2-(methylsulfonyl)phenyl)-6-(3-methylmorpholino)pyrimidin-2-yl)phenyl) carbamate

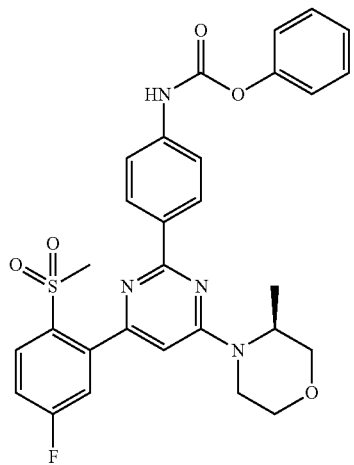 [SMILES: C[C@H]1COCCN1c1cc(-c2cc(F)ccc2S(C)(=O)=O)nc(-c2ccc(NC(=O)Oc3ccccc3)cc2)n1]

Method as intermediate 27 using (S)-4-(4-(5-fluoro-2-(methylsulfonyl)phenyl)-6-(3-methylmorpholino)pyrimidin-2-yl)aniline (intermediate 33) as starting material. The reaction mixture was partitioned between H$_2$O and DCM. The organic layer was recovered, dried with PTFE hydrophobic frit and the solvent removed in vacuo to yield the title compound (121 mg, 0.22 mmol, quantitative yield).
LCMS (method B) (M+H+) 563; Rt=2.97 min.

Example 1

1-cyclopropyl-3-(4-(2-morpholino-6-(pyridin-3-yl)pyrimidin-4-yl)phenyl)urea

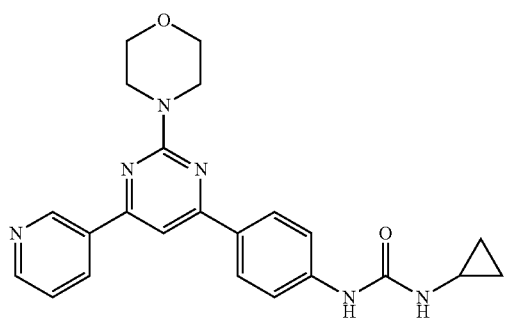 [SMILES: O=C(Nc1ccc(-c2cc(-c3cccnc3)nc(N3CCOCC3)n2)cc1)NC1CC1]

4-(4,6-dichloropyrimidin-2-yl)morpholine (100 mg 0.43 mmol), pyridine-3-boronic acid (49 mg, 0.4 mmol), Cs$_2$CO$_3$ (280 mg, 0.86 mmol) and Pd(PPh$_3$)$_2$Cl$_2$ (20 mg, 0.025 mmol) were combined in dioxane (3 ml) and water (1 ml). The reaction mixture was then heated by microwave at 120° C. for 20 min. Without purification (4-(3-cyclopropylureido)phenyl)boronic acid pinacol ester (130 mg, 0.43 mmol), Cs$_2$CO$_3$ (280 mg, 0.86 mmol) and Pd(PPh$_3$)$_2$Cl$_2$ (20 mg, 0.025 mmol) were added and the reaction mixture was then heated by microwave at 120° C. for a further 20 min. The reaction mixture was partitioned between EtOAc and water. The organic layer was passed through a PTFE hydrophobic frit and the solvent removed in vacuo. Residual solid was triturated to give crude prodluect which was further purifed by prep LC/MS (low pH) to yield (9 mg, 5%).
$^1$H NMR (d$_6$-DMSO) 9.45 (s, 1H), 8.72 (d, 1H), 8.65 (s, 1H), 8.61 (d, 1H), 8.22 (d, 2H), 7.87 (s, 1H), 7.58-7.55 (m, 3H), 6.51 (br s, 1H), 3.93-3.86 (m, 4H) 3.76-3.71 (m, 4H), 2.58-2.52 (m, 1H), 0.67-0.62 (m, 2H), 0.44-0.40 (m, 2H);
LCMS (method B), (M+H+) 417, Rt=2.24 min.

Example 2

(S)-1-ethyl-3-(4-(6-(5-fluoro-2-(methylsulfonyl)phenyl)-2-(3-methylmorpholino)pyrimidin-4-yl)phenyl)urea

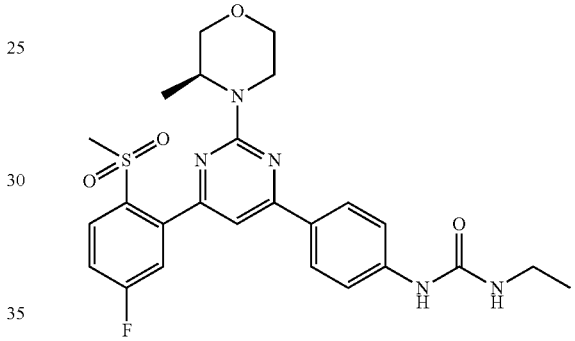

Step (i)
Sodium hydrogen carbonate (1.59 g, 18.87 mmol) and sodium sulfite (1.59 g, 12.58 mmol) were heated in water (10 mL) at 70° C. for 5 min. A mixture of 2-bromo-4-fluorobenzene sulfonyl chloride (1.72 g, 6.29 mmol) in dioxane (15 mL) was added to the base solution and stirred at 70° C. overnight. The solvents were removed in vacuo, DMF (15 mL) and methyl iodide (0.43 mL, 6.85 mmol) were added and reaction mixture stirred at 40° C. overnight. The reaction mixture was concentrated in vacuo, EtOAc (10 ml) added, washed with water (90 ml) and concentrated in vacuo to leave a colourless oil. The resulting oil was purified by flash chromatography (0-10% EtOAc in petroleum ether (40:60) followed by 100% MeOH) to afford 2-bromo-4-fluoro-1-(methylsulfonyl)benzene as an orange oil (1.3 g, 81%).
LCMS (method B), (M+H+) 253/255, Rt=2.12 min.
Step (ii)
2-bromo-4-fluoro-1-(methylsulfonyl)benzene (117 mg, 0.46 mmol), bis(pinacolato)diboron (123 mg, 0.48 mmol), potassium acetate (135 mg, 1.38 mmol) and bis(diphenylphosphino)-ferrocenedichloropalladium(II)-DCM-complex (19 mg, 0.02 mmol) in dioxane (1.5 mL) were irradiated in a Biotage microwave for 60 min at 120° C. (S)-1-(4-(6-chloro-2-(3-methylmorpholino)pyrimidin-4-yl)phenyl)-3-ethylurea (Intermediate 2) (173 mg, 0.46 mmol), sodium carbonate solution (2M aqueous solution, 0.92 mL, 1.84 mmol) and EtOH (0.3 mL) were added and reaction mixture further irradiated in a Biotage microwave for 60 min at 100° C. The reaction mixture was concentrated in vacuo, and the residue suspended in EtOAc (70 mL), washed with water (2×40 mL) followed by brine (40 mL), dried with sodium sulfate and concentrated in vacuo to leave an orange oil. The oil was purified by flash chromatography (0-20% EtOAc in DCM over 60 min) to yield the title compound as an orange solid (80 mg, 34%).

$^1$H NMR (d$_6$-DMSO) 8.77 (s, 1H), 8.16-8.13 (m, 1H), 8.13 (d, 1H), 7.65-7.60 (m, 1H), 7.58-7.54 (m, 1H), 7.52 (d, 2H), 7.30 (s, 1H), 6.23 (t, 1H), 4.76-4.68 (m, 1H), 4.37 (d, 1H), 3.94 (d, 1H), 3.73 (d, 1H), 3.64 (d, 1H), 3.48 (t, 1H), 3.22 (t, 1H), 3.16-3.08 (m, 2H), 1.25 (d, 3H), 1.06 (t, 3H);

LCMS (method A), (M+H+) 514, Rt=10.28 min.

Example 3

(S)-1-cyclopropyl-3-(4-(4-(3-methylmorpholino)-6-(pyridin-3-yl)pyrimidin-2-yl)phenyl)urea

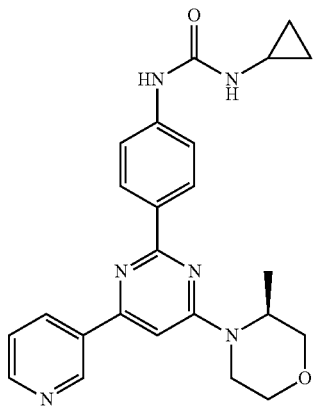 [SMILES: C[C@H]1COCCN1c1cc(-c2cccnc2)nc(-c2ccc(NC(=O)NC3CC3)cc2)n1]

Step (i)

A mixture of (S)-4-(2,6-dichloropyrimidin-4-yl)-3-methylmorpholine (Intermediate 1A) (150 mg, 0.6 mmol), pyridin-3-yl boronic acid (67 mg, 0.55 mmol), bis(triphenylphosphene)palladium(II) dichloride (19 mg, 0.03 mmol) and sodium carbonate (2M aq solution, 1.64 mL) in DME/H$_2$O/EtOH (7:3:1, 1 mL) was heated in the microwave at 80° C. for 20 min. The mixture was then diluted with EtOAc, washed with water and the organics were concentrated in vacuo.

Step (ii)

The above crude mixture was dissolved in DME/H$_2$O/EtOH (7:3:1, 1 mL) and bis(triphenylphosphene)palladium(II) dichloride (5 mg, 0.007 mmol), sodium carbonate (2M aq solution, 0.42 mL) and 4-(3-cyclopropylureido)phenyl boronic acid pinacol ester (47 mg, 0.154 mmol) were added. The mixture was heated to 100° C. for 3 h then diluted with EtOAc, washed with water and the organics concentrated in vacuo. The resulting oil was purified by flash column chromatography (0-10% MeOH:DCM) to afford the title compound (7.1 mg, 12%).

$^1$H NMR (d$_6$-DMSO) δ 9.44 (d, 1H), 8.70 (dd, 1H), 8.63 (dd, 1H), 8.60 (s, 1H), 8.35 (d, 2H), 7.56-7.58 (m, 1H), 7.54 (d, 2H), 7.28 (s, 1H), 6.47 (d, 1H), 4.72 (br s, 1H), 4.37 (br d, 1H), 4.01 (dd, 1H), 3.79 (d, 1H), 3.68 (dd, 1H), 3.53 (dt, 1H), 3.22-3.30 (m, 1H), 2.54-2.61 (m, 1H), 1.27 (d, 3H), 0.63-0.68 (m, 2H), 0.41-0.43 (m, 2H);

LCMS (method A), (M+H+) 431, Rt=7.17 min.

Example 4

(S)-1-cyclopropyl-3-(4-(2-(3-methylmorpholino)-6-(2-(methylsulfonyl)phenyl)pyrimidin-4-yl)phenyl)urea

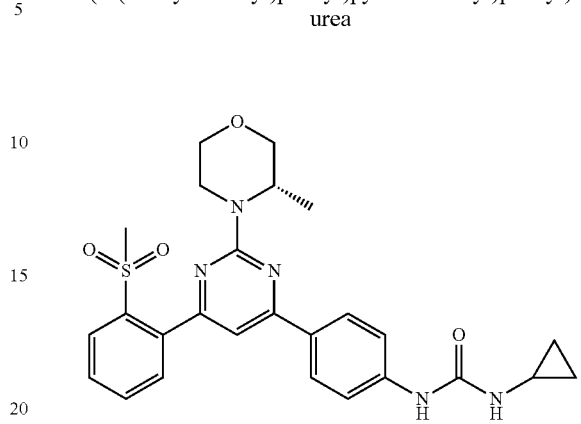

Method as described for Example 3 using (S)-4-(4,6-dichloropyrimidin-2-yl)-3-methylmorpholine (Intermediate 1B), and (2-(methylsulfonyl)phenyl)boronic acid.

$^1$H NMR (d$_6$-DMSO) 8.82 (s, 1H), 8.12 (d, 2H), 8.08 (d, 1H), 7.85 (dd, 1H), 7.77 (dd, 1H), 7.60 (d, 1H), 7.54 (d, 2H), 7.27 (s, 1H), 6.27 (d, 1H), 4.36 (d, 1H), 4.03 (q, 1H), 3.95-3.90 (m, 1H), 3.75-3.59 (m, 2H), 3.51-3.15 (m, 5H), 2.58-2.50 (m, 4H), 2.50 (s, 3H);

LCMS (method A), (M+H+) 508, Rt=2.69 min.

Example 5

(S)-1-cyclopropyl-3-(4-(4-(3-methylmorpholino)-6-(3-(methylsulfonyl)phenyl)pyrimidin-2-yl)phenyl)urea

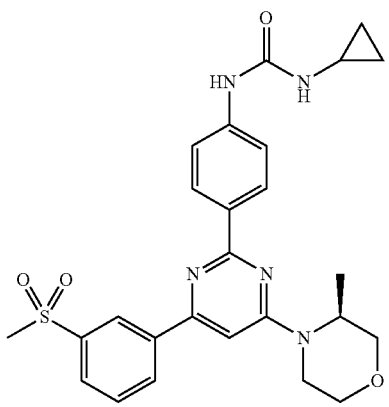 [SMILES: C[C@H]1COCCN1c1cc(-c2cccc(S(C)(=O)=O)c2)nc(-c2ccc(NC(=O)NC3CC3)cc2)n1]

Method as described for Example 3 using (3-(methylsulfonyl)phenyl)boronic acid.

$^1$H NMR (d$_6$-DMSO) δ 8.76 (t, 1H), 8.64 (dt, 1H), 8.62 (s, 1H), 8.35 (d, 2H), 8.07 (dt, 1H), 7.83 (t, 1H), 7.55 (d, 2H), 7.31 (s, 1H), 6.49 (d, 1H), 4.74 (br s, 1H), 4.37 (br d, 1H), 4.01 (dd, 1H), 3.81 (d, 1H), 3.68 (dd, 1H), 3.53 (dt, 1H), 3.34 (s, 3H), 3.27 (dt, 1H), 2.52-2.60 (m, 1H), 1.27 (d, 3H), 0.62-0.68 (m, 2H), 0.40-0.45 (m, 2H);

LCMS (method A), (M+H+) 508, Rt=7.83 min.

Example 6

(S)-1-cyclopropyl-3-(4-(4-(3-methylmorpholino)-6-(2-(methylsulfonyl)phenyl)pyrimidin-2-yl)phenyl)urea

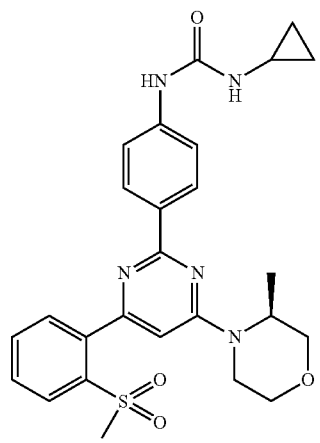 [SMILES: C[C@H]1COCCN1c1cc(-c2ccccc2S(C)(=O)=O)nc(-c2ccc(NC(=O)NC3CC3)cc2)n1]

Method as described for Example 3 using (2-(methylsulfonyl)phenyl)boronic acid.

$^1$H NMR (d$_6$-DMSO) δ 8.68 (s, 1H), 8.17 (d, 2H), 8.09 (dd, 1H), 7.85 (dt, 1H), 7.76 (dt, 1H), 7.63 (dd, 1H), 7.50 (d, 2H), 6.76 (s, 1H), 6.58 (d, 1H), 4.56 (br s, 2H), 4.30 (br s, 2H), 3.80 (dd, 1H), 3.77 (d, 1H), 3.66 (d, 1H), 3.48-3.55 (m, 1H), 3.49 (s, 3H), 2.52-2.58 (m, 1H), 1.25 (d, 3H), 0.60-0.67 (m, 2H), 0.38-0.43 (m, 2H);

LCMS (method A), (M+H+) 508, Rt=8.79 min.

Example 7

(S)-1-cyclopropyl-3-(4-(2-(3-methylmorpholino)-6-(pyridin-3-yl)pyrimidin-4-yl)phenyl)

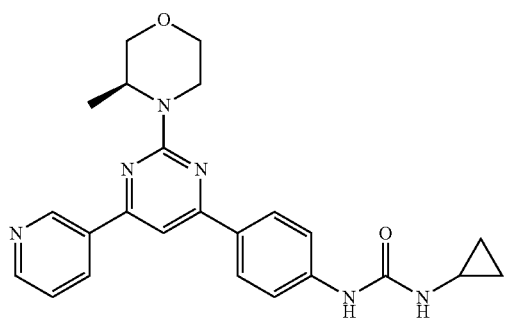 [SMILES: C[C@H]1COCCN1c1nc(-c2ccc(NC(=O)NC3CC3)cc2)cc(-c2cccnc2)n1]

Method as described for Example 1 using (S)-4-(4,6-dichloropyrimidin-2-yl)-3-methylmorpholine (Intermediate 1B) to afford the title compound (56 mg, 32%).

$^1$H NMR (d$_6$-DMSO) 9.44 (s, 1H), 8.71 (d, 1H), 8.66 (s, 1H), 8.61 (d, 1H), 8.22 (d, 2H), 7.85 (s, 1H), 7.58-7.55 (m, 3H), 6.51 (br s, 1H), 4.90-4.83 (m, 1H), 4.52 (br d, 1H), 3.98 (br d, 1H), 3.78 (d, 1H), 3.66 (br dd, 1H), 3.50 (br t, 1H), 3.26 (br t, 1H), 2.58-2.52 (m, 1H), 1.26 (d, 3H), 0.67-0.62 (m, 2H), 0.44-0.40 (m, 2H);

LCMS (method B), (M+H+) 431, Rt=2.37 min

Example 8

(S)-1-(4-(6-(2-cyanophenyl)-2-(3-methylmorpholino)pyrimidin-4-yl)phenyl)-3-ethylurea

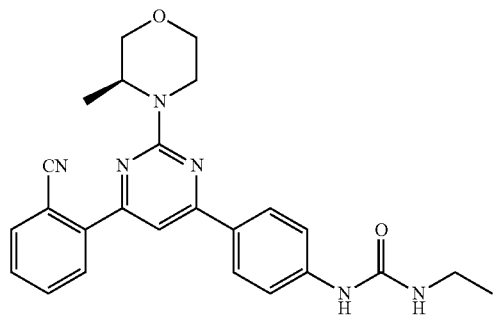 [SMILES: CCNC(=O)Nc1ccc(-c2cc(-c3ccccc3C#N)nc(N3CCOC[C@@H]3C)n2)cc1]

(S)-1-(4-(6-chloro-2-(3-methylmorpholino)pyrimidin-4-yl)phenyl)-3-ethylurea (Intermediate 2) (90 mg, 0.24 mmol), 2-cyanobenzeneboronic acid (43 mg, 0.29 mmol), cesium carbonate (235 mg, 0.72 mmol) and bis(diphenylphosphino)-ferrocenedichloropalladium(II)-DCM-complex (10 mg, 0.01 mmol) in dioxane/water (1:3, 1 mL) were irradiated in a Biotage microwave for 40 min at 110° C. The reaction mixture was concentrated in vacuo, and the residue dissolved in DMSO, filtered and purified by prep HPLC (low pH) to afford a green solid (44 mg, 41%).

$^1$H NMR (d$_6$-DMSO) 8.81 (s, 1H), 8.17-8.15 (m, 3H), 8.00 (d, 1H), 7.85 (dd, 1H), 7.71 (dd, 1H), 7.63 (s, 1H), 7.55 (d, 1H), 6.24 (t, 1H), 4.93-4.90 (m, 1H), 4.56 (d, 1H), 3.97 (d, 1H), 3.76 (d, 1H), 3.63 (d, 1H), 3.48 (t, 1H), 3.28 (t, 1H), 3.19-3.09 (m, 2H), 1.27 (d, 3H), 1.07 (t, 3H);

LCMS (method A), (M+H+) 443, Rt=10.91 min.

Example 9

(S)—N-(2-(6-(4-(3-ethylureido)phenyl)-2-(3-methylmorpholino)pyrimidin-4-yl)phenyl)methanesulfonamide

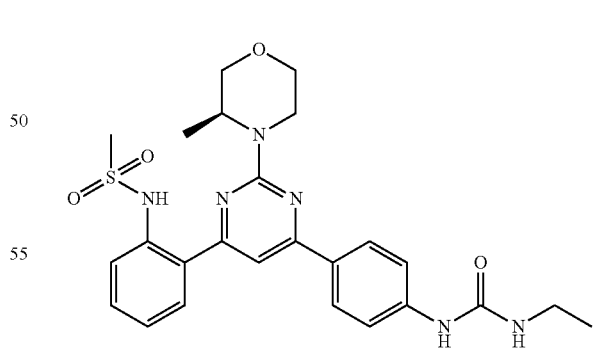

Method as described for Example 8 using (2-methylsulphonylamino)benzeneboronic acid. The reaction mixture was concentrated in vacuo, and the residue dissolved in DMSO, filtered and purified by prep HPLC (low pH) to afford a pale yellow solid (67 mg, 55%).

$^1$H NMR (d$_6$-DMSO) 12.24 (s, 1H), 8.83 (s, 1H), 8.27-8.20 (m, 3H), 7.76 (s, 1H), 7.64 (d, 1H), 7.57-7.52 (m, 3H), 7.27

(dd, 1H), 6.24 (t, 1H), 4.69-4.68 (m, 1H), 4.74-4.63 (m, 1H), 4.40-4.27 (m, 1H), 3.98 (d, 1H), 3.77 (d, 1H), 3.67 (d, 1H), 3.52 (t, 1H), 3.31 (t, 1H), 3.16-3.06 (m, 5H), 1.27 (d, 3H), 1.07 (t, 3H);

LCMS (method A), (M+H+) 511, Rt=10.79 min.

Example 10

(S)—N-(2-(6-(4-(3-ethylureido)phenyl)-2-(3-methyl-morpholino)pyrimidin-4-yl)phenyl)acetamide

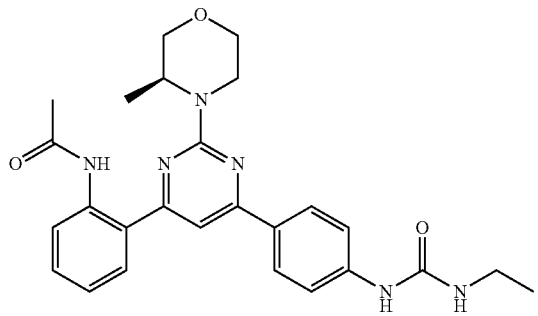 [SMILES: CCNC(=O)Nc1ccc(-c2cc(-c3ccccc3NC(C)=O)nc(N3CCOC[C@@H]3C)n2)cc1]

Method as described for Example 8 using (2-acetamidophenyl)boronic acid. The reaction mixture was concentrated in vacuo, and the residue dissolved in DMSO, filtered and purified by prep HPLC (low pH) to afford a pale yellow solid (56 mg, 49%).

$^1$H NMR (d$_6$-DMSO) 10.76 (s, 1H), 8.81 (s, 1H), 8.22-8.10 (m, 3H), 7.84 (d, 1H), 7.55 (d, 2H), 7.50-7.43 (m, 2H), 7.24 (dd, 1H), 6.25 (t, 1H), 4.85-4.76 (m, 1H), 4.41 (d, 1H), 4.20-4.08 (m, 2H), 3.98 (d, 1H), 3.78 (d, 1H), 3.65 (d, 1H), 3.50 (t, 1H), 3.30 (t, 1H), 3.17-3.10 (m, 2H), 2.06 (s, 3H), 1.27 (d, 3H), 1.07 (t, 3H);

LCMS (method A), (M+H+) 475, Rt=10.52 min.

Example 11

(S)-2-(6-(4-(3-ethylureido)phenyl)-2-(3-methylmorpholino)pyrimidin-4-yl)benzoic acid

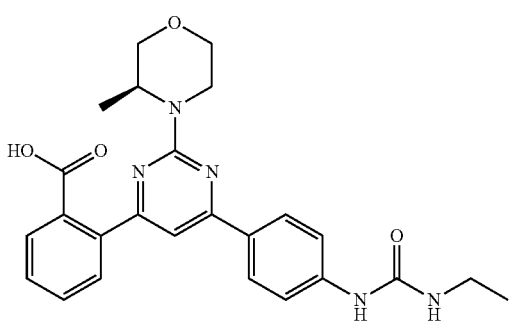 [SMILES: CCNC(=O)Nc1ccc(-c2cc(-c3ccccc3C(=O)O)nc(N3CCOC[C@@H]3C)n2)cc1]

Method as described for Example 8 using 2-boronobenzoic acid. The reaction mixture was concentrated in vacuo, and the residue dissolved in DMSO, filtered and purified by prep HPLC (low pH) to afford a green solid (56 mg, 49%).

$^1$H NMR (d$_6$-DMSO) 12.76 (s, 1H), 8.78 (s, 1H), 8.12 (d, 2H), 7.80 (d, 1H), 7.67-7.51 (m, 5H), 7.34 (s, 1H), 6.23 (t, 1H), 4.78-4.70 (m, 1H), 4.39 (d, 1H), 3.94 (d, 1H), 3.74 (d, 1H), 3.61 (d, 1H), 3.46 (t, 1H), 3.25-3.08 (m, 3H), 1.27 (d, 3H), 1.07 (t, 3H);

LCMS (method A), (M+H+) 462, Rt=9.38 min.

Example 12

(S)-2-(6-(4-(3-ethylureido)phenyl)-2-(3-methylmorpholino)pyrimidin-4-yl)benzamide

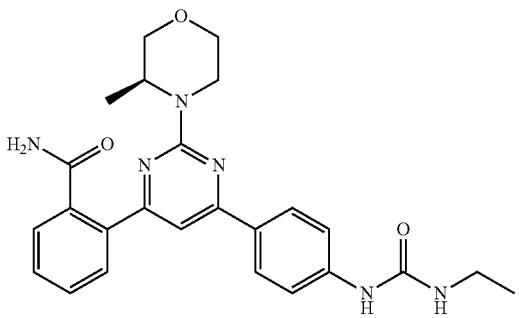 [SMILES: CCNC(=O)Nc1ccc(-c2cc(-c3ccccc3C(N)=O)nc(N3CCOC[C@@H]3C)n2)cc1]

Method as described for Example 8 using (2-carbamoylphenyl)boronic acid. The reaction mixture was concentrated in vacuo, and the residue dissolved in DMSO, filtered and purified by prep HPLC (low pH) to afford an off-white solid (29 mg, 26%).

$^1$H NMR (d$_6$-DMSO) 8.77 (s, 1H), 8.06 (d, 2H), 7.80 (d, 2H), 7.56-7.46 (m, 5H), 7.40 (s, 1H), 7.34 (br s, 1H), 6.24 (t, 1H), 4.80 (d, 1H), 4.46 (d, 1H), 3.94 (d, 1H), 3.74 (d, 1H), 3.61 (d, 1H), 3.46 (t, 1H), 3.22 (t, 1H), 3.15-3.02 (m, 2H), 1.27 (d, 3H), 1.07 (t, 3H);

LCMS (method A), (M+H+) 461, Rt=8.54 min.

Example 13

(S)-1-ethyl-3-(4-(2-(3-methylmorpholino)-6-(pyridin-4-yl)pyrimidin-4-yl)phenyl)urea

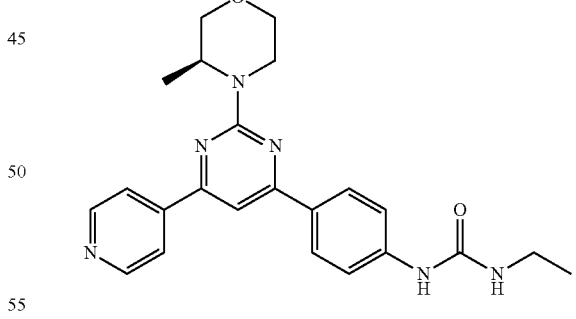

Method as described for Example 8 using pyridine-4-boronic acid. The reaction mixture was concentrated in vacuo, and the residue dissolved in DMSO, filtered and purified by prep HPLC (low pH) to afford a green solid (18 mg, 18%).

$^1$H NMR (d$_6$-DMSO) 8.81 (s, 1H), 8.75 (d, 2H), 8.22-8.20 (m 4H), 7.87 (s, 1H), 7.57 (d, 2H), 6.24 (t, 1H), 4.89 (d, 1H), 4.55 (d, 1H), 3.98 (d, 1H), 3.77 (d, 1H), 3.68 (d, 1H), 3.51 (t, 1H), 3.29 (t, 1H), 3.22-3.08 (m, 2H), 1.27 (d, 3H), 1.07 (t, 3H);

LCMS (method A), (M+H+) 419, Rt=7.89 min.

Example 14

(S)-2-(6-(4-(3-ethylureido)phenyl)-2-(3-methylmorpholino)pyrimidin-4-yl)-N,N-dimethylbenzenesulfonamide

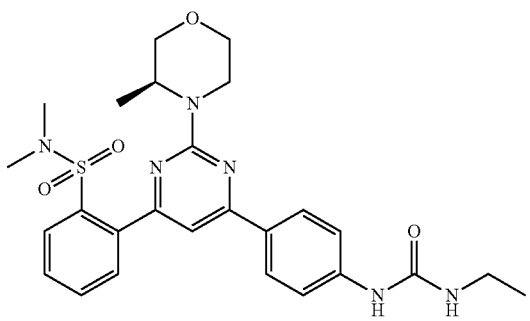 [SMILES: CCNC(=O)Nc1ccc(-c2cc(-c3ccccc3S(=O)(=O)N(C)C)nc(N3CCOC[C@@H]3C)n2)cc1]

Method as described for Example 8 using 2-(N,N-dimethylsulphamoyl)phenylboronic acid. The reaction mixture was concentrated in vacuo, and the residue dissolved in DMSO, filtered and purified by prep HPLC (low pH) to afford an off-white solid (31 mg, 27%).

$^1$H NMR (d$_6$-DMSO) 8.85 (s, 1H), 8.06 (d, 2H), 7.88 (d, 1H), 7.76 (dd, 1H), 7.70 (dd, 1H), 7.54 (d, 2H), 7.52 (d, 1H), 7.21 (s, 1H), 6.32 (t, 1H), 4.75 (d, 1H), 4.41 (d, 1H), 3.92 (d, 1H), 3.71 (d, 1H), 3.63 (d, 1H), 3.46 (t, 1H), 3.22 (d, 1H), 3.22-3.08 (m, 2H), 2.63 (s, 6H), 1.27 (d, 3H), 1.07 (t, 3H);

LCMS (method A), (M+H+) 525, Rt=10.36 min.

Example 15

(S)-1-ethyl-3-(4-(2-(3-methylmorpholino)-6-(5-(methylsulfonyl)pyridin-3-yl)pyrimidin-4-yl)phenyl)urea

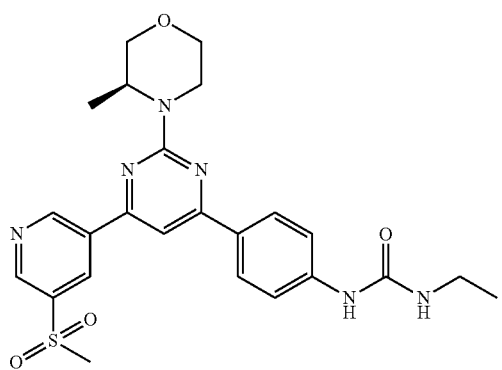 [SMILES: CCNC(=O)Nc1ccc(-c2cc(-c3cncc(S(C)(=O)=O)c3)nc(N3CCOC[C@@H]3C)n2)cc1]

Method as described for Example 8 using 5-(methylsulfonyl)pyridine-3-boronic acid. The reaction mixture was concentrated in vacuo, and the residue dissolved in DMSO, filtered and purified by prep HPLC (low pH) to afford a green solid (20 mg, 19%).

$^1$H NMR (d$_6$-DMSO) 9.74 (s, 1H), 9.20 (s, 1H), 9.04 (s, 1H), 8.81 (s, 1H), 8.23 (d, 2H), 7.98 (s, 1H), 7.58 (s, 2H), 6.24 (t, 1H), 4.89 (d, 1H), 4.51 (d, 1H), 3.99 (d, 1H), 3.79 (d, 1H), 3.68 (d, 1H), 3.52 (t, 1H), 3.29 (t, 1H), 3.22-3.08 (m, 2H), 1.27 (d, 3H), 1.07 (t, 3H);

LCMS (method A), (M+H+) 497, Rt=9.58 min.

Example 16

(S)-1-ethyl-3-(4-(6-(2-(hydroxymethyl)phenyl)-2-(3-methylmorpholino)pyrimidin-4-yl)phenyl)urea

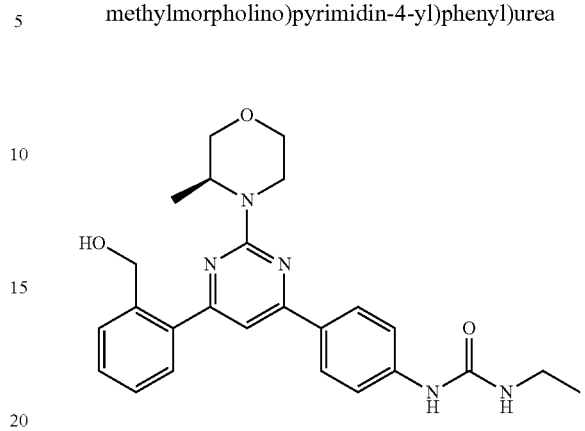

Method as described for Example 8 using 2-(hydroxymethyl)benzeneboronic acid. The reaction mixture concentrated in vacuo, and the residue dissolved in DMSO, filtered and purified by prep HPLC (low pH) to afford an off-white solid (17 mg, 18%).

$^1$H NMR (d$_6$-DMSO) 8.75 (s, 1H), 8.09 (d, 2H), 7.66 (d, 1H), 7.59 (d, 1H), 7.55 (d, 2H), 7.49 (dd, 1H), 7.39 (dd, 1H), 7.37 (s, 1H), 6.21 (t, 1H), 5.17 (t, 1H), 4.76-4.66 (m, 3H), 4.41 (d, 1H), 3.95 (d, 1H), 3.74 (d, 1H), 3.65 (d, 1H), 3.49 (t, 1H), 3.24 (t, 1H), 3.17-3.10 (m, 2H), 1.25 (d, 3H), 1.06 (t, 3H);

LCMS (method A), (M+H+) 448, Rt=9.86 min.

Example 17

(S)-1-ethyl-3-(4-(6-(3-methylmorpholino)-2-phenylpyrimidin-4-yl)phenyl)urea

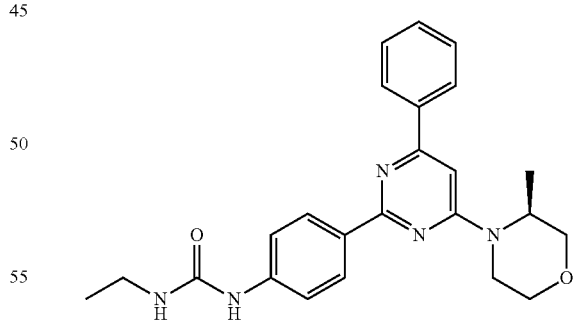

Method as described for Example 3 using benzeneboronic acid and 4-(3-ethylureido)phenyl boronic acid pinacol ester.

$^1$H NMR (d$_6$-DMSO) δ 8.71 (s, 1H), 8.34 (d, 2H), 8.27-8.30 (m, 2H), 7.51-7.54 (m, 5H), 7.17 (s, 1H), 4.7 (br s, 1H), 4.34 (br d, 1H), 4.00 (dd, 1H), 3.79 (d, 1H), 3.67 (dd, 1H), 3.51 (td, 1H), 3.20-3.27 (m, 1H), 3.10-3.16 (m, 2H), 1.25 (d, 3H), 1.07 (t, 3H); LCMS (method A), (M+H+) 418, Rt=7.82 min.

Example 18

(S)-1-ethyl-3-(4-(2-(3-methylmorpholino)-6-(1H-pyrazol-3-yl)pyrimidin-4-yl)phenyl)urea

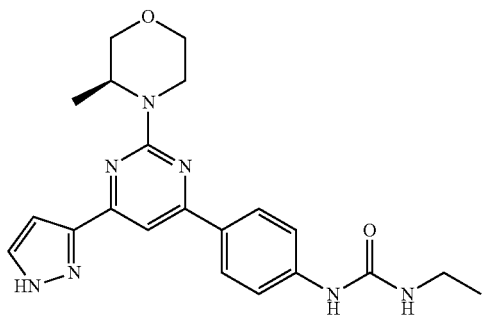 [SMILES: CCNC(=O)Nc1ccc(-c2cc(-c3cc[nH]n3)nc(N3CCOC[C@@H]3C)n2)cc1]

Method as described for Example 8 using 1H-pyrazole-3-boronic acid as starting material. The reaction mixture was concentrated in vacuo, and the residue dissolved in DMSO, filtered and purified by prep HPLC (low pH) to afford brown solid (2 mg, 2%).
$^1$H NMR (d$_6$-DMSO) 13.7-13.3 (m, 1H), 8.75 (s, 1H), 8.08 (d, 1H), 7.79 (br s, 1H), 7.61 (s, 1H), 7.56 (d, 2H), 6.99 (br s, 1H), 6.21 (t, 1H), 4.89 (br s, 1H), 4.60-4.40 (m, 1H), 3.95 (d, 1H), 3.75 (d, 1H), 3.66 (d, 1H), 3.49 (t, 1H), 3.23 (t, 1H), 3.15-3.02 (m, 2H), 1.25 (d, 3H), 1.06 (t, 3H); LCMS (method A), (M+H+) 408, Rt=8.99 min.

Example 19

2-(6-(4-(3-ethylureido)phenyl)-2-morpholinopyrimidin-4-yl)-N-methylbenzenesulfonamide

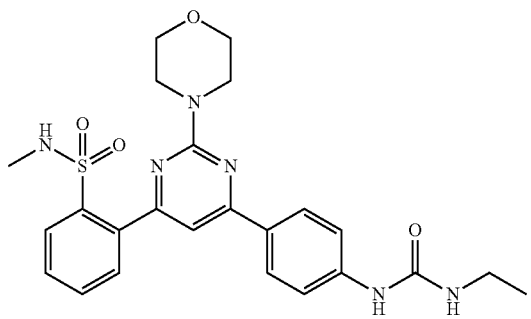 [SMILES: CCNC(=O)Nc1ccc(-c2cc(-c3ccccc3S(=O)(=O)NC)nc(N3CCOCC3)n2)cc1]

Method as described for Example 8 using (4-(N-methylsulfamoyl)phenyl)boronic acid. The reaction mixture was concentrated in vacuo, and the residue dissolved in DMSO, filtered and purified by prep HPLC (low pH) to afford brown solid (2.6 mg, 2%).
$^1$H NMR (d$_6$-DMSO) 8.78 (s, 1H), 8.08 (d, 2H), 7.94 (d, 1H), 7.76 (dd, 1H), 7.70 (dd, 1H), 7.62 (d, 1H), 7.54 (d, 2H), 7.31 (s, 1H), 7.16 (q, 1H), 6.24 (t, 1H), 3.81-3.78 (m, 4H), 3.72-3.66 (m, 4H), 3.17-3.08 (m, 2H), 1.06 (t, 3H);
LCMS (method A), (M+H+) 497, Rt=9.83 min.

Example 20

1-ethyl-3-(4-(6-(2-(methylsulfonyl)phenyl)-2-morpholinopyrimidin-4-yl)phenyl)urea

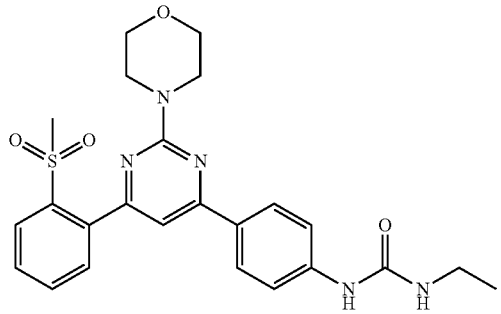 [SMILES: CCNC(=O)Nc1ccc(-c2cc(-c3ccccc3S(C)(=O)=O)nc(N3CCOCC3)n2)cc1]

Step (i)

1-(4-(6-chloro-2-morpholinopyrimidin-4-yl)phenyl)-3-ethylurea

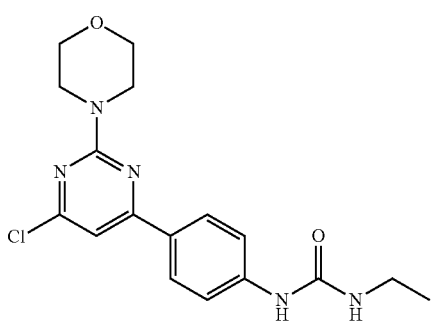 [SMILES: CCNC(=O)Nc1ccc(-c2cc(Cl)nc(N3CCOCC3)n2)cc1]

Method as described for Intermediate 2 using 4-(4,6-dichloropyrimidin-2-yl)morpholine.
LCMS (method B), (M+H+) 362, Rt=2.75 min.
Step (ii)

1-ethyl-3-(4-(6-(2-(methylsulfonyl)phenyl)-2-morpholinopyrimidin-4-yl)phenyl)urea

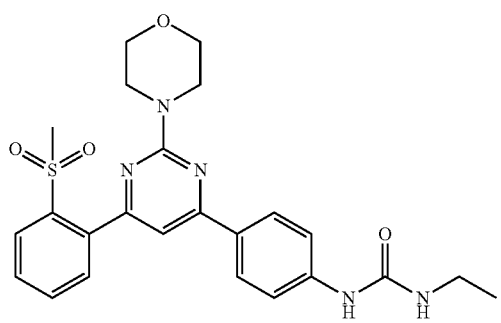 [SMILES: CCNC(=O)Nc1ccc(-c2cc(-c3ccccc3S(C)(=O)=O)nc(N3CCOCC3)n2)cc1]

Method as described for Example 8 using 1-(4-(6-chloro-2-morpholinopyrimidin-4-yl)phenyl)-3-ethylurea and (2-methylsulfonylphenyl)boronic acid. The reaction mixture was concentrated in vacuo, and the residue dissolved in DMSO, filtered and purified by prep HPLC (low pH) to afford a white solid (13.2 mg, 10%).

¹H NMR (d₆-DMSO) 8.81 (s, 1H), 8.11 (d, 2H), 8.08 (d, 1H), 7.84 (dd, 1H), 7.76 (dd, 1H), 7.61 (d, 1H), 7.55 (d, 2H), 7.27 (s, 1H), 6.27 (t, 1H), 3.85-3.75 (m, 4H), 3.70-3.60 (m, 4H), 3.43 (s, 3H), 3.17-3.08 (m, 2H), 1.06 (t, 3H);
LCMS (method A), (M+H+) 482, Rt=9.44 min.

Example 21

(S)-1-cyclopropyl-3-(4-(4-(6-fluoropyridin-3-yl)-6-(3-methylmorpholino)pyrimidin-2-yl)phenyl)urea

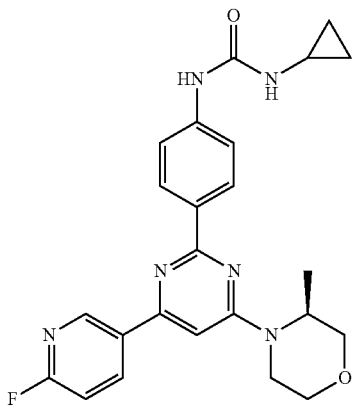 [SMILES: C[C@H]1COCCN1c1cc(-c2ccc(F)nc2)nc(-c2ccc(NC(=O)NC3CC3)cc2)n1]

Method as described for Example 3 using (6-fluoropyridin-3-yl)boronic acid followed by 4-(3-cyclopropylureido)phenyl boronic acid pinacol ester.

¹H NMR (d₆-DMSO) δ 9.13 (d, 1H), 8.84 (dt, 1H), 8.62 (s, 2H), 8.34 (d, 2H), 7.53 (d, 2H), 7.36 (dd, 1H), 6.48 (d, 1H), 4.72 (br s, 1H), 4.35 (d, 1H), 4.00 (dd, 1H), 3.80 (d, 1H), 3.66 (dd, 1H), 3.52 (dt, 1H), 3.25 (dt, 1H), 2.54-2.60 (m, 1H), 1.26 (d, 3H), 0.60-0.68 (m, 2H), 0.34-0.44 (m, 2H);
LCMS (method A), (M+H+) 449, Rt=9.53 min.

Example 22

(S)-1-cyclopropyl-3-(4-(4-(3-methylmorpholino)-6-(5-(methylsulfonyl)pyridin-3-yl)pyrimidin-2-yl)phenyl)urea

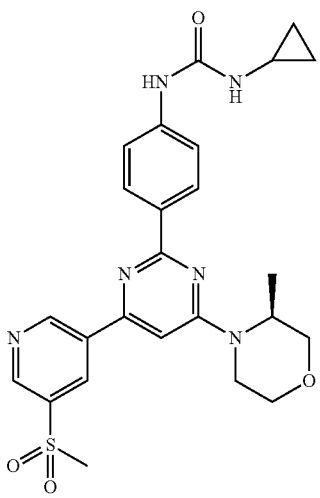 [SMILES: C[C@H]1COCCN1c1cc(-c2cncc(S(C)(=O)=O)c2)nc(-c2ccc(NC(=O)NC3CC3)cc2)n1]

Method as described for Example 3 using (6-(methylsulfonyl)pyridin-3-yl)boronic acid followed by 4-(3-cyclopropylureido)phenyl boronic acid pinacol ester.

¹H NMR (CDCl₃) δ 9.58 (s, 1H), 9.23 (s, 1H), 8.88 (s, 1H), 8.46 (d, 2H), 7.57 (d, 2H), 7.06 (s, 1H), 6.78 (s, 1H), 4.96 (br s, 1H), 4.58 (br s, 1H), 4.28 (d, 1H), 4.10 (d, 1H), 3.88 (d, 1H), 3.80 (d, 1H), 3.65 (t, 1H), 3.40 (dt, 1H), 3.20 (s, 3H), 2.64 (br s, 1H), 1.40 (d, 3H), 0.86-0.91 (m, 2H), 0.70-0.73 (br s, 2H);
LCMS (method A), (M+H+) 509, Rt=8.94 min.

Example 23

(S)-1-cyclopropyl-3-(4-(4-(5-fluoropyridin-3-yl)-6-(3-methylmorpholino)pyrimidin-2-yl)phenyl)urea

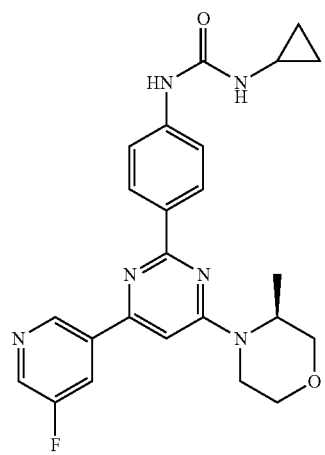 [SMILES: C[C@H]1COCCN1c1cc(-c2cncc(F)c2)nc(-c2ccc(NC(=O)NC3CC3)cc2)n1]

Method as described for Example 3 using (5-fluoropyridin-3-yl)boronic acid followed by 4-(3-cyclopropylureido)phenyl boronic acid pinacol ester.

¹H NMR (d₆-DMSO) δ 9.64 (t, 1H), 8.71 (d, 1H), 8.63 (br s, 1H), 8.53-8.58 (dm, 1H), 8.35 (d, 2H), 7.54 (d, 2H), 7.34 (s, 1H), 6.50 (s, 1H), 4.72 (br s, 1H), 4.38 (br d, 1H), 4.00 (dd, 1H), 3.80 (d, 1H), 3.65 (dd, 1H), 3.52 (d, 1H), 3.22-3.30 (m, 1H), 2.53-2.58 (m, 1H), 1.26 (d, 3H), 0.61-0.68 (m, 2H), 0.38-0.44 (m, 2H);
LCMS (method A), (M+H+) 449, Rt=9.59 min.

Example 24

(S)-1-cyclopropyl-3-(4-(4-(3-fluoropyridin-4-yl)-6-(3-methylmorpholino)pyrimidin-2-yl)phenyl)urea

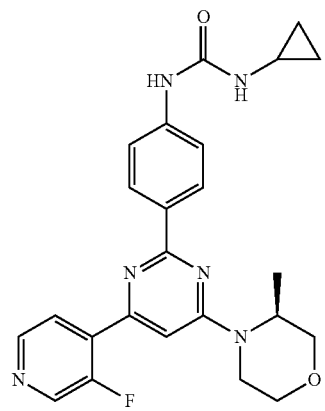 [SMILES: C[C@H]1COCCN1c1cc(-c2ccncc2F)nc(-c2ccc(NC(=O)NC3CC3)cc2)n1]

Method as described for Example 3 using (3-fluoropyridin-4-yl)boronic acid followed by 4-(3-cyclopropylureido)phenyl boronic acid pinacol ester.

¹H NMR (CD₃OD) δ 9.21 (t, 1H), 8.57 (d, 1H), 8.41-8.45 (dm, 1H), 8.39 (d, 2H), 7.51 (d, 2H), 7.13 (s, 1H), 4.73 (br s, 1H), 4.32 (br d, 1H), 4.06 (dd, 1H), 3.86 (d, 1H), 3.78 (dd, 1H), 3.64 (dt, 1H), 3.38 (dt, 1H), 2.58-2.64 (m, 1H), 1.37 (d, 3H), 0.72-0.78 (m, 2H), 0.50-0.56 (m, 2H); LCMS (method A), (M+H+) 449, Rt=9.61 min.

Example 25

(S)-1-cyclopropyl-3-(4-(4-(3-methylmorpholino)-6-(pyridin-4-yl)pyrimidin-2-yl)phenyl)urea

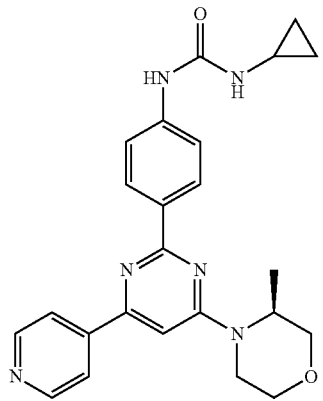 [SMILES: C[C@H]1COCCN1c1cc(-c2ccncc2)nc(-c2ccc(NC(=O)NC3CC3)cc2)n1]

Method as described for Example 3 using (pyridin-4-yl) boronic acid followed by 4-(3-cyclopropylureido)phenyl boronic acid pinacol ester.

¹H NMR (d₆-DMSO) δ 8.76 (dd, 2H), 8.61 (s, 1H), 8.34 (d, 2H), 8.23 (dd, 2H), 7.55 (d, 2H), 7.33 (s, 1H), 6.48 (d, 1H), 4.73 (br s, 1H), 4.37 (d, 1H), 4.01 (dd, 1H), 3.80 (d, 1H), 3.68 (dd, 1H), 3.53 (dt, 1H), 3.23-3.32 (m, 1H), 2.54-2.60 (m, 1H), 1.27 (d, 3H), 0.62-0.68 (m, 2H), 0.40-0.45 (m, 2H); LCMS (method A), (M+H+) 431, Rt=6.93 min.

Example 26

1-cyclopropyl-3-(4-(4-morpholinopyrimidin-2-yl)phenyl)urea

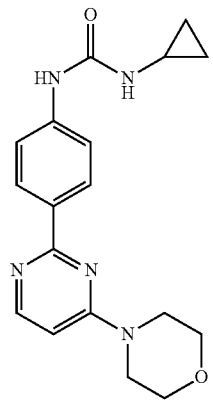 [SMILES: O=C(Nc1ccc(-c2nccc(N3CCOCC3)n2)cc1)NC1CC1]

4-(2-(4-chlorophenyl)pyrimidin-4-yl)morpholine (100 mg 0.5 mmol), (4-(3-cyclopropylureido)phenyl)boronic acid pinacol ester (181 mg, 0.6 mmol), Cs₂CO₃ (326 mg, 1.0 mmol) and Pd(PPh₃)₂Cl₂ (18 mg, 0.025 mmol) were combined in dioxane (3 ml) and water 0.7 ml). The reaction mixture was then heated by microwave at 140° C. for 20 min. The reaction mixture was portioned between EtOAc and water. The organic layer was passed through a PTFE hydrophobic frit and the solvent removed in vacuo. The solid residue was triturated with EtOAc, collected by filtration and dried in vacuo to afford the title compound (78 mg, 46%).

¹H NMR (d₆-DMSO) δ 8.53 (s, 1H), 8.28 (d, 1H), 8.21 (d, 2H), 7.48 (d, 2H), 6.69 (d, 1H), 6.08 (br d, 1H), 3.73-3.63 (m, 8H), 2.58-2.52 (m, 1H), 0.66-0.62 (m, 2H), 0.43-0.39 (m, 2H);

LCMS (method B), (M+H+) 340, Rt=1.58 min.

Example 27

1-methyl-3-(4-(4-morpholinopyrimidin-2-yl)phenyl)urea

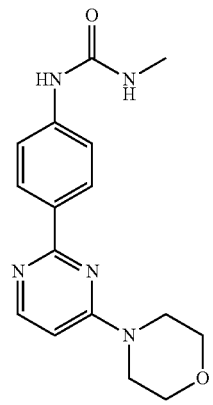

Method as described for Example 26 using 1-methyl-3-(4-(4,4,5,5-tetramethyl-1,3,2-dioxaborolan-2-yl)phenyl)urea to afford the title compound (79 mg, 50%)

¹H NMR (d₆-DMSO) δ 8.74 (s, 1H), 8.37 (d, 1H), 8.20 (d, 2H), 7.48 (d, 2H), 6.67 (d, 1H), 6.08 (q, 1H), 3.73-3.64 (m, 8H), 2.65 (d, 3H);

LCMS (method B), (M+H+) 314, Rt=1.48 min.

Example 28

1-cyclopropyl-3-(4-(2-morpholinopyrimidin-4-yl)phenyl)urea

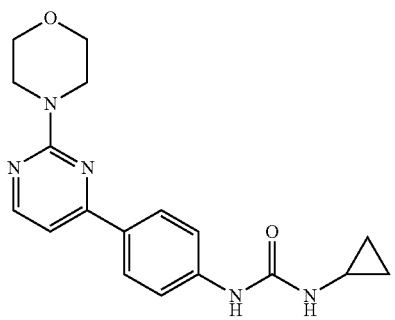 [SMILES: O=C(Nc1ccc(-c2ccnc(N3CCOCC3)n2)cc1)NC1CC1]

To a solution of 4-(4-chloropyrimidin-2-yl)morpholine (80 mg, 0.40 mmol) and (4-(3-cyclopropylureido)phenyl)boronic acid pinacol ester (145 mg, 0.48 mmol) in dioxane (2 mL) was added Pd(PPh$_3$)$_2$Cl$_2$ (14 mg, 0.02 mmol) and Cs$_2$CO$_3$ (2M aq solution, 0.3 mL). The reaction mixture was then heated to reflux for 16 h. The crude reaction mixture was then partitioned between water and EtOAc, the phases separated and the organic layer washed with aqueous NaHCO$_3$ and brine, dried over magnesium sulfate, filtered and the solvent removed in vacuo. The residue was purified by flash chromatography (0-5% EtOAc/MeOH) to yield a white solid (7.8 mg, 6%).

$^1$H NMR (CDCl$_3$) δ 8.35-8.29 (m, 3H), 7.52 (d, 2H), 7.18 (br s, 1H), 6.39 (d, 1H), 5.08 (br s, 1H), 3.84-3.73 (m, 7H), 2.64-2.58 (m, 1H), 1.25 (s, 1H), 0.89-0.83 (m, 2H), 0.79-0.66 (m, 2H); LCMS (method A), (M+H+) 340, Rt=1.59 min.

Example 29

1-ethyl-3-(4-(2-morpholinopyrimidin-4-yl)phenyl) urea

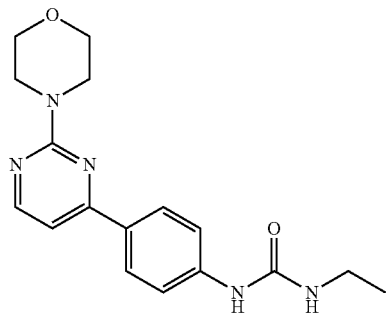 [SMILES: CCNC(=O)Nc1ccc(-c2ccnc(N3CCOCC3)n2)cc1]

Method as described for Example 28 using (4-(3-ethylureido)phenyl)boronic acid pinacol ester.

$^1$H NMR (d$_6$-DMSO) δ 8.25-8.18 (m, 3H), 7.48 (d, 2H), 6.64 (d, 1H), 3.85-3.75 (m, 8H), 3.26 (q, 2H), 1.18 (t, 3H); LCMS (method A), (M+H+) 328, Rt=1.54 min.

Example 30

1-methyl-3-(4-(2-morpholinopyrimidin-4-yl)phenyl) urea

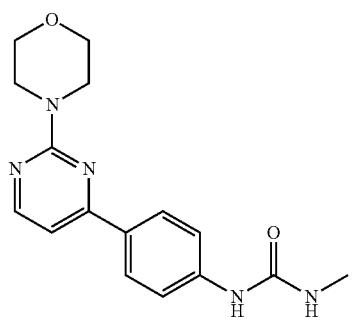 [SMILES: CNC(=O)Nc1ccc(-c2ccnc(N3CCOCC3)n2)cc1]

Method as described for Example 28 using (4-(3-methylureido)phenyl)boronic acid pinacol ester.

$^1$H NMR (d$_6$-DMSO) δ 8.75 (br s, 1H), 8.28 (d, 1H), 8.21 (d, 2H), 7.48 (d, 2H), 6.69 (d, 1H), 6.85 (br q, 1H), 3.75-3.65 (m, 8H), 2.66 (d, 3H);

LCMS (method A), (M+H+) 314, Rt=1.72 min.

Example 31

1-propyl-3-(4-(2-morpholinopyrimidin-4-yl)phenyl) urea

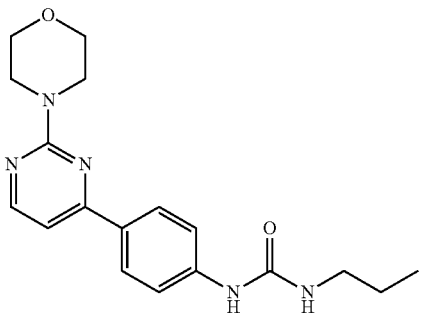 [SMILES: CCCNC(=O)Nc1ccc(-c2ccnc(N3CCOCC3)n2)cc1]

Method as described for Example 28 using (4-(3-propylureido)phenyl)boronic acid pinacol ester.

$^1$H NMR (d$_6$-DMSO) δ 8.65 (s, 1H), 8.28 (d, 1H), 8.21 (d, 2H), 7.47 (d, 2H), 6.69 (d, 1H), 6.22 (t, 1H), 3.75-3.62 (d, 8H), 3.06 (q, 2H), 1.50-1.45 (m, 2H), 0.88 (t, 3H);

LCMS (method A), (M+H+) 342, Rt=1.66 min.

Example 32

1-(4-(4-morpholinopyrimidin-2-yl)phenyl)-3-propylurea

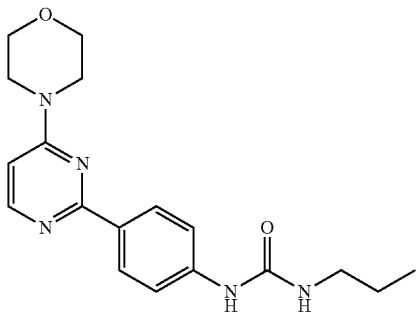 [SMILES: CCCNC(=O)Nc1ccc(-c2nccc(N3CCOCC3)n2)cc1]

Method as described for Example 34 using (4-(3-propylureido)phenyl)boronic acid pinacol ester and 4-(2-chloropyrimidin-4-yl)morpholine which was synthesised according to Intermediate 3, using morpholine as starting material.

$^1$H NMR (d$_6$-DMSO) δ 8.65 (s, 1H), 8.28 (d, 1H), 8.21 (d, 2H), 7.47 (d, 2H), 6.69 (d, 1H), 6.22 (t, 1H), 3.73-3.65 (m, 8H), 3.06 (q, 2H), 1.50-1.45 (m, 2H), 0.88 (t, 3H);

LCMS (method A), (M+H+) 342, Rt=1.67 min.

Example 33

1-(4-(4-morpholinopyrimidin-2-yl)phenyl)urea

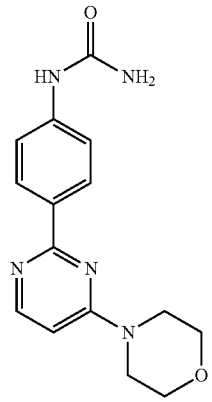 [SMILES: NC(=O)Nc1ccc(-c2nccc(N3CCOCC3)n2)cc1]

Method as described for Example 26 using 1-(4-(4,4,5,5-tetramethyl-1,3,2-dioxaborolan-2-yl)phenyl)urea to afford the title compound (41 mg, 27%).

$^1$H NMR (d$_6$-DMSO) δ 8.75 (s, 1H), 8.28 (d, 1H), 8.20 (d, 2H), 7.48 (d, 2H), 6.69 (d, 1H), 5.93 (s, 2H), 3.73-3.64 (m, 8H);

Example 34

(S)-1-methyl-3-(4-(4-(3-methylmorpholino)pyrimidin-2-yl)phenyl)urea

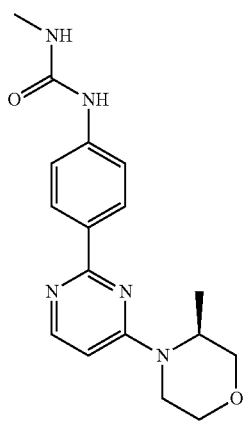 [SMILES: CNC(=O)Nc1ccc(-c2nccc(N3CCOC[C@@H]3C)n2)cc1]

To a solution of (S)-4-(2-chloropyrimidin-4-yl)-3-methylmorpholine (Intermediate 3) (100 mg, 0.47 mmol) and 4-(3-ethylureido)phenylboronic acid pinacol ester (143 mg, 0.52 mmol) in DME:EtOH:H$_2$O (12:5:3, 2 mL) was added Pd(PPh$_3$)$_2$(Cl)$_2$ (17 mg, 0.024 mmol) and Na$_2$CO$_3$ (149 mg, 1.41 mmol). The reaction mixture was then heated by microwave at 120° C. for 1 h. The crude reaction mixture was then partitioned between water and EtOAc, the phases separated and the organic layer washed with aqueous NaHCO$_3$ and brine, dried over magnesium sulfate, filtered and the solvent removed in vacuo. The residue was purified by flash chromatography (2-5% MeOH/DCM) to yield a white solid (12 mg, 8%).

$^1$H NMR (d$_6$-DMSO) δ 8.75 (s, 1H), 8.27 (d, 1H), 8.19 (d, 2H), 7.47 (d, 2H), 6.64 (d, 1H), 6.08 (q, 1H), 4.48 (s, 1H), 4.24-4.10 (m, 1H), 3.96 (dd, 1H), 3.75 (d, 1H), 3.62 (dd, 1H), 3.47 (td, 1H), 3.23-3.08 (m, 1H), 2.65 (d, 3H), 1.20 (d, 3H);
LCMS (method B), (M+H+) 328, Rt=1.53 min.

Example 35

(S)-1-cyclopropyl-3-(4-(4-(3-methylmorpholino)pyrimidin-2-yl)phenyl)urea

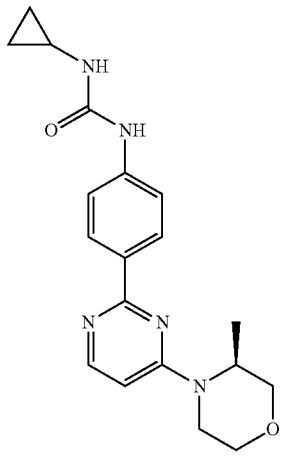 [SMILES: C[C@H]1COCCN1c1ccnc(-c2ccc(NC(=O)NC3CC3)cc2)n1]

Method as described for Example 34 using 4-(3-cyclopropylureido)phenylboronic acid pinacol ester as reagent. Purified by prep LCMS (low pH) to yield a white solid (16 mg, 10%).

$^1$H NMR (d$_6$-DMSO) δ 8.61 (s, 1H), 8.27 (d, 1H), 8.20 (d, 2H), 7.48 (d, 2H), 6.65 (d, 1H), 6.52 (d, 1H), 4.48 (s, 1H), 4.17 (d, 1H), 3.96 (dd, 1H), 3.75 (d, 1H), 3.62 (dd, 1H), 3.47 (td, 2H), 2.55 (q, 1H), 1.20 (d, 3H), 0.68-0.57 (m, 2H), 0.45-0.34 (m, 2H);
LCMS (method B), (M+H+) 354, Rt=1.64 min.

Example 36

1-ethyl-3-(4-(4-morpholinopyrimidin-2-yl)phenyl)urea

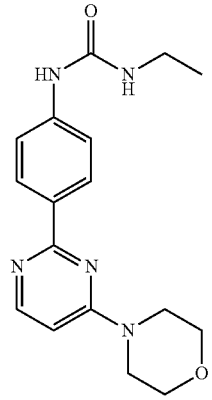 [SMILES: CCNC(=O)Nc1ccc(-c2nccc(N3CCOCC3)n2)cc1]

A suspension of 4-(2-chloropyrimidin-4-yl)-morpholine (100 mg, 0.501 mmol), bis(triphenylphosphine)palladium(II) dichloride (18 mg, 0.025 mmol), sodium carbonate (2M aqueous, 0.376 mL, 0.752 mmol) in DME:H$_2$O:EtOH (7:3:2, 20.1 mL) and DMF (0.4 mL) was heated in the microwave oven at 110° C. for 1 h. The reaction mixture was then diluted with EtOAc, filtered, concentrated in vacuo and the product purified by prep HPLC (low pH) to afford the desired product. (5.1 mg, 3%).

¹H NMR (d₆-DMSO) δ 8.81 (s, 1H), 8.28 (d, J=6.1 Hz, 1H), 8.22 (s, 1H), 8.20 (d, J=8.8 Hz, 1H), 7.48 (d, J=8.8 Hz, 2H), 6.69 (d, J=6.2 Hz, 1H), 6.32 (t, J=5.5 Hz, 1H), 3.75-3.61 (m, 8H), 3.16-3.07 (m, 2H), 1.05 (t, 3H);
LCMS (method A), (M+H+) 328, Rt=4.82 min.

Example 37

(S)-1-ethyl-3-(4-(4-(3-methylmorpholino)pyrimidin-2-yl)phenyl)urea

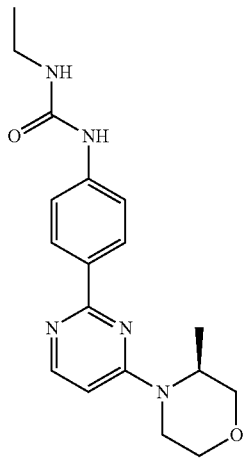 [SMILES: CCNC(=O)Nc1ccc(-c2nccc(N3CCOC[C@@H]3C)n2)cc1]

Method as described for Example 34 using 4-(3-ethylureido)phenylboronic acid pinacol ester as reagent. Purified by flash chromatography (5% MeOH/DCM) to yield an orange solid (11 mg, 7%).
¹H NMR (d₆-DMSO) δ 8.68 (s, 1H), 8.27 (d, 1H), 8.19 (d, 2H), 7.47 (d, 2H), 6.64 (d, 1H), 6.19 (t, 1H), 4.48 (s, 1H), 4.16 (d, 1H), 3.96 (dd, 1H), 3.75 (d, 1H), 3.62 (dd, 1H), 3.53-3.42 (m, 1H), 3.22-3.05 (m, 3H), 1.20 (d, 3H), 1.05 (t, 3H);
LCMS (method B), (M+H+) 342, Rt=1.63 min.

Example 38

(S)-1-ethyl-3-(4-(2-(3-methylmorpholino)pyrimidin-4-yl)phenyl)urea

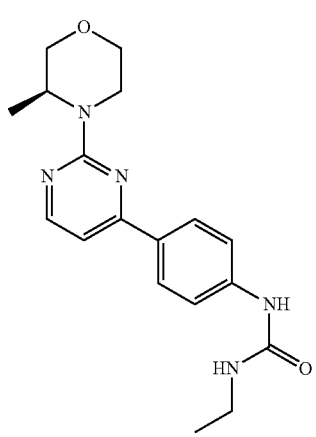 [SMILES: CCNC(=O)Nc1ccc(-c2ccnc(N3CCOC[C@@H]3C)n2)cc1]

Method as described for intermediate 5 using (S)-4-(4-chloropyrimidin-2-yl)-3-methylmorpholine (intermediate 15) and 4-(3-ethylureido)phenyl boronic acid pinacol ester. Material was purified by prep HPLC (low pH) to afford a brown solid, (77 mg, 40%).
¹H NMR (d₆-DMSO) δ 8.78 (s, 1H), 8.36 (d, 1H), 8.02 (d, 2H), 7.53 (d, 2H), 7.12 (d, 1H), 6.24 (t, 1H), 4.71 (s, 1H), 4.38 (d, 1H), 3.94 (d, 1H), 3.71 (d, 1H), 3.62 (d, 1H), 3.49-3.41 (m, 1H), 3.22-3.05 (m, 3H), 1.19 (d, 3H), 1.06 (t, 3H).
LCMS (method A), (M+H+) 342, Rt=7.54 min.

Example 39

(S)-1-cyclopropyl-3-(4-(2-(3-methylmorpholino)pyrimidin-4-yl)phenyl)urea

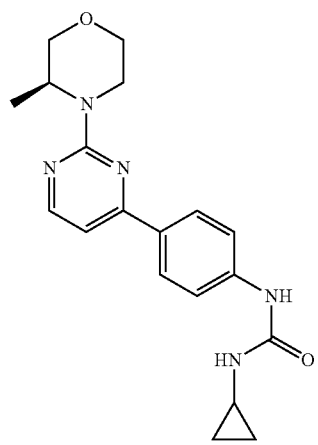 [SMILES: C[C@H]1COCCN1c1nccc(-c2ccc(NC(=O)NC3CC3)cc2)n1]

Method as described for intermediate 5 using (S)-4-(4-chloropyrimidin-2-yl)-3-methylmorpholine (intermediate 15) and 4-(3-cyclopropylureido)phenyl boronic acid pinacol ester. Material was purified using flash chromatography (20-90% EtOAc in petroleum ether 40-60) to afford a light pink solid (130 mg, 66%).
¹H NMR (d₆-DMSO) δ 8.60 (s, 1H), 8.38 (d, 1H), 8.04 (d, 2H), 7.53 (d, 2H), 7.14 (d, 1H), 6.47 (s, 1H), 4.72 (d, 1H), 4.38 (d, 1H), 3.93 (d, 1H), 3.74 (d, 1H), 3.63 (d, 1H), 3.52-3.41 (m, 1H), 3.24-3.13 (m, 1H), 2.61-2.55 (m, 1H), 1.22 (d, 3H), 0.68-0.60 (m, 2H), 0.44-0.38 (m, 2H).
LCMS (method A), (M+H+) 354, Rt=7.67 min.

Example 40

(S)-1-cyclopropyl-3-(4-(6-(5-fluoro-2-(methylsulfonyl)phenyl)-2-(3-methylmorpholino)pyrimidin-4-yl)phenyl)urea

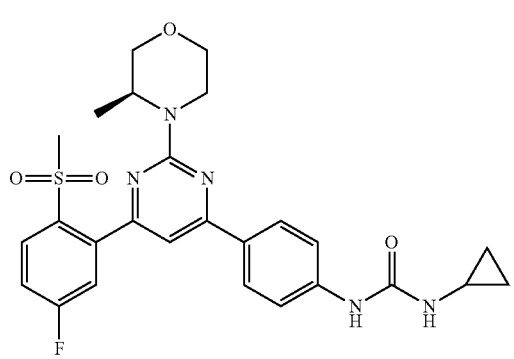 [SMILES: C[C@H]1COCCN1c1nc(-c2ccc(NC(=O)NC3CC3)cc2)cc(-c2cc(F)ccc2S(C)(=O)=O)n1]

Method as described for intermediate 5 using (S)-4-(4-chloro-6-(5-fluoro-2-(methylsulfonyl)phenyl)pyrimidin-2-yl)-3-methylmorpholine (intermediate 16) and 4-(3-cyclopropylureido)phenyl boronic acid pinacol ester. Material was purified by prep HPLC (low pH) to afford a brown solid, (43 mg, 17%).

1H NMR (d<sub>6</sub>-DMSO) δ 8.67 (s, 1H), 8.18-8.14 (m, 1H), 8.11 (d, 2H), 7.66-7.59 (m, 1H), 7.57-7.54 (m, 3H), 7.30 (s, 1H), 6.54 (s, 1H), 4.73 (d, 1H), 4.35 (d, 1H), 3.93 (d, 1H), 3.73 (d, 1H), 3.63 (d, 1H), 3.51-3.43 (m, 1H), 3.43 (s, 3H), 3.30-3.21 (m, 1H), 2.61-2.54 (m, 1H), 1.26 (d, 3H), 0.69-0.62 (m, 2H), 0.45-0.39 (m, 2H).

LCMS (method A), (M+H+) 526, Rt=9.72 min.

Example 41

(S)-1-(4-(6-(5-fluoro-2-(methylsulfonyl)phenyl)-2-(3-methylmorpholino)pyrimidin-4-yl)phenyl)-3-(2-hydroxyethyl)urea

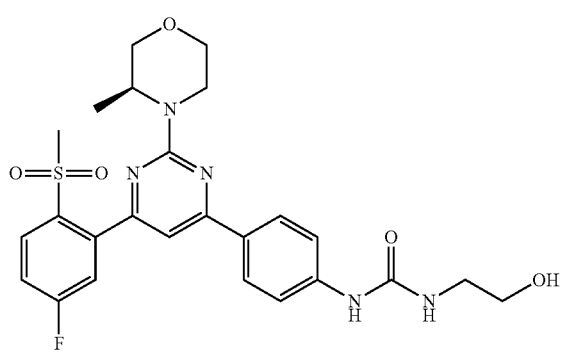 [SMILES: C[C@H]1COCCN1c1nc(-c2ccc(NC(=O)NCCO)cc2)cc(-c2cc(F)ccc2S(C)(=O)=O)n1]

Method as described for intermediate 5 using (S)-4-(4-chloro-6-(5-fluoro-2-(methylsulfonyl)phenyl)pyrimidin-2-yl)-3-methylmorpholine (intermediate 16) and 1-(2-hydroxyethyl)-3-(4-(4,4,5,5-tetramethyl-1,3,2-dioxaborolan-2-yl)phenyl)urea (intermediate 18). Material was purified by prep HPLC (low pH) to afford a brown solid. Further purification was achieved using flash chromatography (20-100% EtOAc in petroleum ether (40:60) to afford a light brown solid (60 mg, 24%).

1H NMR (d<sub>6</sub>-DMSO) δ 8.95 (s, 1H), 8.18-8.14 (m, 1H), 8.11 (d, 2H), 7.65-7.58 (m, 1H), 7.58-7.49 (m, 3H), 7.29 (s, 1H), 6.36 (t, 1H), 4.76 (t, 1H), 4.71 (d, 1H), 4.38 (d, 1H), 3.95 (d, 1H), 3.73 (d, 1H), 3.61 (d, 1H), 3.51-3.43 (m, 3H), 3.42 (s, 3H), 3.29-3.21 (m, 1H), 3.21-3.15 (m, 2H), 1.24 (s, 3H).

LCMS (method A), (M+H+) 530, Rt=8.54 min.

Example 42

(S)-1-cyclopropyl-3-(4-(4-(3-methylmorpholino)-6-(pyridin-2-yl)pyrimidin-2-yl)phenyl)urea

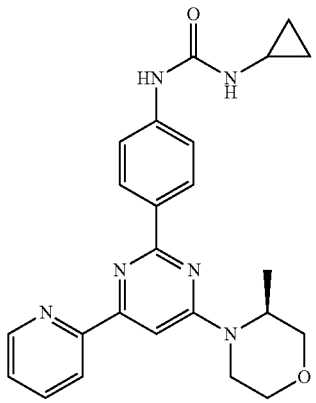 [SMILES: C[C@H]1COCCN1c1cc(-c2ccccn2)nc(-c2ccc(NC(=O)NC3CC3)cc2)n1]

Method as described for intermediate 5 using (S)-4-(2-chloro-6-(pyridin-2-yl)pyrimidin-4-yl)-3-methylmorpholine (intermediate 21) and 4-(3-cyclopropylureido)phenyl boronic acid pinacol ester. Material was purified by prep HPLC (low pH) to afford a light orange solid.

Further purification was achieved using an SCX-2 cartridge to afford an orange solid (113 mg, 60%).

1H NMR (d<sub>6</sub>-DMSO) δ 8.73 (d, 1H), 8.61-8.56 (m, 2H), 8.39 (d, 2H), 8.06-7.99 (m, 1H), 7.57-7.52 (m, 4H), 6.45 (s, 1H), 4.61 (d, 1H), 4.28 (d, 1H), 3.99 (d, 1H), 3.78 (d, 1H), 3.68 (d, 1H), 3.58-3.49 (m, 1H), 3.30-3.22 (m, 1H), 2.60-2.54 (m, 1H), 1.28 (d, 3H), 0.68-0.63 (m, 2H), 0.45-0.39 (m, 2H).

LCMS (method A), (M+H+) 431, Rt=7.14 min.

Example 43

(S)-1-(2-hydroxyethyl)-3-(4-(4-(3-methylmorpholino)-6-(pyridin-2-yl)pyrimidin-2-yl)phenyl)urea

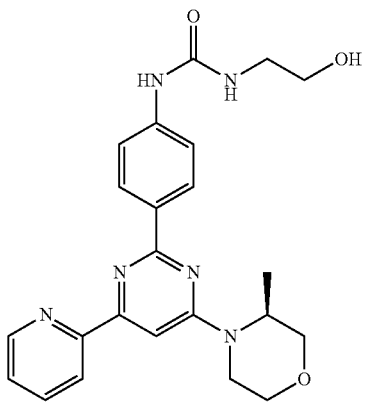 [SMILES: C[C@H]1COCCN1c1cc(-c2ccccn2)nc(-c2ccc(NC(=O)NCCO)cc2)n1]

Method as described for intermediate 5 using (S)-4-(2-chloro-6-(pyridin-2-yl)pyrimidin-4-yl)-3-methylmorpholine (intermediate 21) and 1-(2-hydroxyethyl)-3-(4-(4,4,5,5-tetramethyl-1,3,2-dioxaborolan-2-yl)phenyl)urea (intermediate 18). Material was purified by prep HPLC (low pH) to afford a grey solid. Further purification was achieved using an SCX-2 cartridge to afford a grey solid (122 mg, 64%).

1H NMR (d$_6$-DMSO) δ 8.60 (s, 1H), 8.48 (d, 1H), 8.34 (d, 1H), 8.14 (d, 2H), 7.80-7.75 (m, 1H), 7.33-7.26 (m, 4H), 6.03 (t, 1H), 4.52 (t, 1H), 4.36 (d, 1H), 4.05 (d, 1H), 3.75 (d, 1H), 3.55 (d, 1H), 3.45 (d, 1H), 3.34-3.26 (m, 1H), 3.25-3.20 (m, 2H), 3.06-2.99 (m, 1H), 2.98-2.92 (m, 2H), 1.02 (d, 3H).
LCMS (method A), (M+H+) 435, Rt=5.98 min.

Example 44

(S)-1-(4-(6-(5-fluoro-2-(methylsulfonyl)phenyl)-2-(3-methylmorpholino)pyrimidin-4-yl)phenyl)-3-(2-fluoroethyl)urea

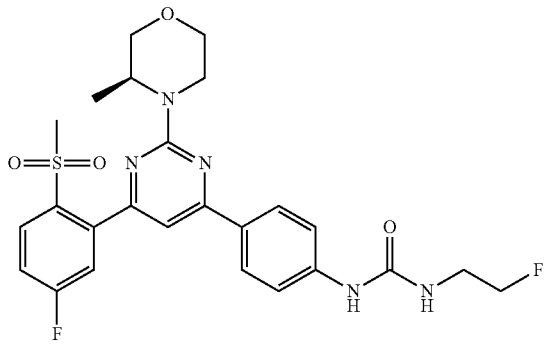 [SMILES: C[C@H]1COCCN1c1nc(-c2ccc(NC(=O)NCCF)cc2)cc(-c2cc(F)ccc2S(C)(=O)=O)n1]

Method as described for intermediate 5 using (S)-4-(4-chloro-6-(5-fluoro-2-(methylsulfonyl)phenyl)pyrimidin-2-yl)-3-methylmorpholine (intermediate 16) and 1-(2-fluoroethyl)-3-(4-(4,4,5,5-tetramethyl-1,3,2-dioxaborolan-2-yl)phenyl)urea (intermediate 19). Material was purified by prep HPLC (low pH) to afford a brown solid. Further purification was achieved using an SCX-2 cartridge to afford a brown solid (50 mg, 22%).

1H NMR (d$_6$-DMSO) δ 8.90 (s, 1H), 8.17-8.09 (m, 3H), 7.65-7.59 (m, 1H), 7.57-7.52 (m, 3H), 7.30 (s, 1H), 6.49 (t, 1H), 4.73 (d, 1H), 4.54 (t, 1H), 4.42 (t, 1H), 4.36 (d, 1H), 3.95 (d, 1H), 3.73 (d, 1H), 3.63 (d, 1H), 3.51-3.44 (m, 2H), 3.42 (s, 3H), 3.39-3.36 (m, 1H), 3.29-3.21 (m, 1H), 1.26 (d, 3H).
LCMS (method A), (M+H+) 532, Rt=9.58 min.

Example 45

1-cyclopropyl-3-(4-(2-((S)-3-methylmorpholino)-6-(2-(methylsulfinyl)pyridin-3-yl)pyrimidin-4-yl)phenyl)urea

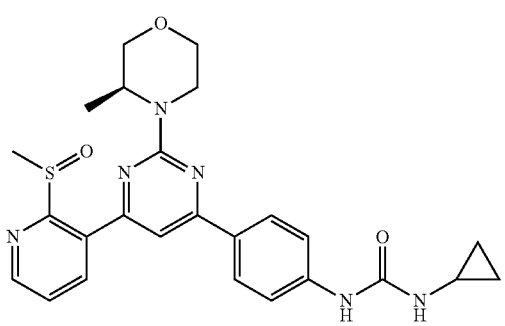 [SMILES: C[C@H]1COCCN1c1nc(-c2ccc(NC(=O)NC3CC3)cc2)cc(-c2cccnc2S(C)=O)n1]

Example 46

(S)-1-cyclopropyl-3-(4-(2-(3-methylmorpholino)-6-(2-(methylsulfonyl)pyridin-3-yl)pyrimidin-4-yl)phenyl)urea

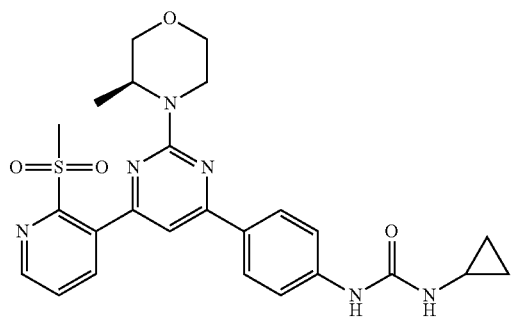 [SMILES: C[C@H]1COCCN1c1nc(-c2ccc(NC(=O)NC3CC3)cc2)cc(-c2cccnc2S(C)(=O)=O)n1]

Method as described for intermediate 6 using (S)-1-cyclopropyl-3-(4-(2-(3-methylmorpholino)-6-(2-(methylthio)pyridin-3-yl)pyrimidin-4-yl)phenyl)urea (intermediate 23) followed by prep HPLC (low pH) to yield two products:

Example 45

1H NMR (d$_6$-DMSO) δ 8.94-8.90 (m, 1H), 8.72 (s, 1H), 8.42-8.36 (m, 1H), 8.16 (d, 2H), 7.78-7.74 (m, 1H), 7.62 (s, 1H), 7.58 (d, 2H), 6.56 (s, 1H), 4.81-4.71 (m, 1H), 4.46 (d, 1H), 4.02-3.95 (m, 1H), 3.81-3.74 (m, 1H), 3.70-3.62 (m, 1H), 3.55-3.46 (m, 2H), 2.90-2.86 (m, 3H), 2.60-2.54 (m, 1H), 1.35-1.25 (m, 3H), 0.69-0.62 (m, 2H), 0.46-0.40 (m, 2H). One proton hidden under the water peak. (15 mg, 17%)
LCMS (method A), (M+H+) 493, Rt=7.70 min.

Example 46

1H NMR (d$_6$-DMSO) δ 8.60 (d, 1H), 8.41 (s, 1H), 8.02 (d, 1H), 7.85 (d, 2H), 7.68-7.64 (m, 1H), 7.33 (d, 2H), 7.20 (s, 1H), 6.28 (s, 1H), 4.58 (d, 1H), 4.24 (d, 1H), 3.74 (d, 1H), 3.52 (d, 1H), 3.41 (d, 1H), 3.29-3.20 (m, 1H), 3.15 (s, 3H), 3.07-2.96 (m, 1H), 2.38-2.32 (m, 1H), 1.02 (d, 3H), 0.47-0.40 (m, 2H), 0.23-0.18 (m, 2H). (54 mg, 38%).
LCMS (method A), (M+H+) 509, Rt=8.76 min.

Example 47

(S)-1-(2,2-difluoroethyl)-3-(4-(6-(5-fluoro-2-(methylsulfonyl)phenyl)-2-(3-methylmorpholino)pyrimidin-4-yl)phenyl)urea

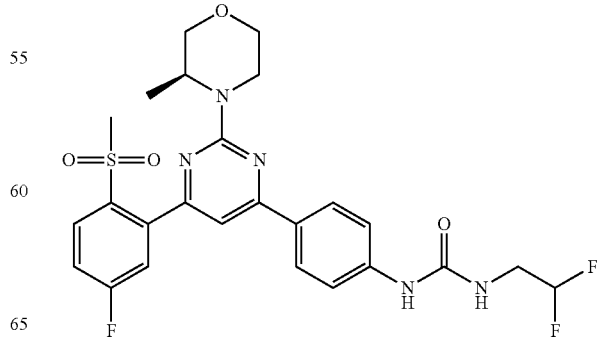

Method as described for intermediate 5 using (S)-4-(4-chloro-6-(5-fluoro-2-(methylsulfonyl)phenyl)pyrimidin-2-yl)-3-methylmorpholine (intermediate 16) and 1-(2,2-difluoroethyl)-3-(4-(4,4,5,5-tetramethyl-1,3,2-dioxaborolan-2-yl)phenyl)urea (intermediate 20). Purification was achieved using flash chromatography (20-90% EtOAc in petroleum ether (40:60). The material was further purified by prep HPLC (low pH) to afford a white solid (20 mg, 23%).

1H NMR (d$_6$-DMSO) δ 9.02 (s, 1H), 8.18-8.11 (m, 3H), 7.65-7.59 (m, 1H), 7.58-7.52 (m, 3H), 7.31 (s, 1H), 6.60 (t, 1H), 6.24-5.92 (m, 1H), 4.76-4.69 (m, 1H), 4.37 (d, 1H), 3.94 (d, 1H), 3.73 (d, 1H), 3.66-3.44 (m, 4H), 3.42 (s, 3H), 3.29-3.20 (m, 1H), 1.24 (d, 3H).

LCMS (method A), (M+H+) 550, Rt=9.91 min.

Example 48

1-(4-(4-(8-oxa-3-azabicyclo[3.2.1]octan-3-yl)pyrimidin-2-yl)phenyl)-3-cyclopropylurea

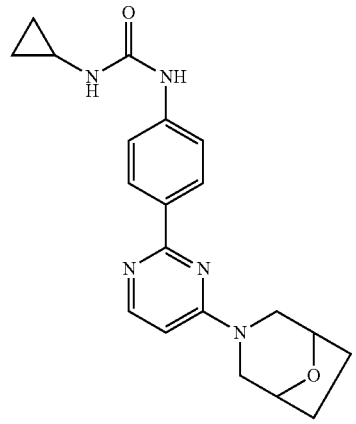 [SMILES: O=C(Nc1ccc(-c2nccc(N3CC4CCC(C3)O4)n2)cc1)NC1CC1]

Method as described for example 49 using 1-cyclopropyl-3-(4-(4,4,5,5-tetramethyl-1,3,2-dioxaborolan-2-yl)phenyl)urea to afford the title compound (70 mg, 43%)

$^1$H NMR (d$_6$-DMSO) 8.57 (s, 1H) 8.26 (d, 1H) 8.19 (d, 2H) 7.50 (d, 2H) 6.64 (d, 1H) 6.47 (d, 1H) 4.47 (s, 2H) 4.25-3.90 (m, 2H) 3.12 (m, 2H) 2.58-2.54 (m, 1H) 1.85 (m, 2H) 1.70 (m, 2H) 0.64 (m, 2H) 0.43 (m, 2H)

LCMS (method A), (M+H+) 366, Rt=5.07 min.

Example 49

1-(4-(4-(8-oxa-3-azabicyclo[3.2.1]octan-3-yl)pyrimidin-2-yl)phenyl)-3-ethylurea

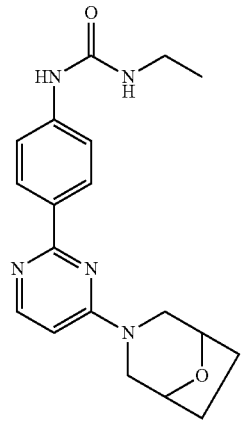 [SMILES: CCNC(=O)Nc1ccc(-c2nccc(N3CC4CCC(C3)O4)n2)cc1]

3-(2-chloropyrimidin-4-yl)-8-oxa-3-azabicyclo[3,2,1]octane (intermediate 24) (100 mg, 0.44 mmol) was stirred with 1-ethyl-3-(4-(4,4,5,5-tetramethyl-1,3,2-dioxaborolan-2-yl)phenyl)urea (141 mg, 0.48 mmol), Pd(dppf)Cl$_2$:DCM (18 mg, 0.002) and Na$_2$CO$_3$(140 mg, 1.3 mmol) in DME:Water (4:1) for 30 minutes at 130° C. in microwave conditions. The reaction mixture was filtered through a celite545 cake and washed with methanol. The reaction mixture was concentrated in vacuo. The resulting oil was purified by prep HPLC at low pH to afford the title compound as a white solid. (20 mg, 13%)

$^1$H NMR (d$_6$-DMSO) 8.65 (s, 1H) 8.26 (d, 1H) 8.20 (d, 2H) 7.47 (d, 2H) 6.61 (d, 1H) 6.16 (t, 1H) 4.46 (s, 2H) 4.15-4.0 (s, 2H) 3.16-3.06 (m, 4H) 1.87-1.82 (m, 2H) 1.73-1.66 (m, 2H) 1.06 (t, 3H)

LCMS (method A), (M+H+) 354, Rt=5.06 min.

Example 50

1-(4-(4-(8-oxa-3-azabicyclo[3.2.1]octan-3-yl)pyrimidin-2-yl)phenyl)-3-(2-hydroxyethyl)urea

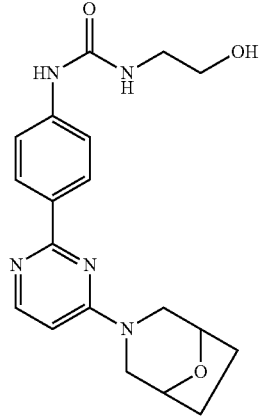 [SMILES: O=C(NCCO)Nc1ccc(-c2nccc(N3CC4CCC(C3)O4)n2)cc1]

Method as described for example 49 using 1-(2-hydroxyethyl)-3-(4-(4,4,5,5-tetramethyl-1,3,2-dioxaborolan-2-yl)phenyl)urea (intermediate 18). Purified by flash chromatography (80-100% EtOAc in Petroleum Ether 40-60 followed by 0-10% MeOH in EtOAc) to yield the title compound (24 mg, 15%)

$^1$H NMR (d$_6$-DMSO) 8.79 (s, 1H) 8.26 (d, 1H) 8.20 (d, 1H) 7.47 (d, 2H) 6.61 (d, 1H) 6.26 (t, 1H) 4.76 (t, 1H) 4.47 (s, 2H) 3.46 (q, 2H) 3.18 (m, 5H) 3.09 (m, 2H) 1.85 (m, 2H) 1.69 (m 2H)

LCMS (method A), (M+H+) 370, Rt=4.54 min.

Example 51

1-(4-(4-(8-oxa-3-azabicyclo[3.2.1]octan-3-yl)pyrimidin-2-yl)phenyl)-3-(2,2-difluoroethyl)urea

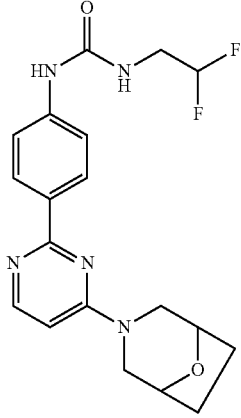 [SMILES: O=C(NCC(F)F)Nc1ccc(-c2nccc(N3CC4CCC(C3)O4)n2)cc1]

Method as described for example 49 using 1-(2,2-difluoroethyl)-3-(4-(4,4,5,5-tetramethyl-1,3,2-dioxaborolan-2-yl)phenyl)urea (intermediate 20). Purified by flash chromatography (80-100% EtOAc in Petroleum Ether 40-60) to yield the title compound. (98 mg, 57%)

$^1$H NMR (d$_6$-DMSO) 8.91 (s, 1H) 8.26 (d, 1H) 8.22 (d, 2H) 7.49 (d, 2H) 6.62 (d, 1H) 6.54 (t, 1H) 6.22-5.92 (m, 1H) 4.48 (s, 2H) 4.08 (s, 2H) 3.54 (m, 2H) 3.09 (d, 2H) 1.85 (m, 2H) 1.70 (m, 2H)

LCMS (method A), (M+H+) 390, Rt=5.20 min

Example 52

1-(4-(4-(8-oxa-3-azabicyclo[3.2.1]octan-3-yl)pyrimidin-2-yl)phenyl)-3-(2-fluoroethyl)urea

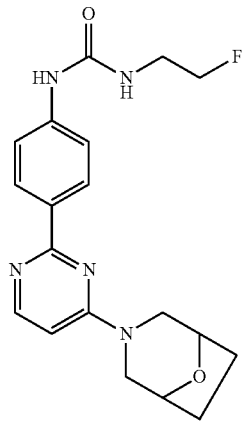 [SMILES: O=C(NCCF)Nc1ccc(-c2nccc(N3CC4CCC(C3)O4)n2)cc1]

Method as described for example 49 using 1-(2-fluoroethyl)-3-(4-(4,4,5,5-tetramethyl-1,3,2-dioxaborolan-2-yl)phenyl)urea (intermediate 19). (9 mg, 6%).

$^1$H NMR (d$_6$-DMSO) 8.80 (s, 1H) 8.26 (d, 1H) 8.22 (d, 2H) 7.48 (d, 2H) 6.62 (d, 1H) 6.45 (t, 1H) 4.55-4.39 (m, 4H) 4.20-3.95 (m, 2H) 3.45-3.35 (m, 2H) 3.09 (m, 2H) 1.85 (m, 2H) 1.70 (m, 2H)

LCMS (method A), (M+H+) 372, Rt=4.84 min.

Example 53

(S)-1-(2-hydroxyethyl)-3-(4-(4-(3-methylmorpholino)pyrimidin-2-yl)phenyl)urea

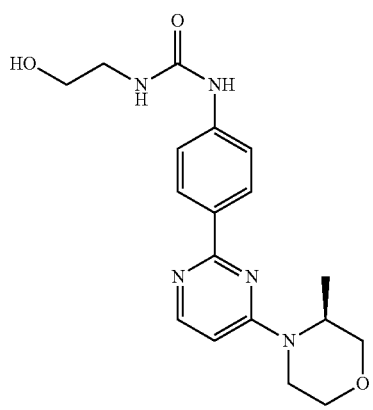 [SMILES: C[C@H]1COCCN1c1ccnc(-c2ccc(NC(=O)NCCO)cc2)n1]

Method as described for example 49 using (S)-4-(2-chloropyrimidin-4-yl)-3-methylmorpholine (intermediate 3) and 1-(2-hydroxyethyl)-3-(4-(4,4,5,5-tetramethyl-1,3,2-dioxaborolan-2-yl)phenyl)urea (intermediate 18). The mixture was purified by prep HPLC at high pH to afford the title compound. (24 mg, 15%).

$^1$H NMR (d$_6$-DMSO) 8.85 (s, 1H) 8.28 (d, 1H) 8.21 (d, 2H) 7.46 (d, 2H) 6.64 (d, 1H) 6.33 (t, 1H) 4.76 (s, 1H) 4.48 (s, 1H) 4.17 (d, 1H) 3.97 (m, 1H) 3.76 (d, 1H) 3.67 (m, 1H) 3.52-3.48 (m, 3H) 3.21-3.13 (m, 3H) 1.22 (d, 3H)

LCMS (method A), (M+H+) 358, Rt=4.49 min.

Example 54

(S)-1-(2,2-difluoroethyl)-3-(4-(4-(3-methylmorpholino)pyrimidin-2-yl)phenyl)urea

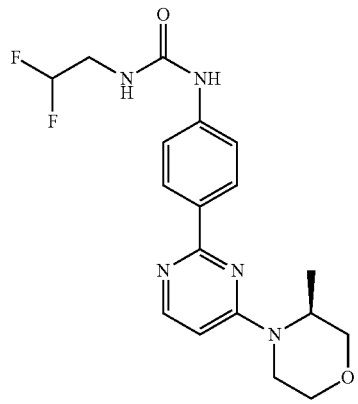 [SMILES: C[C@H]1COCCN1c1ccnc(-c2ccc(NC(=O)NCC(F)F)cc2)n1]

Method as described for example 49 using (S)-4-(2-chloropyrimidin-4-yl)-3-methylmorpholine (intermediate 3) and 1-(2,2-difluoroethyl)-3-(4-(4,4,5,5-tetramethyl-1,3,2-dioxaborolan-2-yl)phenyl)urea (intermediate 20). Purified by prep HPLC at high pH to afford the title compound. (68 mg, 38%).

$^1$H NMR (d$_6$-DMSO) 8.92 (s, 1H) 8.28 (d, 1H) 8.22 (d, 2H) 7.48 (d, 2H) 6.66 (d, 1H) 6.54 (t, 1H) 6.22-5.92 (m, 1H) 4.48 (s, 1H) 4.17 (d, 1H) 3.97 (m, 1H) 3.76 (d, 1H) 3.66-3.44 (m, 4H) 3.21-3.13 (m, 1H) 1.22 (d, 3H)

LCMS (method A), (M+H+) 378, Rt=5.16 min.

Example 55

(S)-1-(2-fluoroethyl)-3-(4-(4-(3-methylmorpholino)pyrimidin-2-yl)phenyl)urea

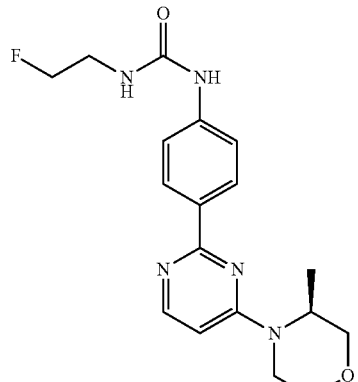

Method as described for example 49 using (S)-4-(2-chloropyrimidin-4-yl)-3-methylmorpholine (intermediate 3) and 1-(2-fluoroethyl)-3-(4-(4,4,5,5-tetramethyl-1,3,2-dioxaborolan-2-yl)phenyl)urea (intermediate 19). The mixture was purified by prep HPLC at high pH to afford the title compound. (15 mg, 9%).

$^1$H NMR (d$_6$-DMSO) 8.97 (s, 1H) 8.37 (d, 1H) 8.29 (d, 2H) 7.57 (d, 2H) 6.73 (d, 1H) 6.66 (t, 1H) 4.64-4.48 (m, 3H) 4.26 (d, 1H) 4.05 (m, 1H) 3.72 (m, 1H) 3.62-3.44 (m, 4H) 3.29-3.22 (m, 1H) 1.30 (d, 3H)

LCMS (method A), (M+H+) 360, Rt=4.90 min.

Example 56

1-(4-(2-(8-oxa-3-azabicyclo[3.2.1]octan-3-yl)pyrimidin-4-yl)phenyl)-3-ethylurea

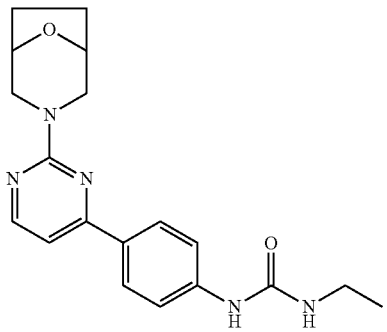 [SMILES: CCNC(=O)Nc1ccc(-c2ccnc(N3CC4CCC(C3)O4)n2)cc1]

4-(2-(8-oxa-3-azabicyclo[3.2.1]octan-3-yl)pyrimidin-4-yl)aniline (intermediate 26) (100 mg, 0.354 mmol) was stirred with triethylamine (74 µl, 0.532 mmol) and ethylisocyanate (42 µl, 0.531 mmol) in DCM (2 ml) overnight. The reaction mixture was concentrated in vacuo and then purified by prep HPLC at low pH. (24 mg, 19%)

$^1$H NMR (d$_6$-DMSO) 8.74 (s, 1H) 8.35 (d, 1H) 8.02 (d, 2H) 7.52 (d, 2H) 7.14 (d, 1H) 6.20 (t, 1H) 4.43 (s, 2H) 4.30 (d, 2H) 3.17-3.06 (m, 4H) 1.83 (m, 2H) 1.69 (m, 2H) 1.06 (t, 3H)

LCMS (method A), (M+H+) 354, Rt=7.16 min.

Example 57

1-(4-(2-(8-oxa-3-azabicyclo[3.2.1]octan-3-yl)pyrimidin-4-yl)phenyl)-3-cyclopropylurea

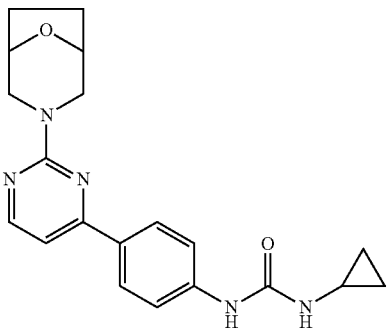 [SMILES: O=C(Nc1ccc(-c2ccnc(N3CC4CCC(C3)O4)n2)cc1)NC1CC1]

Method as described for example 56 using cyclopropaneisocyanate. (32 mg, 25%)

$^1$H NMR (d$_6$-DMSO) 8.64 (s, 1H) 8.35 (d, 1H) 8.02 (d, 2H) 7.52 (d, 2H) 7.14 (d, 1H) 6.50 (d, 1H) 4.43 (s, 2H) 4.30 (d, 2H) 3.12-3.05 (m, 2H) 2.55 (m, 1H) 1.83 (m, 2H) 1.68 (m, 2H) 0.64 (m, 2H) 0.41 (m, 2H)

LCMS (method A), (M+H+) 366, Rt=7.27 min.

Example 58

(S)-1-(2-hydroxyethyl)-3-(4-(2-(3-methylmorpholino)pyrimidin-4-yl)phenyl)urea

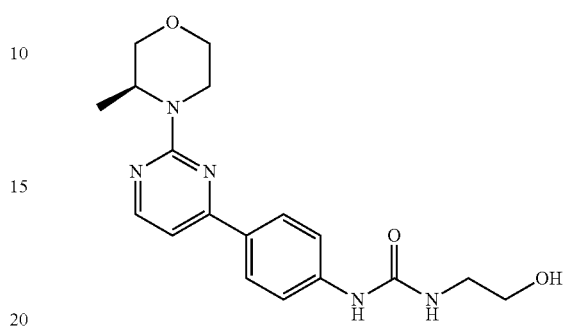

(S)-phenyl(4-(2-(3-methylmorpholino)pyrimidin-4-yl)phenyl)carbamate (intermediate 29) (100 mg, 0.26 mmol) was stirred with triethylamine (85 mg, 0.82 mmol) and ethanolamine (78 mg, 1.28 mmol) in DMF (1 ml) for 2 hours at room temperature. The crude residue was purified by flash chromatography (0-10% EtOH:MeOH) to yield the title compound. (34 mg, 8%)

$^1$H NMR (d$_6$-DMSO) 8.86 (s, 1H) 8.38 (d, 1H) 8.02 (d, 2H) 7.52 (d, 2H) 7.14 (d, 1H) 6.28 (t, 1H) 4.75 (t, 1H) 4.75 (m, 1H) 4.37 (d, 1H) 3.94 (m, 1H) 3.74 (d, 1H) 3.61 (m, 1H) 3.43 (m, 3H) 3.16 (m, 3H) 1.21 (d, 3H)

LCMS (method A), (M+H+) 358, Rt=6.12 min.

Example 59

1-(4-(2-(8-oxa-3-azabicyclo[3.2.1]octan-3-yl)pyrimidin-4-yl)phenyl)-3-(2-hydroxyethyl)urea

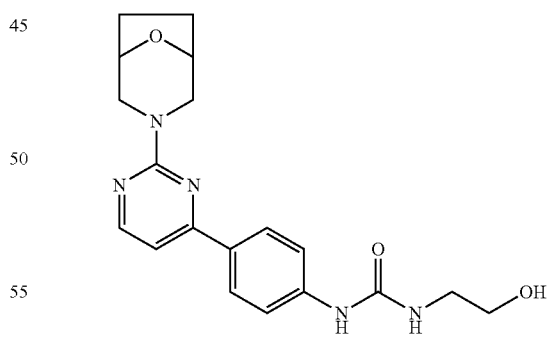

Method as described for example 58 using phenyl(4-(2-(8-oxa-3-azabicyclo[3.2.1]octan-3-yl)pyrimidin-4-yl)phenyl) carbamate intermediate 27. (22 mg, 39%)

$^1$H NMR (d$_6$-DMSO) 8.87 (s, 1H) 8.35 (d, 1H) 8.03 (d, 2H) 7.51 (d, 2H) 7.14 (d, 1H) 6.27 (t, 1H) 4.76 (t, 1H) 4.43 (s, 2H) 4.31 (d, 2H) 3.46 (q, 2H) 3.17 (q, 2H) 3.09 (m, 2H) 1.83 (m, 2H) 1.68 (m, 2H)

LCMS (method A), (M+H+) 370, Rt=6.03 min.

Example 60

(S)-1-(4-(4-(3-methylmorpholino)pyrimidin-2-yl)phenyl)-3-(pyridin-4-yl)urea

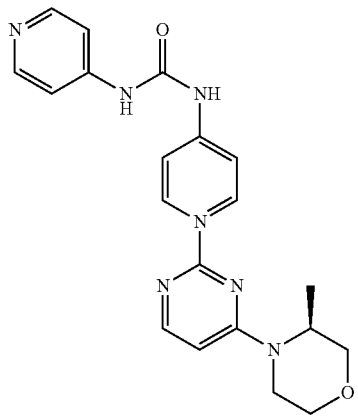

(S)-4-(2-chloropyrimidin-4-yl)-3-methylmorpholine (intermediate 3) (100 mg, 0.47 mmol) was stirred with 1-(pyridin-4-yl)-3-(4-(4,4,5,5-tetramethyl-1,3,2-dioxaborolan-2-yl)phenyl)urea (intermediate 30) (175 mg, 0.52 mmol), Na$_2$CO$_3$ (149 mg, 1.4 mmol) and Pd(dppf)Cl$_2$:DCM (19 mg, 0.02 mmol) in DME:Water (4:1)(5 ml) for 30 mins at 130° C. in a microwave. The reaction mixture was filtered through a celite545 cake and washed with methanol. The solvent was removed in vacuo and the crude residue was purified by prep HPLC at high pH. Further purification was achieved using an SCX-2 cartridge yielding the title compound. (32 mg, 17%)

$^1$H NMR (d$_6$-DMSO) 9.17 (s, 1H) 9.10 (s, 1H) 8.38 (d, 2H) 8.30 (m, 3H) 7.56 (d, 2H) 7.46 (d, 2H) 6.68 (d, 1H) 4.51 (s, 1H) 4.18 (d, 1H) 3.98 (m, 1H) 3.77 (d, 1H) 3.64 (m, 1H) 3.49 (m, 1H) 3.18 (m, 1H) 1.23 (d, 3H)

LCMS (method B), (M+H+) 391, Rt=1.35 min.

Example 61

1-(4-(4-(8-oxa-3-azabicyclo[3.2.1]octan-3-yl)pyrimidin-2-yl)phenyl)-3-(pyridin-4-yl)urea

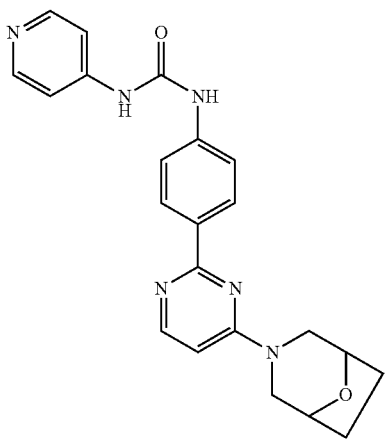 [SMILES: O=C(Nc1ccncc1)Nc1ccc(-c2nccc(N3CC4CCC(C3)O4)n2)cc1]

Method as described for example 60 using 3-(2-chloropyrimidin-4-yl)-8-oxa-3-azabicyclo[3.2.1]octane (intermediate 24). (27 mg, 12%)

$^1$H NMR (d$_6$-DMSO) 9.17 (s, 1H) 9.10 (s, 1H) 8.38 (d, 2H) 8.30 (m, 3H) 7.56 (d, 2H) 7.46 (d, 2H) 6.68 (d, 1H) 4.48 (s, 2H) 4.10 (m, 2H) 3.10 (m, 2H) 1.85 (m, 2H) 1.71 (m, 2H)

LCMS (method B), (M+H+) 403, Rt=1.36 min.

Example 62

1-(4-(6-(5-fluoro-2-(methylsulfonyl)phenyl)-2-morpholinopyrimidin-4-yl)phenyl)-3-(2-hydroxyethyl)urea

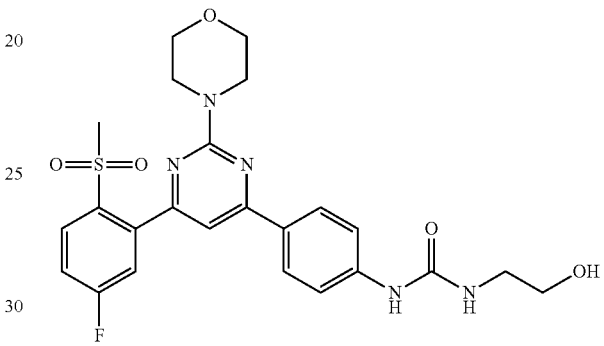

Step (i)

Method as described for intermediate 5 using 4,6-dichloro-2-(methylthio)pyrimidine and 5-fluoro-2-(methylthio)phenylboronic acid. The residue was purified further by flash chromatography (0-10% EtOAc in petroleum ether (40:60) to afford 4-chloro-6-(5-fluoro-2-(methylthio)phenyl)-2-(methylthio)pyrimidine as a white solid, (500 mg, 42%)

LCMS (method B), (M+H+) 301, Rt=3.19 min.

Step (ii)

Method as described for intermediate 5 using 4-chloro-6-(5-fluoro-2-(methylthio)phenyl)-2-(methylthio)pyrimidine and 1-(2-hydroxyethyl)-3-(4-(4,4,5,5-tetramethyl-1,3,2-dioxaborolan-2-yl)phenyl)urea (intermediate 18). Reaction mixture was partitioned between DCM and water, the organic phase passed through a PTFE hydrophobic frit and the solvent removed in vacuo. The residue was purified further by flash chromatography (40-100% EtOAc in petroleum ether (40:60) followed by 0-15% MeOH in petroleum ether (40:60) to afford 1-(4-(6-(5-fluoro-2-(methylthio)phenyl)-2-(methylthio)pyrimidin-4-yl)phenyl)-3-(2-hydroxyethyl)urea as a brown solid, (200 mg, 54%).

LCMS (method B), (M+H+) 445, Rt=2.70 min.

Step (iii)

Method as described for intermediate 6 using 1-(4-(6-(5-fluoro-2-(methylthio)phenyl)-2-(methylthio)pyrimidin-4-yl)phenyl)-3-(2-hydroxyethyl)urea. Reaction mixture was concentrated in-vacuo to afford 1-(4-(6-(5-fluoro-2-(methylsulfonyl)phenyl)-2-(methylsulfonyl)pyrimidin-4-yl)phenyl)-3-(2-hydroxyethyl)urea as a yellow solid, (550 mg, quantitative).

LCMS (method B), (M+H+) 509, Rt=2.08 min.

Step (iv)

1-(4-(6-(5-fluoro-2-(methylsulfonyl)phenyl)-2-(methylsulfonyl)pyrimidin-4-yl)phenyl)-3-(2-hydroxyethyl)urea (275 mg, 0.23 mmol), DIPEA (804, 0.46 mmol) and morpholine (1.0 mL) were heated in a Biotage microwave at 100° C. for 30 minutes. Reaction mixture was partitioned between DCM and water, the organic phase passed through a PTFE hydrophobic frit and the solvent removed in vacuo. The residue was purified further by prep HPLC (low pH) to afford 1-(4-(6-(5-fluoro-2-(methylsulfonyl)phenyl)-2-morpholinopyrimidin-4-yl)phenyl)-3-(2-hydroxyethyl)urea (5.6 mg, 5%).

1H NMR (d$_6$-DMSO) δ 8.91 (s, 1H), 8.17-8.10 (m, 3H), 7.66-7.59 (m, 1H), 7.57-7.50 (m, 3H), 7.32 (s, 1H), 6.31 (t, 1H), 4.75 (t, 1H), 3.85-3.77 (m, 4H), 3.75-3.67 (m, 4H), 3.50-3.40 (m, 5H), 3.22-3.14 (m, 2H).

LCMS (method A), (M+H+) 516, Rt=8.14 min.

Example 63

(S)-1-cyclopropyl-3-(3-fluoro-4-(4-(5-fluoropyridin-3-yl)-6-(3-methylmorpholino)pyrimidin-2-yl)phenyl)urea

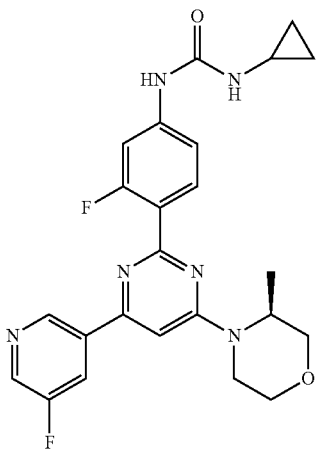 [SMILES: C[C@H]1COCCN1c1cc(-c2cncc(F)c2)nc(-c2ccc(NC(=O)NC3CC3)cc2F)n1]

Method as described for intermediate 5 using (S)-4-(2-chloro-6-(5-fluoropyridin-3-yl)pyrimidin-4-yl)-3-methylmorpholine (intermediate 7) and 1-cyclopropyl-3-(3-fluoro-4-(4,4,5,5-tetramethyl-1,3,2-dioxaborolan-2-yl)phenyl)urea (intermediate 11). Material was purified by prep HPLC twice (low pH) followed by purification using a TsOH cartridge (100 mg) to afford a yellow solid, (4.5 mg, 15%)

1H NMR (d$_6$-DMSO) δ 9.34 (s, 1H), 8.79 (s, 1H), 8.71 (d, 1H), 8.49 (d, 1H), 8.17-8.11 (m, 1H), 7.59 (d, 1H), 7.38 (s, 1H), 7.16 (d, 1H), 6.55 (s, 1H), 4.66 (d, 1H), 4.31 (d, 1H), 3.99 (d, 1H), 3.78 (d, 1H), 3.66 (d, 1H), 3.55-3.47 (m, 1H), 3.29-3.20 (m, 1H), 2.60-2.54 (m, 1H), 1.27 (d, 3H), 0.69-0.63 (m, 2H), 0.47-0.41 (m, 2H).

LCMS (method A), (M+H+) 467, Rt=9.01 min.

Example 64

(S)-1-(4-(6-(5-fluoro-2-(methylsulfonyl)phenyl)-2-(3-methylmorpholino)pyrimidin-4-yl)phenyl)-3-(3-hydroxypropyl)urea

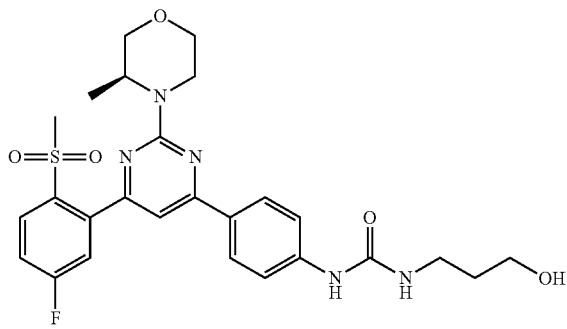 [SMILES: C[C@H]1COCCN1c1nc(-c2ccc(NC(=O)NCCCO)cc2)cc(-c2cc(F)ccc2S(C)(=O)=O)n1]

Method as described for example 58 using (S)-phenyl(4-(6-(5-fluoro-2-(methylsulfonyl)phenyl)-2-(3-methylmorpholino)pyrimidin-4-yl)phenyl)carbamate (intermediate 32) (140 mg, 0.25 mmol) and 3-aminopropan-1-ol (28 mg, 0.375 mmol). The reaction mixture was purified by prep HPLC at low pH to afford the title compound as a yellow solid. (29 mg, 21%)

$^1$H NMR (d$_6$-DMSO) 8.82 (s, 1H) 8.16-8.06 (m, 3H) 7.61 (m, 1H) 7.53 (m, 3H) 7.28 (s, 1H) 6.27 (t, 1H) 4.72 (m, 1H) 4.52 (s, 1H) 4.36 (d, 1H) 3.94 (m, 1H) 3.74 (d, 1H) 3.62 (m, 1H) 3.47 (m, 3H) 3.43 (s, 3H) 3.29-3.12 (m, 3H) 1.60 (m, 2H) 1.23 (d, 3H)

LCMS (method A), (M+H+) 544.20, Rt=544 min.

Examples 65

(S)-1-(3-fluoro-4-(4-(5-fluoropyridin-3-yl)-6-(3-methylmorpholino)pyrimidin-2-yl)phenyl)-3-(2-hydroxyethyl)urea

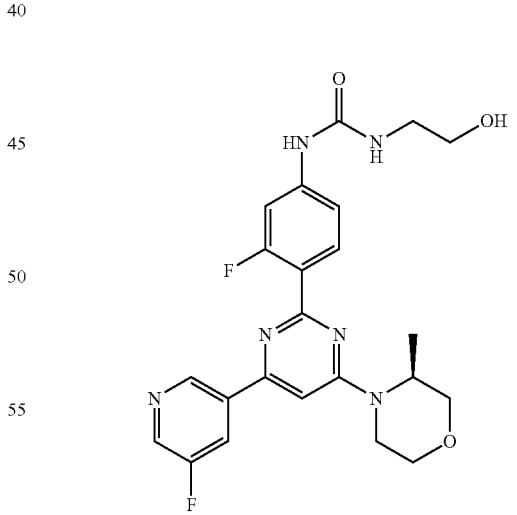

Method as described for intermediate 5 using (S)-4-(2-chloro-6-(5-fluoropyridin-3-yl)pyrimidin-4-yl)-3-methylmorpholine (intermediate 7) and 1-(3-fluoro-4-(4,4,5,5-tetramethyl-1,3,2-dioxaborolan-2-yl)phenyl)-3-(2-hydroxyethyl)urea (intermediate 13). Material was purified by prep HPLC (high pH) to afford a brown solid, (4 1 mg, 25%).

1H NMR (d$_6$-DMSO) δ 9.41 (s, 1H), 9.13 (s, 1H), 8.80 (d, 1H), 8.58 (d, 1H), 8.25-8.18 (m, 1H), 7.66 (d, 1H), 7.45 (s, 1H), 7.21 (d, 1H), 6.43 (t, 1H), 4.86 (t, 1H), 4.76 (s, 1H), 4.42 (d, 1H), 4.10 (d, 1H), 3.86 (d, 1H), 3.76 (d, 1H), 3.64-3.52 (m, 3H), 3.37-3.23 (m, 3H), 1.34 (d, 3H).

LCMS (method A), (M+H+) 471, Rt=7.46 min.

Example 66

(S)-1-cyclopropyl-3-(3-fluoro-4-(4-(5-fluoro-2-(methylsulfonyl)phenyl)-6-(3-methylmorpholino)pyrimidin-2-yl)phenyl)urea

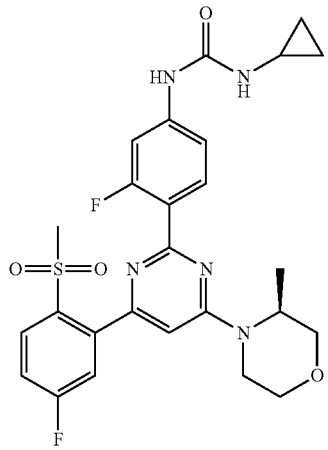 [SMILES: C[C@H]1COCCN1c1cc(-c2cc(F)ccc2S(C)(=O)=O)nc(-c2ccc(NC(=O)NC3CC3)cc2F)n1]

Method as described for intermediate 5 using (S)-4-(2-chloro-6-(5-fluoro-2-(methylsulfonyl)phenyl)pyrimidin-4-yl)-3-methylmorpholine (intermediate 10) and 1-cyclopropyl-3-(3-fluoro-4-(4,4,5,5-tetramethyl-1,3,2-dioxaborolan-2-yl)phenyl)urea (intermediate 11). Material was purified by prep HPLC (low pH) to afford a brown gum, (70 mg, 47%).

1H NMR (d$_6$-DMSO) δ 8.80 (s, 1H), 8.18-8.11 (m, 1H), 7.98-7.91 (m, 1H), 7.63-7.50 (m, 3H), 7.15 (d, 1H), 6.87 (s, 1H), 6.61 (s, 1H), 4.54 (s, 1H), 4.23 (d, 1H), 3.98 (d, 1H), 3.74 (d, 1H), 3.65 (d, 1H), 3.54-3.45 (m, 4H), 3.26-3.16 (m, 1H), 2.59-2.52 (m, 1H), 1.24 (d, 3H), 0.68-0.61 (m, 2H), 0.45-0.39 (m, 2H).

LCMS (method A), (M+H$^+$) 544, Rt=8.75 min.

Example 67

(S)-1-(3-fluoro-4-(4-(5-fluoropyridin-3-yl)-6-(3-methylmorpholino)pyrimidin-2-yl)phenyl)-3-(2-fluoroethyl)urea

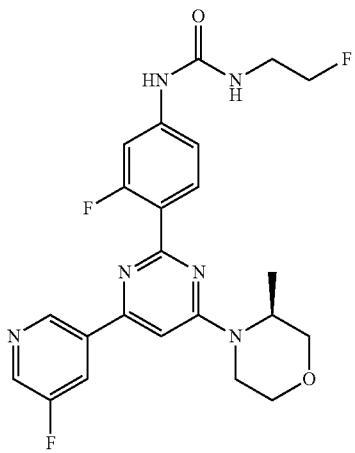 [SMILES: C[C@H]1COCCN1c1cc(-c2cncc(F)c2)nc(-c2ccc(NC(=O)NCCF)cc2F)n1]

Method as described for intermediate 5 using(S)-4-(2-chloro-6-(5-fluoropyridin-3-yl)pyrimidin-4-yl)-3-methylmorpholine (intermediate 7) and 1-(3-fluoro-4-(4,4,5,5-tetramethyl-1,3,2-dioxaborolan-2-yl)phenyl)-3-(2-fluoroethyl)urea (intermediate 14). Material was purified by prep HPLC (high pH) followed by purification using a TsOH cartridge (500 mg) to afford a brown solid, (10 mg, 6%).

1H NMR (d$_6$-DMSO) δ 9.33 (s, 1H), 9.05 (s, 1H), 8.70 (s, 1H), 8.48 (d, 1H), 8.19-8.11 (m, 1H), 7.60 (d, 1H), 7.37 (s, 1H), 7.16 (d, 1H), 6.54 (t, 1H), 4.67 (s, 1H), 4.58-4.53 (m, 1H), 4.46-4.41 (m, 1H), 4.34 (d, 1H), 4.01 (d, 1H), 3.77 (d, 1H), 3.67 (d, 1H), 3.55-3.37 (m, 3H), 3.30-3.19 (m, 1H), 1.27 (d, 3H).

LCMS (method A), (M+H$^+$) 473, Rt=8.79 min.

Example 68

(S)-1-(3-fluoro-4-(4-(5-fluoro-2-(methylsulfonyl)phenyl)-6-(3-methylmorpholino)pyrimidin-2-yl)phenyl)-3-(2-fluoroethyl)urea

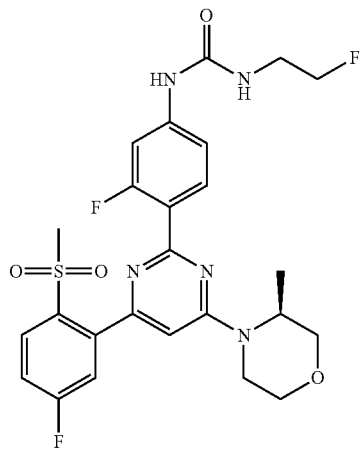 [SMILES: C[C@H]1COCCN1c1cc(-c2cc(F)ccc2S(C)(=O)=O)nc(-c2ccc(NC(=O)NCCF)cc2F)n1]

Method as described for intermediate 5 using (S)-4-(2-chloro-6-(5-fluoro-2-(methylsulfonyl)phenyl)pyrimidin-4-yl)-3-methylmorpholine (intermediate 10) and 1-(3-fluoro-4-(4,4,5,5-tetramethyl-1,3,2-dioxaborolan-2-yl)phenyl)-3-(2-fluoroethyl)urea (intermediate 14). Material was purified by using a TsOH cartridge (500 mg) followed by prep HPLC (low pH) to afford a white solid, (26 mg, 14%).

1H NMR (d$_6$-DMSO) δ 9.06 (s, 1H), 8.18-8.10 (m, 1H), 8.00-7.92 (m, 1H), 7.65-7.49 (m, 3H), 7.12 (d, 1H), 6.87 (s, 1H), 6.57 (t, 1H), 4.59-4.50 (m, 2H), 4.44-4.39 (m, 1H), 4.23 (d, 1H), 3.96 (d, 1H), 3.75 (d, 1H), 3.66 (d, 1H), 3.55-3.44 (m, 5H), 3.41-3.36 (m, 1H), 3.27-3.17 (m, 2H), 1.25 (d, 3H).

LCMS (method A), (M+H$^+$) 550, Rt=8.61 min.

Example 69

(S)-1-(4-(6-(5-fluoro-2-(methylsulfonyl)phenyl)-2-(3-methylmorpholino)pyrimidin-4-yl)phenyl)-3-(1-hydroxy-2-methylpropan-2-yl)urea

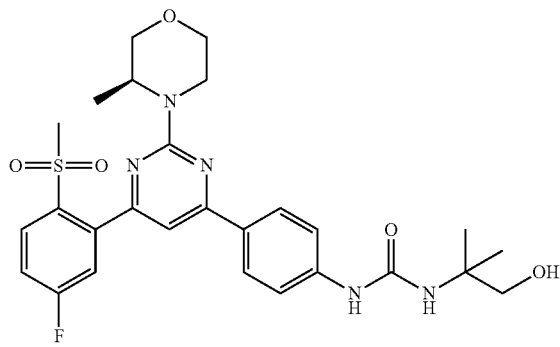 [SMILES: C[C@H]1COCCN1c1nc(-c2ccc(NC(=O)NC(C)(C)CO)cc2)cc(-c2cc(F)ccc2S(C)(=O)=O)n1]

Method as described for example 58 using (S)-phenyl(4-(6-(5-fluoro-2-(methylsulfonyl)phenyl)-2-(3-methylmorpholino)pyrimidin-4-yl)phenyl)carbamate)(intermediate 32) (100 mg, 0.18 mmol) and 2-amino-2-methylpropan-1-ol (24 mg, 0.27 mmol). The reaction mixture was purified by prep HPLC at low pH to afford the title compound as a yellow solid. (45 mg, 45%)

$^1$H NMR (d$_6$-DMSO) 8.83 (s, 1H) 8.17-8.08 (m, 3H) 7.62 (m, 1H) 7.55 (m, 1H) 7.48 (d, 2H) 7.29 (s, 1H) 6.04 (s, 1H) 4.98 (m, 1H) 4.72 (m, 1H) 4.36 (d, 1H) 3.94 (m, 1H) 3.73 (d, 1H) 3.62 (m, 1H) 3.47 (m, 1H) 3.41 (s, 3H) 3.38 (d, 2H) 3.24 (m, 1H) 1.24 (m, 9H)

LCMS (method A), (M+H$^+$) 558, Rt=9.50 min.

Example 70

(S)-2-(3-(4-(6-(5-fluoro-2-(methylsulfonyl)phenyl)-2-(3-methylmorpholino)pyrimidin-4-yl)phenyl)ureido)acetamide

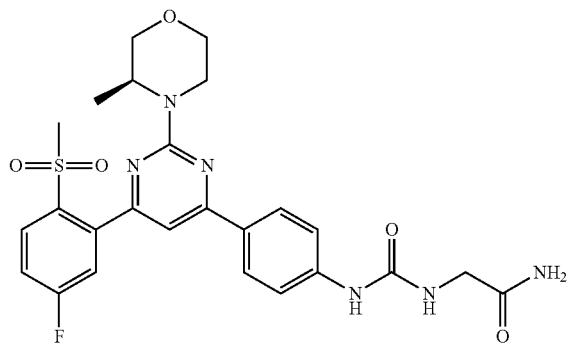 [SMILES: C[C@H]1COCCN1c1nc(-c2ccc(NC(=O)NCC(N)=O)cc2)cc(-c2cc(F)ccc2S(C)(=O)=O)n1]

Method as described for example 58 using (S)-phenyl(4-(6-(5-fluoro-2-(methylsulfonyl)phenyl)-2-(3-methylmorpholino)pyrimidin-4-yl)phenyl)carbamate (intermediate 32) (100 mg, 0.18 mmol) and 2-aminoacetamide (20 mg, 0.27 mmol). The reaction mixture was purified by prep HPLC at low pH to afford the title compound as a yellow solid. (4 1 mg, 43%)

$^1$H NMR (d$_6$-DMSO) 9.14 (s, 1H) 8.17-8.09 (m, 3H) 7.62 (m, 1H) 7.55 (m, 3H) 7.44 (s, 1H) 7.30 (s, 1H) 7.07 (s, 1H) 6.45 (t, 1H) 4.72 (m, 1H) 4.37 (d, 1H) 3.94 (m, 1H) 3.75-3.69 (m, 3H) 3.62 (m, 1H) 3.47 (m, 1H) 3.41 (s, 3H) 3.24 (m, 1H) 1.25 (m, 3H)

LCMS (method A), (M+H$^+$) 543, Rt=7.98 min

Example 71

1-(4-(6-(5-fluoro-2-(methylsulfonyl)phenyl)-2-((S)-3-methylmorpholino)pyrimidin-4-yl)phenyl)-3-(2-hydroxypropyl)urea

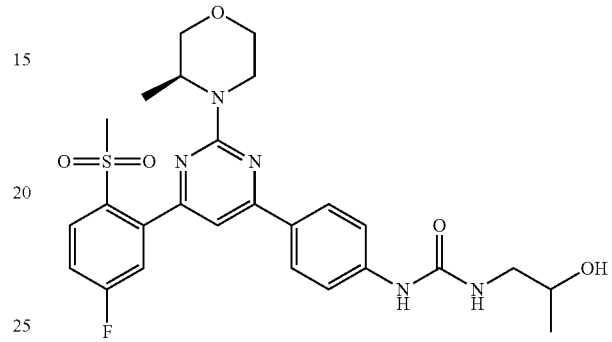

Method as described for example 58 using (S)-phenyl(4-(6-(5-fluoro-2-(methylsulfonyl)phenyl)-2-(3-methylmorpholino)pyrimidin-4-yl)phenyl)carbamate (intermediate 32) (100 mg, 0.18 mmol) and 1-aminopropan-2-ol (20 mg, 0.27 mmol). The reaction mixture was purified by prep HPLC at low pH to afford the title compound as a yellow solid. (46 mg, 48%)

$^1$H NMR (d$_6$-DMSO) 8.91 (s, 1H) 8.17-8.08 (m, 3H) 7.62 (m, 1H) 7.58-7.48 (m, 3H) 7.29 (s, 1H) 6.29 (t, 1H) 4.98 (m, 1H) 4.72 (m, 1H) 4.36 (d, 1H) 3.94 (m, 1H) 3.73 (d, 1H) 3.62 (m, 1H) 3.47 (m, 1H) 3.41 (s, 3H) 3.25 (m, 1H) 3.19-3.11 (m, 2H) 2.96 (m, 1H) 1.25 (d, 3H) 1.06 (d, 3H)

LCMS (method A), (M+H$^+$) 544.2, Rt=8.72 min.

Example 72

(S)-1-(3-fluoro-4-(4-(5-fluoro-2-(methylsulfonyl)phenyl)-6-(3-methylmorpholino)pyrimidin-2-yl)phenyl)-3-(2-hydroxyethyl)urea

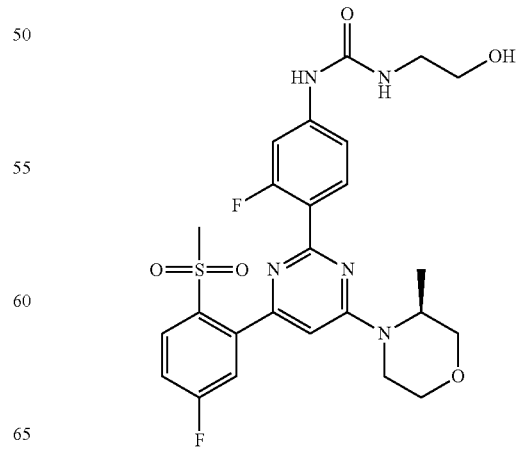

Method as described for intermediate 5 using (S)-4-(2-chloro-6-(5-fluoro-2-(methylsulfonyl)phenyl)pyrimidin-4-yl)-3-methylmorpholine (intermediate 10) and 1-(3-fluoro-4-(4,4,5,5-tetramethyl-1,3,2-dioxaborolan-2-yl)phenyl)-3-(2-hydroxyethyl)urea (intermediate 13). Material was purified by prep HPLC (high pH) followed by purification by prep HPLC (low pH). Due to partial byproduct formation by reaction with formic acid the resulting material was taken up in MeOH (0.5 mL) along with 2 drops of 2M HCl and heated in the microwave for 20 minutes at 90° C. Reaction mixture was purified using a TsOH cartridge (100 mg) to afford a white solid, (12 mg, 8%).

1H NMR (d$_6$-DMSO) δ 9.00 (s, 1H), 8.17-8.11 (m, 1H), 7.98-7.92 (m, 1H), 7.64-7.50 (m, 3H), 7.08 (d, 1H), 6.87 (s, 1H), 6.33 (t, 1H), 4.76 (t, 1H), 4.54 (s, 1H), 4.24 (d, 1H), 3.96 (d, 1H), 3.75 (d, 1H), 3.66 (d, 1H), 3.54-3.43 (m, 6H), 3.26-3.15 (m, 3H), 1.25 (d, 3H).

LCMS (method A), (M+H$^+$) 548, Rt=7.33 min.

Example 73

1-(4-(6-(5-fluoro-2-(methylsulfonyl)phenyl)-2-((S)-3-methylmorpholino)pyrimidin-4-yl)phenyl)-3-((R)-1-hydroxypropan-2-yl)urea

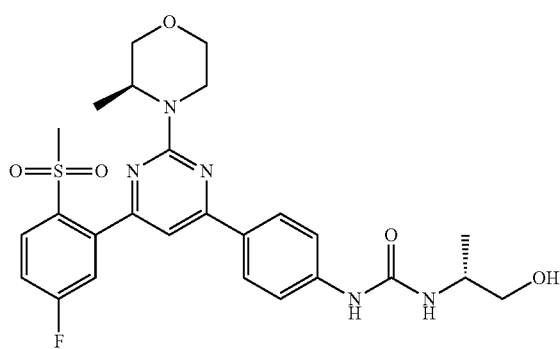 [SMILES: C[C@H](CO)NC(=O)Nc1ccc(-c2cc(-c3cc(F)ccc3S(C)(=O)=O)nc(N3CCOC[C@@H]3C)n2)cc1]

Method as described for example 58 using intermediate 32 (100 mg, 0.18 mmol) and (R)-2-aminopropan-1-ol (20 mg, 0.267 mmol). The reaction mixture was purified by prep HPLC at low pH to afford the title compound. (59 mg, 61%)

$^1$H NMR (d$_6$-DMSO) 8.82 (s, 1H) 8.12 (m, 3H) 7.62 (m, 1H) 7.55 (m, 1H) 7.49 (d, 2H) 7.30 (s, 1H) 6.18 (d, 1H) 4.82 (m, 1H) 4.72 (m, 1H) 4.38 (d, 1H) 3.94 (m, 1H) 3.73 (d, 2H) 3.62 (m, 1H) 3.48 (m, 1H) 3.43 (s, 3H) 3.35 (m, 2H) 3.25 (m, 1H) 1.25 (d, 3H) 1.09 (d, 3H)

LCMS (method A), (M+H$^+$) 544.2, Rt=8.82 min.

Example 74

1-(4-(6-(5-fluoro-2-(methylsulfonyl)phenyl)-2-((S)-3-methylmorpholino)pyrimidin-4-yl)phenyl)-3-((S)-1-hydroxypropan-2-yl)urea

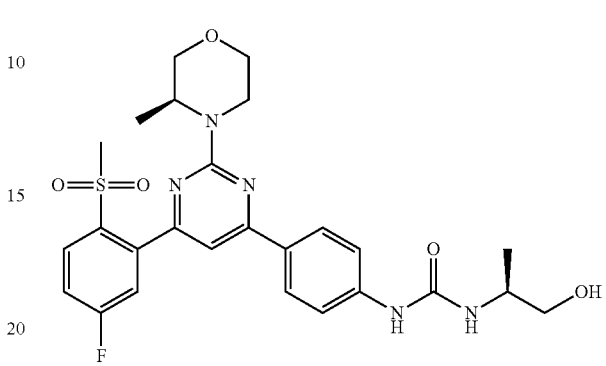

Method as described for example 58 using intermediate 32 (100 mg, 0.18 mmol) and (S)-2-aminopropan-1-ol (20 mg, 0.267 mmol). The reaction mixture was purified by prep HPLC at low pH to afford the title compound. (51 mg, 53%)

$^1$H NMR (d$_6$-DMSO) 8.82 (s, 1H) 8.12 (m, 3H) 7.62 (m, 1H) 7.52 (m, 3H) 7.30 (s, 1H) 6.18 (d, 1H) 4.82 (m, 1H) 4.72 (m, 1H) 4.38 (d, 1H) 3.94 (m, 1H) 3.73 (d, 2H) 3.62 (m, 1H) 3.48 (m, 1H) 3.43 (s, 3H) 3.35 (m, 2H) 3.25 (m, 1H) 1.25 (d, 3H) 1.09 (d, 3H)

LCMS (method A), (M+H$^+$) 544.2, Rt=8.82 min.

Example 75

(S)-1-(4-(6-(5-fluoro-2-(methylsulfonyl)phenyl)-2-(3-methylmorpholino)pyrimidin-4-yl)phenyl)-3-(1-(hydroxymethyl)cyclobutyl)urea

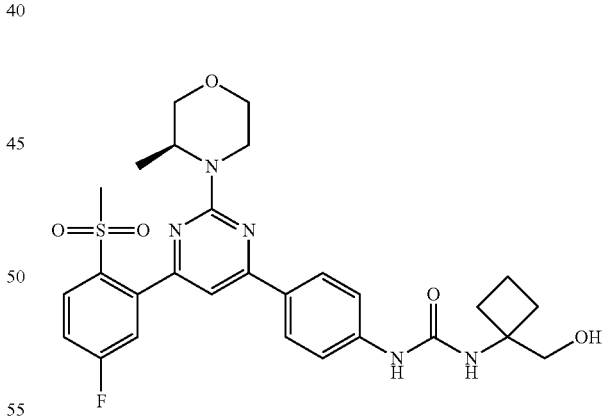

Method as described for example 58 using intermediate 32 (100 mg, 0.18 mmol) and (1-aminocyclobutyl)methanol (27 mg, 0.267 mmol). The reaction mixture was purified by prep HPLC at low pH to afford the title compound. (54 mg, 53%)

$^1$H NMR (d$_6$-DMSO) 9.02 (s, 1H) 8.12 (m, 3H) 7.62 (m, 1H) 7.55 (m, 1H) 7.49 (d, 2H) 7.30 (s, 1H) 6.55 (s, 1H) 4.87 (s, 1H) 4.72 (m, 1H) 4.36 (d, 1H) 3.94 (m, 1H) 3.73 (d, 1H) 3.62 (m, 1H) 3.54 (s, 2H) 3.47 (m, 1H) 3.43 (s, 3H) 3.25 (m, 1H) 2.29 (m, 2H) 1.99 (m, 2H) 1.82 (m, 1H) 1.69 (m, 1H) 1.25 (d, 3H)

LCMS (method A), (M+H$^+$) 570.2, Rt=9.54 min.

Example 76

1-(4-(6-(5-fluoro-2-(methylsulfonyl)phenyl)-2-((S)-3-methylmorpholino)pyrimidin-4-yl)phenyl)-3-((1S,2S)-2-hydroxycyclopentyl)urea

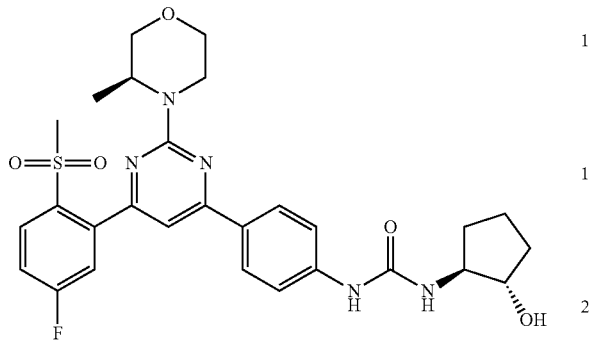

Method as described for example 58 using intermediate 32 (100 mg, 0.18 mmol) and (1S,2S)-2-aminocyclopentanol (27 mg, 0.267 mmol). The reaction mixture was purified by prep HPLC at low pH to afford the title compound. (50 mg, 49%)

$^1$H NMR (d$_6$-DMSO) 8.84 (s, 1H) 8.14 (m, 3H) 7.62 (m, 1H) 7.54 (m, 3H) 7.30 (s, 1H) 6.44 (d, 1H) 4.73 (m, 1H) 4.37 (d, 1H) 3.94 (m, 1H) 3.82 (m, 1H) 3.73 (m, 2H) 3.63 (m, 1H) 3.62 (m, 1H) 3.47 (m, 1H) 3.42 (s, 3H) 3.25 (m, 1H) 2.00 (m, 1H) 1.82 (m, 1H) 1.64 (m, 2H) 1.46 (m, 1H) 1.35 (m, 1H) 1.25 (d, 3H)

LCMS (method A), (M+H$^+$) 570.2, Rt=9.35 min.

Example 77

(S)-1-cyclopropyl-3-(4-(4-(5-fluoro-2-(methylsulfonyl)phenyl)-6-(3-methylmorpholino)pyrimidin-2-yl)phenyl)urea

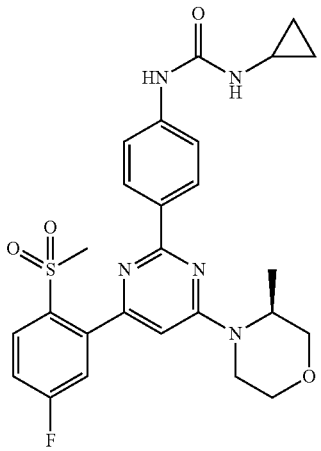 [SMILES: C[C@H]1COCCN1c1cc(-c2cc(F)ccc2S(C)(=O)=O)nc(-c2ccc(NC(=O)NC3CC3)cc2)n1]

Method as for example 58 using (S)-phenyl(4-(4-(5-fluoro-2-(methylsulfonyl)phenyl)-6-(3-methylmorpholino)pyrimidin-2-yl)phenyl)carbamate (intermediate 34) and cyclopropyl amine as starting materials. The solvent removed in vacuo and the crude material purified by prep HPLC at low pH to yield the title compound.

$^1$H NMR (d$_6$-DMSO) δ 8.58 (s, 1H), 8.19-8.11 (m, 3H), 7.64-7.53 (m, 2H), 7.49 (d, 2H), 6.82 (s, 1H), 6.48 (br d, 1H), 4.61-4.47 (br s, 1H), 4.36-4.20 (br s, 1H), 4.02-3.93 (dd, 1H), 3.76 (d, 1H), 3.68-3.60 (dd, 1H), 3.49 (s, 4H), 3.29-3.15 (m, 1H), 2.56-2.52 (m, 1H), 1.25 (d, 3H), 0.66-0.60 (m, 2H), 0.43-0.37 (m, 2H).

LCMS (method A) (M+H$^+$) 526; Rt=8.67 min.

Example 78

(S)-1-(4-(4-(5-fluoro-2-(methylsulfonyl)phenyl)-6-(3-methylmorpholino)pyrimidin-2-yl)phenyl)-3-(2-hydroxyethyl)urea

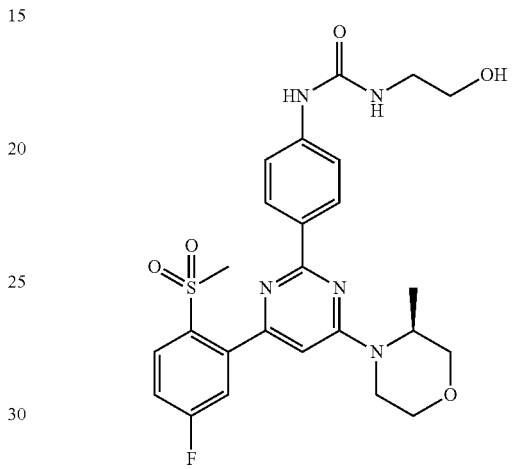

Method as for example 58 using (S)-phenyl(4-(4-(5-fluoro-2-(methylsulfonyl)phenyl)-6-(3-methylmorpholino)pyrimidin-2-yl)phenyl)carbamate (intermediate 34) as starting material. The solvent removed in vacuo and the crude material purified by prep HPLC at low pH to yield the title compound.

$^1$H NMR (d$_6$-DMSO) 8.83 (s, 1H), 8.18-8.11 (m, 3H), 7.64-7.53 (m, 2H), 7.47 (d, 2H), 6.81 (s, 1H), 6.80-6.24 (m, 1H), 4.82-4.70 (br s, 1H), 4.62-4.49 (br s, 1H), 4.34-4.21 (br s, 1H), 4.02-3.94 (dd, 1H), 3.76 (d, 1H), 3.68-3.60 (m, 1H), 3.49 (s, 3H), 3.47-3.41 (t, 2H), 3.27-3.19 (m, 1H), 3.19-3.12 (q, 2H), 1.25 (d, 3H).

LCMS (method A) (M+H$^+$) 530; Rt=7.29 min

Example 79

(S)-1-(4-(6-(5-fluoro-2-(methylsulfonyl)phenyl)-2-(3-methylmorpholino)pyrimidin-4-yl)phenyl)-3-(3-methoxycyclobutyl)urea

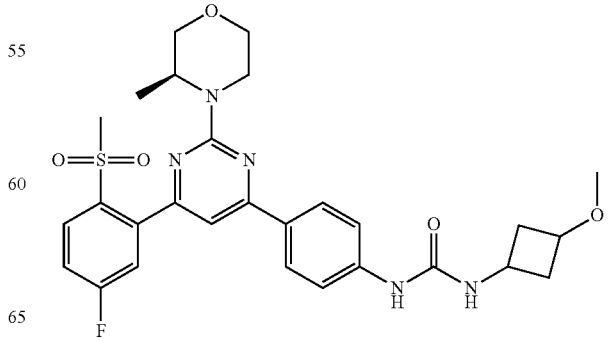

Method as described for example 58 using intermediate 32 (100 mg, 0.18 mmol) 3-methoxycyclobutanamine (22 mg, 0.213 mmol). The reaction mixture was purified by prep HPLC at low pH to afford the title compound. (37 mg, 30%)

$^1$H NMR (d$_6$-DMSO) 8.70 (d, 1H) 8.13 (m, 3H) 7.64 (m, 1H) 7.54 (m, 3H) 7.30 (s, 1H) 6.60 (m, 1H) 4.73 (m, 1H) 4.37 (d, 1H) 3.94 (m, 1H) 3.76 (m, 2H) 3.57 (m, 2H) 3.47 (m, 1H) 3.42 (s, 3H) 3.25 (m, 1H) 3.15 (s, 3H) 2.59 (m, 1H) 2.24 (m, 1H) 2.09 (m, 1H) 1.72 (m, 1H) 1.25 (d, 3H)

LCMS (method A), (M+H$^+$) 570.2, Rt=9.77 min.

Example 80

(S)-1-(2-hydroxyethyl)-3-(4-(4-(3-methylmorpholino)-6-(2-(methylsulfonyl)phenyl)pyrimidin-2-yl)phenyl)urea

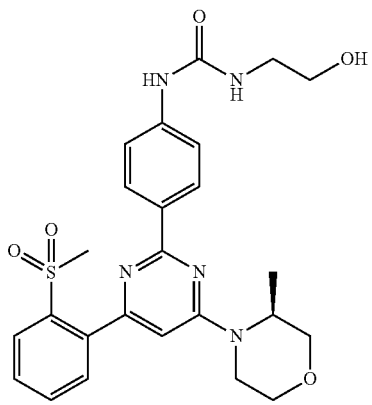 [SMILES: C[C@H]1COCCN1c1cc(-c2ccccc2S(C)(=O)=O)nc(-c2ccc(NC(=O)NCCO)cc2)n1]

Step 1.

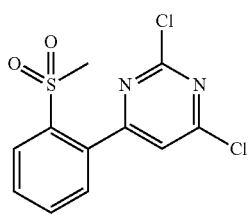 [SMILES: CS(=O)(=O)c1ccccc1-c1cc(Cl)nc(Cl)n1]

Method as intermediate 2 using 2,4,6-trichloropyrimidine and (2-(methylsulfonyl)phenyl)boronic acid as starting materials. The reaction mixture was partitioned between DCM and H$_2$O. The organic layer was recovered, dried with PTFE hydrophobic frit and the solvent removed in vacuo. The crude material was purified by flash chromatography using a gradient of 0-100% EtOAc in petrol ether. The relevant fractions were combined and the solvent removed in vacuo to yield the title compound as a brown gum (680 mg, 2.25 mmol, 21%).

LCMS (Method D) (M+H$^+$) 303, 305; Rt=1.02

Step 2.

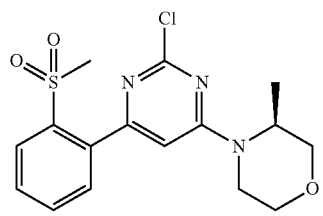 [SMILES: C[C@H]1COCCN1c1cc(-c2ccccc2S(C)(=O)=O)nc(Cl)n1]

Method as intermediates 1A and 1B using 2,4-dichloro-6-(2-(methylsulfonyl)phenyl)pyrimidine from step 1 as starting material. The reaction mixture's solvent was removed in vacuo. The crude material was purified by flash chromatography (silica) using a gradient of 0-100% EtOAc in petrol ether. The relevant fractions were combined and the solvent removed in vacuo to yield the title compound as a pale yellow solid.

LCMS (method D) (M+H$^+$) 368, 370; Rt=1.02 min

Step 3.

Method as described for intermediate 33 using (S)-4-(2-chloro-6-(2-(methylsulfonyl)phenyl)pyrimidin-4-yl)-3-methylmorpholine from step 2 and 1-(2-hydroxyethyl)-3-(4-(4,4,5,5-tetramethyl-1,3,2-dioxaborolan-2-yl)phenyl)urea (intermediate 18) as starting materials. The reaction mixture was partitioned between DCM and H$_2$O. The organic layer was recovered, dried over hydrophobic frit and the solvent removed in vacuo. The crude material was purified prep HPLC at low pH to yield the title compound as a off white solid.

$^1$H NMR (d$_6$-DMSO) 8.85 (s, 1H), 8.16 (d, 2H), 8.10-8.06 (dd, 1H), 7.87-7.80 (m, 1H), 7.78-7.72 (m, 1H), 7.68-7.58 (dd, 1H), 7.46 (d, 2H), 6.76 (s, 1H), 6.30 (t, 1H), 4.80-4.70 (br s, 1H), 4.62-4.49 (br s, 1H), 4.34-4.23 (br s, 1H), 4.0-3.93 (dd, 1H), 3.76 (d, 1H), 3.70-3.61 (m, 1H), 3.55-3.49 (m, 1H), 3.48 (s, 3H), 3.45-3.39 (m, 2H), 3.27-3.19 (m, 1H), 3.19-3.11 (q, 3H), 1.24 (s, 3H).

LCMS (method A) (M+H$^+$) 512; Rt=6.28 min

Example 81

1-(4-(2-(8-oxa-3-azabicyclo[3.2.1]octan-3-yl)-6-(5-fluoro-2-(methylsulfonyl)phenyl)pyrimidin-4-yl)phenyl)-3-cyclopropylurea

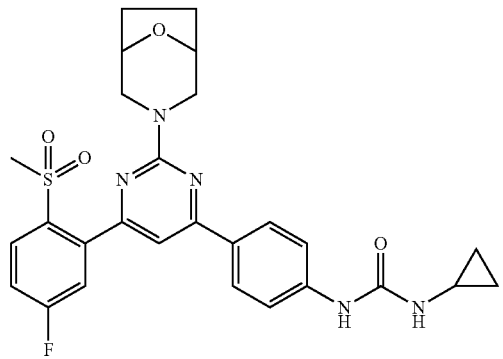 [SMILES: CS(=O)(=O)c1ccc(F)cc1-c1cc(-c2ccc(NC(=O)NC3CC3)cc2)nc(N2CC3CCC(C2)O3)n1]

Step 1.

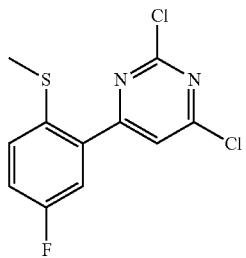 [SMILES: CSc1ccc(F)cc1-c1cc(Cl)nc(Cl)n1]

2,4,6-trichloropyrimidine (1 g, 5.50 mmol), (5-fluoro-2-(methylthio)phenyl)boronic acid (1.12 g, 6.05 mmol), Pd(PPh$_3$)$_2$Cl$_2$.DCM (224 mg, 0.27 mmol) and Na$_2$CO$_3$ (873 mg, 8.24 mmol) were dissolved in a mixture of DME:H$_2$O (4:1) and stirred at 120° C. under microwave for 30 mins. The reaction mixture was partitioned between DCM and H$_2$O. The organic layer was recovered, dried with PTFE hydrophobic frit and the solvent removed in vacuo. The crude material was purified by flash chromatography (silica) using a gradient of 0-30% EtOAc in petrol ether. The relevant fractions were combined and the solvent removed in vacuo to yield the title compound as a yellow solid (565 mg, 1.96 mmol, 35%).

Step 2

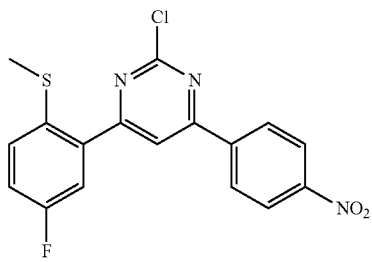 [SMILES: CSc1ccc(F)cc1-c1cc(-c2ccc([N+](=O)[O-])cc2)nc(Cl)n1]

Method as for example 34 using 2,4-dichloro-6-(5-fluoro-2-(methylthio)phenyl)pyrimidine from step 1 and (4-nitrophenyl)boronic acid as starting materials and heating by microwave at 100° C. for 1 hr. After work up purified by flash chromatography (silica) eluting 20-50% Ethyl acetate/Petroleum Ether to yield a yellow solid (270 mg 34%).

LCMS (method D) (M+H$^+$) 376; Rt=1.31 min.

Step 3.

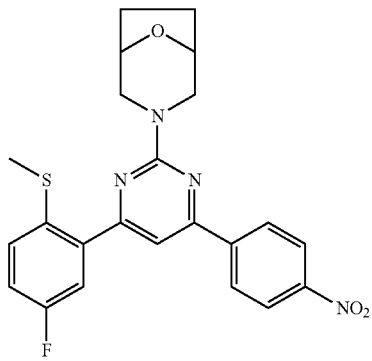 [SMILES: CSc1ccc(F)cc1-c1cc(-c2ccc([N+](=O)[O-])cc2)nc(N2CC3CCC(C2)O3)n1]

2-chloro-4-(5-fluoro-2-(methylthio)phenyl)-6-(4-nitrophenyl)pyrimidine (from step 2) (270 mg, 0.72 mmol) was dissolved in DMF (3 mL) and stirred with 8-oxa-3-azabicyclo[3.2.1]octane hydrochloride (196 mg, 1.31 mmol) and NEt$_3$ (224 uL, 1.6 mmol) at 50° C. overnight. The reaction mixture was partitioned between H$_2$O and Ethyl acetate. The organic layer was recovered and washed with brine and dried over Na$_2$SO$_4$, filtered and the solvent removed in vacuo. The crude material was purified by reverse phase chromatography using a gradient of 0-72% Acetonitrile in water with 0.1% formic acid. The relevant fractions were combined and the solvent removed in vacuo to yield the title compound as a yellow solid (48 mg, 16%).

$^1$H NMR (d$_6$-DMSO) δ 8.56-8.43 (m, 2H), 8.43-8.30 (m, 2H), 7.74-7.61 (m, 2H), 7.49 (dd, 1H), 7.43-7.33 (m, 1H), 4.45 (br d, 4H), 3.20 (d, 2H), 2.42 (s, 3H), 1.91-1.81 (m, 2H), 1.78-1.68 (m, 2H).

LCMS (method D) (M+H$^+$) 453; Rt=1.36 min.

Step 4.

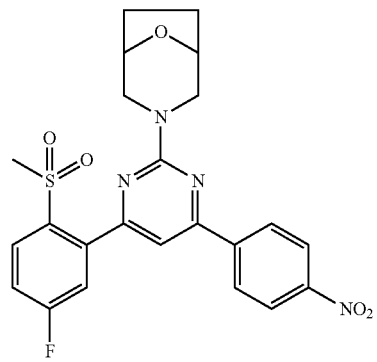

Method as per Intermediate 6. After quenching the reaction mixture was partitioned between 1M NaOH and DCM, the organic layer was recovered, dried with PTFE hydrophobic frit and the solvent removed in vacuo to yield the title compound as a yellow solid (109 mg, quantitative yield).

LCMS (method D) (M+H$^+$) 485; Rt=1.2 min.

Step 5.

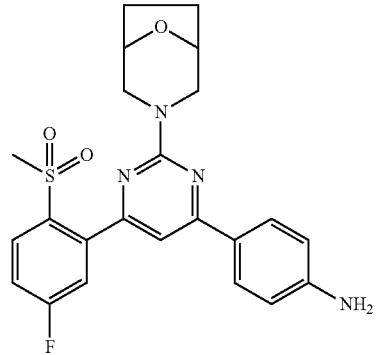 [SMILES: CS(=O)(=O)c1ccc(F)cc1-c1cc(-c2ccc([N+](=O)[O-])cc2)nc(N2CC3CCC(C2)O3)n1]

The product from step 4 (3-(4-(5-fluoro-2-(methylsulfonyl)phenyl)-6-(4-nitrophenyl)pyrimidin-2-yl)-8-oxa-3-azabicyclo[3.2.1]octane) (109 mg, 0.225 mmol) was dissolved in ethanol (10 mL), Palladium on activated carbon (20 mg) was added and the reaction mixture stirred at room temperature under hydrogen for 2.5 hours. The reaction mixture was filtered and evaporated and used without further purification in step 5.

LCMS (method UPLC-low pH) (M+H$^+$) 455; Rt=1.06 min.

Step 6.

The product from step 5 (4-(2-(8-oxa-3-azabicyclo[3.2.1]octan-3-yl)-6-(5-fluoro-2-(methylsulfonyl)phenyl)pyrimidin-4-yl)aniline) (93 mg, 0.2 mmol) was dissolved in dry DCM (2 mL) to this was added cyclopropyl isocyanate (26 mg, 0.3 mmol) and the reaction mixture stirred at room temperature overnight. The reaction mixture was partitioned between DCM and water and the organic layer was collected and washed with brine, dried over $Na_2SO_4$, filtered and the solvent removed in vacuo. The resulting yellow solid was purified by prep-HPLC at low pH to give a white solid (14.5 mg, 14%)

$^1$H NMR ($d_6$-DMSO) δ 8.65 (s, 1H), 8.18-8.06 (m, 3H), 7.64-7.58 (m, 1H), 7.58-7.52 (m, 3H), 7.30 (s, 1H), 6.50 (d, 1H), 4.43 (br s, 2H), 4.28 (br s, 2H), 3.44 (s, 3H), 3.14 (dd, 2H), 2.60-2.51 (m, 1H), 1.87-1.79 (m, 2H), 1.74-1.65 (m, 2H), 0.69-0.60 (m, 2H), 0.45-0.36 (m, 2H).

LCMS (method A) (M+H$^+$) 538; Rt=9.65 min.

Example 82

1-(4-(6-(5-fluoro-2-(methylsulfonyl)phenyl)-2-((S)-3-methylmorpholino)pyrimidin-4-yl)phenyl)-3-(R)-2-hydroxypropyl)urea

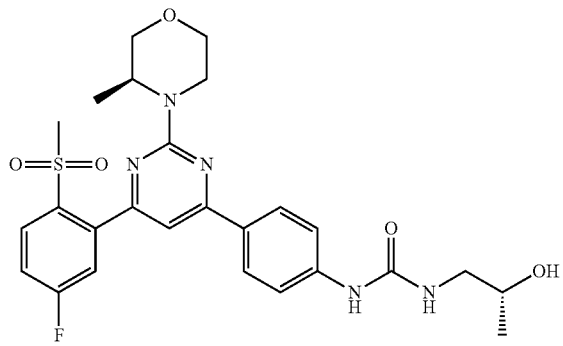 [SMILES: C[C@@H](O)CNC(=O)Nc1ccc(-c2cc(-c3cc(F)ccc3S(C)(=O)=O)nc(N3CCOC[C@@H]3C)n2)cc1]

Method as described for example 58 using intermediate 34 (100 mg, 0.18 mmol) (R)-1-aminopropan-2-ol (16 mg, 0.213 mmol). The reaction mixture was purified by prep HPLC at low pH to afford the title compound. (36 mg, 37%)

$^1$H NMR ($d_6$-DMSO) 8.95 (s, 1H) 8.14 (m, 3H) 7.64 (m, 1H) 7.54 (m, 3H) 7.30 (s, 1H) 6.32 (t, 1H) 4.75 (m, 2H) 4.37 (d, 1H) 3.95 (m, 1H) 3.68 (m, 3H) 3.48 (m, 1H) 3.43 (s, 3H) 3.25 (m, 1H) 3.15 (m, 1H) 2.95 (m, 1H) 1.25 (d, 3H) 1.09 (d, 3H)

LCMS (method A), (M+H$^+$) 544.2, Rt=8.88 min.

Example 83

1-(4-(6-(5-fluoro-2-(methylsulfonyl)phenyl)-2-((S)-3-methylmorpholino)pyrimidin-4-yl)phenyl)-3-((S)-2-hydroxypropyl)urea

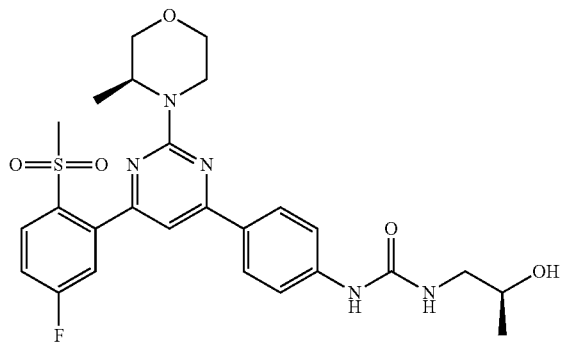 [SMILES: C[C@H](O)CNC(=O)Nc1ccc(-c2cc(-c3cc(F)ccc3S(C)(=O)=O)nc(N3CCOC[C@@H]3C)n2)cc1]

Method as described for example 58 using intermediate 34 (100 mg, 0.18 mmol) and (S)-1-aminopropan-2-ol (16 mg, 0.213 mmol). The reaction mixture was purified by prep HPLC at low pH to afford the title compound. (35 mg, 36%)

$^1$H NMR ($d_6$-DMSO) 8.95 (s, 1H) 8.14 (m, 3H) 7.64 (m, 1H) 7.54 (m, 3H) 7.30 (s, 1H) 6.33 (t, 1H) 4.75 (m, 2H) 4.37 (d, 1H) 3.95 (m, 1H) 3.68 (m, 3H) 3.48 (m, 1H) 3.43 (s, 3H) 3.25 (m, 1H) 3.15 (m, 1H) 2.95 (m, 1H) 1.25 (d, 3H) 1.09 (d, 3H)

LCMS (method A), (M+H$^+$) 544.2, Rt=8.86 min.

Example 84

(S)-1-(2-aminoethyl)-3-(4-(6-(5-fluoro-2-(methylsulfonyl)phenyl)-2-(3-methylmorpholino)pyrimidin-4-yl)phenyl)urea

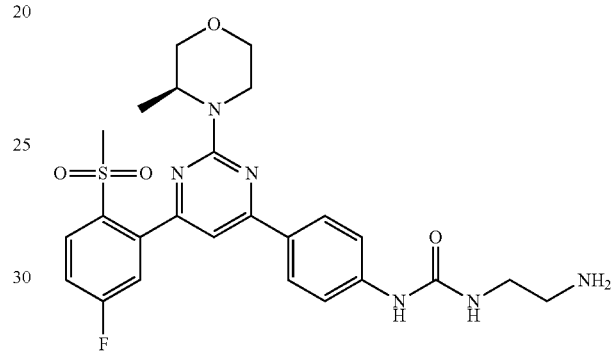

Method as described for example 58 using intermediate 34 (100 mg, 0.18 mmol) and ethane-1,2-diamine (13 mg, 0.213 mmol). The reaction mixture was purified by prep HPLC at low pH to afford the title compound. (11 mg, 12%)

$^1$H NMR ($d_6$-DMSO) 9.80 (s, 1H) 8.22 (s, 2H) 7.93 (m, 3H) 7.56 (s, 1H) 7.40 (m, 4H) 7.10 (s, 1H) 4.52 (m, 1H) 4.17 (d, 1H) 3.74 (m, 1H) 3.53 (d, 1H) 3.42 (m, 1H) 3.26 (m, 1H) 3.23 (s, 3H) 3.10 (m, 2H) 3.07 (m, 1H) 2.66 (m, 2H) 1.05 (d, 3H)

LCMS (method A), (M+H$^+$) 529.2, Rt=5.95 min.

Example 85

(S)—N-(2-(3-(4-(6-(5-fluoro-2-(methylsulfonyl)phenyl)-2-(3-methylmorpholino)pyrimidin-4-yl)phenyl)ureido)ethyl)acetamide

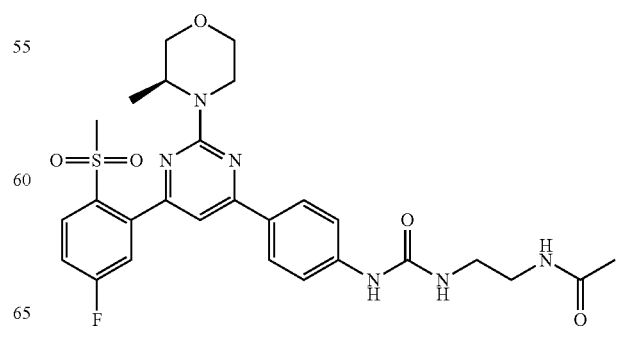

Method as described for example 58 using intermediate 34 (100 mg, 0.18 mmol) and N-(2-aminoethyl)acetamide (22 mg, 0.213 mmol). The reaction mixture was purified by prep HPLC at low pH to afford the title compound. (38 mg, 37%)

¹H NMR (d₆-DMSO) 8.91 (s, 1H) 8.14 (m, 3H) 7.95 (m, 1H) 7.64 (m, 1H) 7.54 (m, 3H) 7.30 (s, 1H) 6.31 (m, 1H) 4.72 (m, 1H) 4.37 (d, 1H) 3.94 (m, 1H) 3.74 (m, 1H) 3.63 (m, 1H) 3.47 (m, 1H) 3.42 (s, 3H) 3.25 (m, 1H) 3.15 (m, 4H) 1.83 (s, 3H) 1.25 (d, 3H)

LCMS (method A), (M+H⁺) 571.2, Rt=8.48 min.

Example 86

(S)-1-(4-(6-(5-fluoro-2-(methylsulfonyl)phenyl)-2-(3-methylmorpholino)pyrimidin-4-yl)phenyl)-3-(oxetan-3-yl)urea

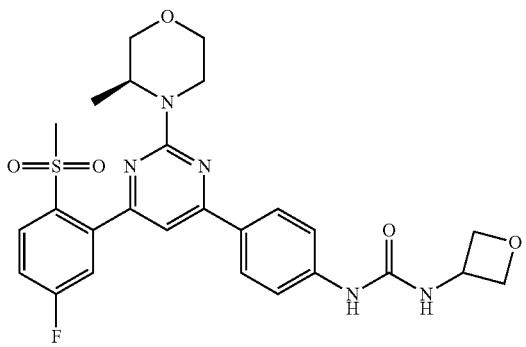 [SMILES: C[C@H]1COCCN1c1nc(-c2ccc(NC(=O)NC3COC3)cc2)cc(-c2cc(F)ccc2S(C)(=O)=O)n1]

Method as described for example 58 using intermediate 34 (100 mg, 0.18 mmol) and oxetan-3-amine (16 mg, 0.213 mmol). The reaction mixture was purified by prep HPLC at low pH. This was further purified using a TsOH cartridge, washing with MeOH, eluting desired material with 2M NH₃ in methanol and concentrating in vacuo to afford the title compound. (20 mg, 21%)

¹H NMR (d₆-DMSO) 9.52 (s, 1H) 8.14 (m, 3H) 7.64 (m, 4H) 7.30 (s, 1H) 4.75 (m, 2H) 4.37 (m, 2H) 4.12 (s, 1H) 3.94 (m, 1H) 3.75 (d, 1H) 3.62 (m, 1H) 3.47 (m, 2H) 3.42 (s, 3H) 3.35 (m, 2H) 3.25 (m, 1H) 1.25 (d, 3H)

LCMS (method A), (M+H⁺) 542.2, Rt=6.41 min.

Example 87

(S)-1-cyclopropyl-3-(4-(6-(2-(ethylsulfonyl)phenyl)-2-(3-methylmorpholino)pyrimidin-4-yl)phenyl)urea

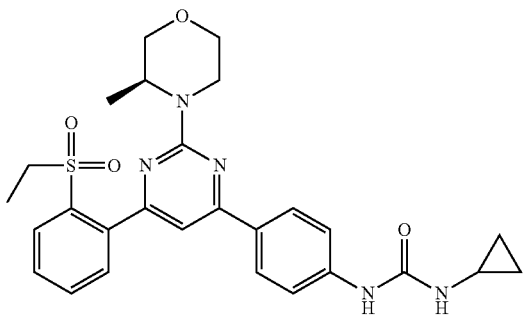 [SMILES: CCS(=O)(=O)c1ccccc1-c1cc(-c2ccc(NC(=O)NC3CC3)cc2)nc(N2CCOC[C@@H]2C)n1]

(S)-1-(4-(6-chloro-2-(3-methylmorpholino)pyrimidin-4-yl)phenyl)-3-cyclopropylurea (intermediate 22), (80 mg, 0.2 mmol), 2-ethylsulfonylphenylboronic acid (64 mg, 0.3 mmol), Sodium carbonate (64 mg, 0.6 mmol) and Bis(diphenylphosphino)-Ferrocenedichloropalladium(II)-DCM-complex (8 mg, 0.01 mmol) in DME/EtOH/Water (7:3:2) were irradiated in a Biotage microwave for 45 minutes at 100° C. The reaction mixture was diluted with DCM (5 mL), washed with water (5 mL), organic layer concentrated in vacuo, residue dissolved in DMSO, filtered and purified by prep HPLC (low pH) to afford a brown solid. This was further purified using a TsOH cartridge, washing with MeOH, eluting desired material with 2M NH₃ in methanol and concentrating in vacuo to afford a brown solid, 57 mg, 55%.

¹H NMR (d₆-DMSO) 8.64 (s, 1H), 8.13 (d, 2H), 8.04 (d, 1H), 7.86 (dd, 1H), 7.77 (dd, 1H), 7.62 (d, 1H), 7.55 (d, 2H), 7.25 (1H, s), 6.50 (d, 1H), 4.75-4.66 (m, 1H), 4.35 (d, 1H), 3.95 (d, 1H), 3.74 (d, 1H), 3.65-3.41 (m, 5H), 3.23 (dd, 1H), 2.59-2.52 (m, 1H), 1.25 (d, 3H), 1.18 (t, 3H), 1.07 (t, 3H), 0.67-0.63 (m, 2H), 0.44-0.40 (m, 2H).

LCMS (method A), (M+H⁺) 522, Rt=9.89 min.

Example 88

(S)-1-cyclopropyl-3-(4-(2-(3-methylmorpholino)-6-(2-(pyrrolidin-1-ylsulfonyl)phenyl)pyrimidin-4-yl)phenyl)urea

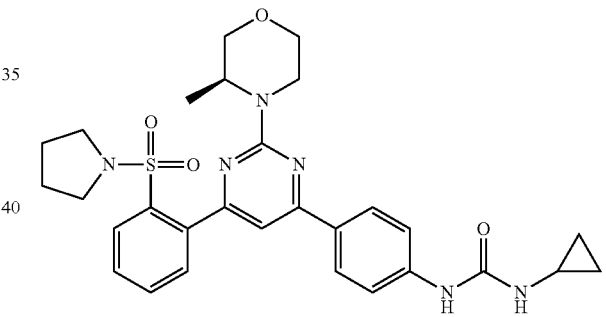

(S)-1-(4-(6-chloro-2-(3-methylmorpholino)pyrimidin-4-yl)phenyl)-3-cyclopropylurea (intermediate 22), (80 mg, 0.2 mmol), 2-(pyrrolidinylsulfonyl)phenylboronic acid (77 mg, 0.3 mmol), Sodium carbonate (64 mg, 0.6 mmol) and Bis (diphenylphosphino)-Ferrocenedichloropalladium(II)-DCM-complex (8 mg, 0.01 mmol) in DME/EtOH/Water (7:3:2) were irradiated in a Biotage microwave for 45 minutes at 100° C. The reaction mixture was diluted with DCM (5 mL), washed with water (5 mL), organic layer concentrated in vacuo, residue dissolved in DMSO, filtered and purified by prep HPLC (low pH) to afford an orange solid. This was further purified using a TsOH cartridge, washing with MeOH, eluting desired material with 2M NH₃ in methanol and concentrating in vacuo to afford a brown solid, 22 mg, 20%.

¹H NMR (d₆-DMSO) 8.64 (s, 1H), 8.05 (d, 2H), 7.96 (d, 1H), 7.75 (dd, 1H), 7.69 (dd, 1H), 7.56-7.51 (m, 3H), 7.22 (s, 1H), 6.50 (d, 1H), 4.81-4.72 (m, 1H), 4.40 (d, 1H), 3.95 (d, 1H), 3.74 (d, 1H), 3.60 (d, 1H), 3.45 (dd, 1H), 3.21 (dd, 1H), 3.10-3.01 (m, 4H), 1.70-1.66 (m, 4H), 1.23 (d, 3H), 0.67-0.63 (m, 2H), 0.44-0.40 (m, 2H).

LCMS (method A), (M+H⁺) 563, Rt=10.44 min.

Biological Assays
Determination of the Effect of the Compounds According to the Invention on mTOR The compounds of the present invention as described were tested in the mTOR kinobeads assay as described below. Briefly, test compounds (at various concentrations) and the affinity matrix (1:1 mixture of beads with immobilized phenylthiazole ligand 1 and beads with immobilized phenylmorpholin-chromen ligand; WO 2009/098021) were added to cell lysate aliquots and allowed to bind to the proteins in the lysate sample. After the incubation time the beads with captured proteins were separated from the lysate. Bound proteins were then eluted and the presence of mTOR, PI3K delta (PI3 Kd) and DNA-dependent protein kinase (DNA-PK) was detected and quantified using a specific antibody in a dot blot procedure and the Odyssey infrared detection system. Dose response curves for individual kinases were generated and $IC_{50}$ values calculated. Kinobeads assays for PI3 kinases (WO-A 2008/015013) and for kinase selectivity profiling (WO 2009/098021) have been previously described.

Washing of Affinity Matrix

The affinity matrix (beads with immobilized phenylmorpholin-chromen ligand) was washed two times with 15 ml of 1×DP buffer containing 0.2% NP40 (IGEPAL® CA-630, Sigma, #13021) and then resupended in 5.5 ml of 1×DP buffer containing 0.2% NP40 (10% beads slurry).

5×DP buffer: 250 mM Tris-HCl pH 7.4, 25% Glycerol, 7.5 mM $MgCl_2$, 750 mM NaCl, 5 mM $Na_3VO_4$, filter the 5×-lysis buffer through 0.22 μm filter and store in aliquots at −80° C. The 5×DP buffer is diluted to 1×DP buffer containing 1 mM DTT and 25 mM NaF.

Preparation of Test Compounds

Stock solutions of test compounds were prepared in DMSO. In a 96 well plate 30 μl solution of diluted test compounds at 5 mM in DMSO were prepared. Starting with this solution a 1:3 dilution series (9 steps) was prepared. For control experiments (no test compound) a buffer containing 2% DMSO was used. Compound CZC00018052 served as a positive control (PI-103; Calbiochem catalogue number 528100).

Cell Culture and Prepartion of Cell Lysates

Jurkat cells (ATCC catalogue number TIB-152 Jurkat, clone E6-1) were grown in 1 litre Spinner flasks (Integra Biosciences, #182101) in suspension in RPMI 1640 medium (Invitrogen, #21875-034) supplemented with 10% Fetal Bovine Serum (Invitrogen) at a density between $0.15 \times 10^6$ and $1.2 \times 10^6$ cells/ml. Cells were harvested by centrifugation, washed once with 1×PBS buffer (Invitrogen, #14190-094) and cell pellets were frozen in liquid nitrogen and subsequently stored at −80° C.

Jurkat cells were homogenized in a Potter S homogenizer in lysis buffer: 50 mM Tris-HCl, 0.8% NP40, 5% glycerol, 150 mM NaCl, 1.5 mM $MgCl_2$, 25 mM NaF, 1 mM sodium vanadate, 1 mM DTT, pH 7.5. One complete EDTA-free tablet (protease inhibitor cocktail, Roche Diagnostics, 1873580) per 25 ml buffer was added. The material was dounced 10 times using a mechanized POTTER S, transferred to 50 ml falcon tubes, incubated for 30 minutes on ice and spun down for 10 min at 20,000 g at 4° C. (10,000 rpm in Sorvall SLA600, precooled). The supernatant was transferred to an ultracentrifuge (UZ)-polycarbonate tube (Beckmann, 355654) and spun for 1 hour at 100.000 g at 4° C. (33.500 rpm in Ti50.2, precooled). The supernatant was transferred again to a fresh 50 ml falcon tube, the protein concentration was determined by a Bradford assay (BioRad) and samples containing 50 mg of protein per aliquot were prepared. The samples were immediately used for experiments or frozen in liquid nitrogen and stored frozen at −80° C.

Dilution of Cell Lysate

Jurkat cell lysate (approximately 50 mg protein per plate) was thawed in a water bath at room temperature and then kept on ice. To the thawed cell lysate 1×DP 0.8% NP40 buffer containing protease inhibitors (1 tablet for 25 ml buffer; EDTA-free protease inhibitor cocktail; Roche Diagnostics 1873580) was added in order to reach a final protein concentration of 5 mg/ml total protein. The diluted cell lysate was stored on ice.

Incubation of Lysate with Test Compound and Affinity Matrix

To a 96 well filter plate (Multiscreen HTS, BV Filter Plates, Millipore #MSBVN1250) were added per well: 50 μl affinity matrix (10% beads slurry), 3 μl of compound solution, and 100 μl of cell diluted lysate. Plates were sealed and incubated for two hours in a cold room on a Thermoxer with shaking (750 rpm). Afterwards the plate was washed twice with 230 μl washing buffer (1×DP 0.4% NP40). The filter plate was placed on top of a collection plate (Greiner bio-one, PP-microplate 96 well V-shape, 65120) and the beads were then eluted with 20 μl of sample buffer (100 mM Tris, pH 7.4, 4% SDS, 0.00025% Bromophenol blue, 20% glycerol, 50 mM DTT). The eluate was frozen quickly at −80° C. and stored at −20° C.

Detection and Quantification of Eluted Kinases

The kinases in the eluates were detected and quantified by spotting on Nitrocellulose membranes and using a first antibody directed against the kinase of interest and a fluorescently labelled secondary antibody (anti-mouse or anti-rabbit IRDye™ antibodies from Rockland). The Odyssey Infrared Imaging system from LI-COR Biosciences (Lincoln, Nebr., USA) was operated according to instructions provided by the manufacturer (Schutz-Geschwendener et al., 2004. Quantitative, two-color Western blot detection with infrared fluorescence. Published May 2004 by LI-COR Biosciences, www.licor.com).

After spotting of the eluates the nitrocellulose membrane (BioTrace NT; PALL, #BTNT30R) was first blocked by incubation with Odyssey blocking buffer (LICOR, 927-40000) for one hour at room temperature. Blocked membranes were then incubated for 16 hours at 25° C. with the first antibody diluted in Odyssey blocking buffer (LICOR #927-40000). Afterwards the membrane was washed three times for 10 minutes with PBS buffer containing 0.1% Tween 20 at room temperature. Then the membrane was incubated for 60 minutes at room temperature with the detection antibody (IRDye™ labelled antibody from Rockland) diluted in Odyssey blocking buffer (LICOR #927-40000). Afterwards the membrane was washed three times for 10 minutes each with 1×PBS buffer containing 0.1% Tween 20 at room temperature. Then the membrane was rinsed once with PBS buffer to remove residual Tween 20. The membrane was kept in PBS buffer at 4° C. and then scanned with the Odyssey instrument. Fluorescence signals were recorded and analysed according to the instructions of the manufacturer.

TABLE 1

Sources and dilutions of antibodies

| Target kinase | Primary antibody (dilution) | Temperature of Primary incubation | Secondary antibody (dilution) |
|---|---|---|---|
| mTOR | Cell signaling #2972 (1:500) | Room Temperature | Licor anti-rabbit 800 (1:5000) |

TABLE 1-continued

Sources and dilutions of antibodies

| Target kinase | Primary antibody (dilution) | Temperature of Primary incubation | Secondary antibody (dilution) |
|---|---|---|---|
| PI3Kdelta | Santa Cruz #sc-7176 (1:1000) | 4° C. | Licor anti-rabbit 800 (1:2500) |
| DNAPK | Calbiochem #NA57 (1:1000) | 4° C. | Licor anti-mouse 800 (1:5000) |

Results

TABLE 2

Inhibition values ($IC_{50}$ in μM) as determined in the kinobeads assay
(Activity level: A < 0.1 μM; 0.1 μM ≤ B < 1 μM; 1 μM ≤ C < 10 μM; D ≥ 10 μM).

| Example Number | mTor | PI3Kd | DNAPK |
|---|---|---|---|
| 1 | C | D | D |
| 2 | B | D | D |
| 3 | B | D | D |
| 4 | B | D | D |
| 5 | C | D | D |
| 6 | B | D | D |
| 7 | C | D | D |
| 8 | C | D | D |
| 9 | C | D | D |
| 10 | C | D | D |
| 11 | C | D | D |
| 12 | C | D | D |
| 13 | C | D | D |
| 14 | B | D | D |
| 15 | C | D | D |
| 16 | C | D | D |
| 17 | C | D | D |
| 18 | C | D | D |
| 19 | C | D | D |
| 20 | C | D | D |
| 21 | B | D | D |
| 22 | C | D | D |
| 23 | B | D | D |
| 24 | B | D | D |
| 25 | B | D | D |
| 26 | B | D | C |
| 27 | C | C | C |
| 28 | C | D | D |
| 29 | C | D | C |
| 30 | C | C | C |
| 31 | C | D | C |
| 32 | C | D | C |
| 33 | C | C | C |
| 34 | C | D | D |
| 35 | B | D | D |
| 36 | C | D | C |
| 37 | C | D | D |
| 38 | C | D | D |
| 39 | C | D | D |
| 40 | B | D | D |
| 41 | A | D | D |
| 42 | B | D | D |
| 43 | B | D | D |
| 44 | B | D | D |
| 45 | A | C | D |
| 46 | B | D | D |
| 47 | B | D | D |
| 48 | B | D | C |
| 49 | B | D | C |
| 50 | A | D | C |
| 51 | B | D | C |
| 52 | B | D | C |
| 53 | B | D | D |
| 54 | B | D | D |
| 55 | B | D | D |
| 56 | C | D | D |
| 57 | C | D | D |
| 58 | C | D | D |
| 59 | C | D | D |
| 60 | B | D | D |
| 61 | B | D | D |
| 62 | B | D | D |
| 63 | C | D | D |
| 64 | B | D | D |
| 65 | B | D | D |
| 66 | C | D | D |
| 67 | C | D | D |
| 68 | C | D | D |
| 69 | C | D | D |
| 70 | C | D | D |
| 71 | B | D | D |
| 72 | B | D | D |

TABLE 3

Sources and dilutions of antibodies

| Target kinase | Primary antibody (dilution) | Temperature of primary incubation | Secondary antibody (dilution) |
|---|---|---|---|
| PI3K alpha | Cell Signalling Technologies 4255 (1 in 100) | 25° C. | Anti-Rabbit (1 in 2500) |
| PI3K beta | Millipore 04-400 (1 in 1000) | 25° C. | Anti-Rabbit (1 in 2500) |
| PI3K delta | Santa Cruz SC7176 (1 in 1000) | 4° C. | Anti-Rabbit (1 in 2500) |
| PI3K gamma | Jena Bioscience ABD-026L (1 in 100) | 25° C. | Anti-Mouse (1 in 2500) |
| mTOR | Cell Signalling Technologies 2972 (1 in 500) | 25° C. | Anti-Rabbit (1 in 5000) |
| DNAPK | Calbiochem NA57 (1 in 1000) | 4° C. | Anti-Mouse (1 in 5000) |

As shown in Table 4, the selectivity of compounds of the invention was further determined versus DNA-dependent protein kinase (DNA-PK), PI3Kα, PI3Kβ, PI3Kδ, and PI3Kγ.

TABLE 4

Inhibition values ($IC_{50}$ in μM) as determined in the kinobeads assay

| Example Number. | mTOR | DNAPK | PI3Ka | PI3Kb | PI3Kd | PI3Kg |
|---|---|---|---|---|---|---|
| 1 | C | D | — | — | D | — |
| 2 | B | D | D | D | D | D |
| 3 | B | D | D | D | D | D |
| 4 | B | D | D | D | D | D |
| 5 | C | D | — | — | D | — |
| 6 | B | D | D | D | D | D |
| 7 | C | D | D | D | D | D |
| 8 | C | D | — | — | D | — |
| 9 | C | D | — | — | D | — |
| 10 | C | D | — | — | D | — |
| 11 | C | D | — | — | D | — |
| 12 | C | D | — | — | D | — |
| 13 | C | D | — | — | D | — |
| 14 | B | D | D | D | D | D |
| 15 | C | D | D | D | D | D |
| 16 | C | D | — | — | D | — |
| 17 | C | D | — | — | D | — |
| 18 | C | D | — | — | D | — |

TABLE 4-continued

Inhibition values (IC$_{50}$ in μM) as determined in the kinobeads assay

| Example Number. | mTOR | DNAPK | PI3Ka | PI3Kb | PI3Kd | PI3Kg |
|---|---|---|---|---|---|---|
| 19 | C | D | — | — | D | — |
| 20 | C | D | — | — | D | — |
| 21 | B | D | D | D | D | D |
| 22 | C | D | — | — | D | — |
| 23 | B | D | D | D | D | D |
| 24 | B | D | D | D | D | D |
| 25 | B | D | D | D | D | D |
| 26 | B | C | D | C | D | D |
| 27 | C | C | — | — | C | — |
| 28 | C | D | D | D | D | D |
| 29 | B | C | C | C | D | D |
| 30 | C | C | C | C | C | D |
| 31 | C | C | — | — | D | — |
| 32 | C | C | — | — | D | — |
| 33 | C | C | — | — | C | — |
| 34 | C | D | — | — | D | — |
| 35 | B | D | D | D | D | D |
| 36 | C | C | — | — | D | — |
| 37 | B | D | D | D | D | D |
| 38 | C | D | D | D | D | D |
| 39 | C | D | D | D | D | D |
| 40 | B | D | D | D | D | D |
| 41 | A | D | D | D | D | D |
| 42 | B | D | D | D | D | D |
| 43 | B | D | D | D | D | D |
| 44 | B | D | D | D | D | D |
| 45 | A | D | C | C | C | D |
| 46 | B | D | D | D | D | D |
| 47 | B | D | D | D | D | D |
| 48 | B | C | D | D | D | D |
| 49 | B | C | D | D | D | D |
| 50 | A | C | D | D | D | D |
| 51 | B | C | D | D | D | D |
| 52 | B | C | D | D | D | D |
| 53 | B | D | C | D | D | D |
| 54 | B | D | D | D | D | D |
| 55 | B | D | D | D | D | D |
| 56 | C | D | D | D | D | D |
| 57 | C | D | D | D | D | D |
| 58 | C | D | D | D | D | D |
| 59 | C | D | D | D | D | D |
| 60 | B | D | D | D | D | D |
| 61 | B | C | D | D | D | D |
| 62 | B | D | D | D | D | D |
| 63 | C | D | D | D | D | D |
| 64 | B | D | D | D | D | D |
| 65 | B | D | D | D | D | D |
| 66 | C | D | D | D | D | D |
| 67 | C | D | D | D | D | D |
| 68 | C | D | D | D | D | D |
| 69 | C | D | D | D | D | D |
| 70 | C | D | D | D | D | D |
| 71 | B | D | D | D | D | D |
| 72 | B | D | D | D | D | D |
| 73 | B | D | D | D | D | D |
| 74 | B | D | D | D | D | D |
| 75 | B | D | D | D | D | D |
| 76 | B | D | D | D | D | D |
| 77 | B | D | D | D | D | D |
| 78 | A | D | D | D | D | D |
| 79 | C | D | D | D | D | D |
| 80 | A | D | D | D | D | D |
| 81 | B | D | D | D | D | D |
| 82 | C | D | D | D | D | D |
| 83 | B | D | D | D | D | D |
| 84 | B | D | D | D | D | D |
| 85 | C | D | D | D | D | D |
| 86 | B | D | D | D | D | D |
| 87 | B | D | D | D | D | D |
| 88 | C | D | D | D | D | D |

(Activity level: A < 0.1 μM; 0.1 μM ≤ B < 1 μM; 1 μM ≤ C < 10 μM; D ≥ 10 μM).

As shown in Table 5, the kinase selectivity profile of selected compounds of the invention was determined in kinobeads assays with mass spectrometry detection of kinases as described previously (Bantscheff et al., 2007. Nat Biotechnol. 25(9):1035-1044; WO-A 2006/134056; WO-A 2009/098021). The protein kinase complement of the human genome (the kinome) was described previously (Manning et al., 2002. Science 298(5600):1912-1934). Sequence accession numbers are defined by the International Protein Index (IPI) (Kersey et al., 2004. Proteomics 4(7):1985-1988).

TABLE 5

Inhibition values (IC50 in μM) as determined in the kinobeads assay with mass spectrometry detection of kinases (Activity levels are given in 0.1 μM ranges)

| Kinase subclass | Kinase name | IPI accession number | Example number | | | | | | |
|---|---|---|---|---|---|---|---|---|---|
| | | | 8 | 4 | 6 | 40 | 43 | 46 | 76 |
| AGC | MSK2 | IPI00022536 | n.d. | n.d. | n.d. | >10 | >10 | >10 | n.d. |
| | PDK1 | IPI00002538 | >10 | >10 | >10 | >10 | >10 | >10 | >10 |
| | PKCa | IPI00385449 | >10 | >10 | >10 | >10 | >10 | >10 | >10 |
| | PKCb | IPI00219628 | >10 | >10 | >10 | >10 | >10 | >10 | >10 |
| | PKCd | IPI00329236 | n.d. | >10 | n.d. | >10 | >10 | >10 | >10 |
| | PKCt | IPI00029196 | >10 | >10 | >10 | >10 | >10 | >10 | >10 |
| | PKN1 | IPI00412672 | >10 | >10 | >10 | >10 | >10 | >10 | >10 |
| | PKN2 | IPI00002804 | n.d. | n.d. | n.d. | >10 | >10 | n.d. | n.d. |
| | RSK2 | IPI00020898 | n.d. | >10 | n.d. | >10 | n.d. | n.d. | n.d. |
| | RSK3 | IPI00477982 | >10 | >10 | >10 | >10 | >10 | >10 | >10 |
| Atypical | ADCK1 | IPI00787836 | n.d. | n.d. | n.d. | >10 | n.d. | n.d. | n.d. |
| | ADCK3 | IPI00176469 | >10 | >10 | >10 | >10 | >10 | >10 | >10 |
| | ATM | IPI00298306 | >10 | >10 | >10 | >10 | >10 | >10 | >10 |
| | ATR | IPI00412298 | n.d. | >10 | n.d. | 1.1-1.2 | >10 | >10 | >10 |
| | BRD2 | IPI00440502 | >10 | >10 | >10 | >10 | >10 | >10 | >10 |
| | BRD3 | IPI00014266 | >10 | >10 | >10 | >10 | >10 | >10 | >10 |
| | BRD4 | IPI00440727 | >10 | >10 | >10 | >10 | >10 | >10 | >10 |
| | DNAPK | IPI00296337 | >10 | >10 | >10 | >10 | >10 | >10 | >10 |
| | mTOR | IPI00031410 | 0.1-0.2 | 0.3-0.4 | 0.1-0.2 | 0.1-0.2 | 0.1-0.2 | 0.2-0.3 | 0.1-0.2 |
| | RIOK2 | IPI00306406 | >10 | >10 | >10 | >10 | >10 | >10 | >10 |

TABLE 5-continued

Inhibition values (IC50 in μM) as determined in the kinobeads assay with mass spectrometry detection of kinases (Activity levels are given in 0.1 μM ranges)

| Kinase subclass | Kinase name | IPI accession number | Example number 8 | 4 | 6 | 40 | 43 | 46 | 76 |
|---|---|---|---|---|---|---|---|---|---|
| CAMK | AMPKa1 | IPI00410287 | >10 | >10 | >10 | >10 | >10 | >10 | >10 |
| | CaMK1d | IPI00170508 | >10 | >10 | >10 | >10 | >10 | >10 | >10 |
| | CaMK2a | IPI00550056 | >10 | n.d. | n.d. | n.d. | n.d. | n.d. | n.d. |
| | CaMK2b | IPI00221305 | >10 | n.d. | >10 | >10 | >10 | >10 | >10 |
| | CaMK2d | IPI00828081 | >10 | >10 | >10 | >10 | >10 | >10 | >10 |
| | CaMK2g | IPI00908444 | >10 | >10 | >10 | >10 | >10 | >10 | >10 |
| | CaMK4 | IPI00430411 | >10 | >10 | >10 | >10 | >10 | n.d. | n.d. |
| | DRAK2 | IPI00916930 | n.d. | >10 | n.d. | >10 | n.d. | >10 | n.d. |
| | MARK2 | IPI00555838 | >10 | >10 | >10 | >10 | >10 | >10 | >10 |
| | MARK3 | IPI00183118 | >10 | >10 | >10 | >10 | >10 | >10 | >10 |
| | MARK4 | IPI00064797 | >10 | >10 | >10 | >10 | >10 | >10 | >10 |
| | MELK | IPI00006471 | >10 | >10 | >10 | >10 | >10 | >10 | >10 |
| | PHKg2 | IPI00012891 | n.d. | >10 | n.d. | >10 | n.d. | n.d. | n.d. |
| | PKD2 | IPI00009334 | n.d. | >10 | n.d. | >10 | n.d. | n.d. | n.d. |
| | QIK | IPI00465291 | >10 | >10 | >10 | >10 | >10 | >10 | >10 |
| | QSK | IPI00657720 | >10 | >10 | >10 | >10 | >10 | >10 | >10 |
| | STK33 | IPI00302351 | n.d. | >10 | n.d. | >10 | n.d. | >10 | n.d. |
| CK1 | CK1a | IPI00448798 | >10 | >10 | >10 | >10 | >10 | >10 | >10 |
| | CK1a2 | IPI00167096 | n.d. | n.d. | n.d. | n.d. | n.d. | n.d. | n.d. |
| | CK1d | IPI00011102 | >10 | >10 | >10 | >10 | >10 | >10 | n.d. |
| | CK1e | IPI00027729 | >10 | >10 | >10 | >10 | >10 | >10 | >10 |
| | CK1g1 | IPI00791893 | >10 | >10 | >10 | >10 | >10 | >10 | >10 |
| | CK1g2 | IPI00297767 | n.d. | n.d. | n.d. | n.d. | n.d. | >10 | n.d. |
| | CK1g3 | IPI00218437 | >10 | >10 | n.d. | n.d. | n.d. | n.d. | n.d. |
| CMGC | CDC2 | IPI00026689 | n.d. | >10 | n.d. | >10 | n.d. | >10 | >10 |
| | CDK2 | IPI00031681 | >10 | >10 | >10 | >10 | >10 | >10 | >10 |
| | CDK5 | IPI00023530 | >10 | >10 | >10 | >10 | >10 | >10 | >10 |
| | CDK6 | IPI00023529 | n.d. | >10 | >10 | >10 | >10 | >10 | >10 |
| | CDK7 | IPI00000685 | >10 | >10 | >10 | >10 | >10 | >10 | >10 |
| | CDK9 | IPI00552413 | >10 | >10 | >10 | >10 | >10 | >10 | >10 |
| | CDK10 | IPI00014873 | n.d. | >10 | n.d. | >10 | >10 | n.d. | n.d. |
| | CLK1 | IPI00915761 | >10 | n.d. | n.d. | >10 | >10 | >10 | n.d. |
| | CLK2 | IPI00028071 | >10 | n.d. | n.d. | >10 | >10 | >10 | n.d. |
| | DYRK1A | IPI00014344 | n.d. | >10 | n.d. | n.d. | n.d. | n.d. | n.d. |
| | Erk1 | IPI00018195 | >10 | >10 | >10 | >10 | >10 | >10 | >10 |
| | Erk2 | IPI00003479 | >10 | >10 | >10 | >10 | >10 | >10 | >10 |
| | Erk5 | IPI00910923 | n.d. | >10 | n.d. | n.d. | n.d. | n.d. | n.d. |
| | GSK3A | IPI00292228 | >10 | >10 | >10 | >10 | >10 | >10 | >10 |
| | GSK3B | IPI00216190 | >10 | >10 | >10 | >10 | >10 | >10 | >10 |
| | JNK1 | IPI00220306 | >10 | >10 | >10 | >10 | >10 | >10 | >10 |
| | JNK2 | IPI00303550 | >10 | >10 | >10 | >10 | >10 | >10 | >10 |
| | NLK | IPI00008237 | >10 | >10 | >10 | >10 | >10 | >10 | >10 |
| | p38a | IPI00221141 | >10 | >10 | >10 | >10 | >10 | >10 | >10 |
| | p38b | IPI00019473 | n.d. | >10 | >10 | n.d. | >10 | n.d. | n.d. |
| Lipid Kinase | PIK3C3 | IPI00873758 | n.d. | >10 | n.d. | >10 | >10 | >10 | >10 |
| | PIK3Ca | IPI00031386 | >10 | >10 | >10 | >10 | >10 | >10 | >10 |
| | PIK3Cb | IPI00031388 | >10 | >10 | >10 | >10 | >10 | >10 | >10 |
| | PIK3Cd | IPI00384817 | >10 | >10 | >10 | >10 | >10 | >10 | >10 |
| | PIK3Cg | IPI00292690 | >10 | >10 | >10 | >10 | >10 | >10 | >10 |
| | PIK4C2B | IPI00291068 | >10 | >10 | >10 | >10 | >10 | >10 | >10 |
| | PIK4Ca | IPI00070943 | >10 | >10 | >10 | >10 | >10 | >10 | >10 |
| | PIK4Cb | IPI00641770 | >10 | >10 | >10 | >10 | >10 | >10 | >10 |
| | PIP5K2A | IPI00009688 | n.d. | n.d. | n.d. | >10 | n.d. | n.d. | n.d. |
| | PIP5K2C | IPI00152303 | n.d. | n.d. | n.d. | >10 | >10 | >10 | >10 |
| Other | AAK1 | IPI00916402 | >10 | >10 | >10 | >10 | >10 | >10 | >10 |
| | AurA | IPI00298940 | >10 | >10 | >10 | >10 | >10 | >10 | >10 |
| | AurB | IPI00796914 | >10 | >10 | >10 | >10 | >10 | >10 | >10 |
| | BIKE | IPI00337426 | >10 | >10 | >10 | >10 | >10 | >10 | >10 |
| | CaMKK1 | IPI00792960 | n.d. | >10 | n.d. | >10 | >10 | >10 | >10 |
| | CaMKK2 | IPI00290239 | >10 | >10 | >10 | >10 | >10 | >10 | >10 |
| | CK2a1 | IPI00016613 | >10 | >10 | >10 | >10 | >10 | >10 | >10 |
| | CK2a2 | IPI00020602 | >10 | >10 | >10 | >10 | >10 | >10 | >10 |
| | GAK | IPI00298949 | n.d. | >10 | n.d. | >10 | >10 | >10 | >10 |
| | GCN2 | IPI00163851 | >10 | >10 | >10 | n.d. | >10 | >10 | n.d. |
| | HRI | IPI00328149 | >10 | >10 | n.d. | >10 | >10 | >10 | >10 |
| | IKKe | IPI00029045 | >10 | >10 | >10 | >10 | >10 | >10 | >10 |
| | MPSK1 | IPI00915837 | n.d. | >10 | >10 | n.d. | n.d. | n.d. | >10 |
| | MYT1 | IPI00909627 | >10 | >10 | >10 | >10 | >10 | >10 | >10 |
| | NEK2 | IPI00021331 | >10 | >10 | >10 | >10 | >10 | >10 | >10 |
| | NEK9 | IPI00301609 | >10 | >10 | >10 | >10 | >10 | >10 | >10 |
| | PIK3R4 | IPI00024006 | n.d. | >10 | >10 | >10 | >10 | >10 | >10 |
| | PLK4 | IPI00410344 | >10 | >10 | >10 | >10 | >10 | >10 | >10 |
| | SgK223 | IPI00739386 | >10 | n.d. | >10 | >10 | >10 | >10 | >10 |

TABLE 5-continued

Inhibition values (IC50 in μM) as determined in the kinobeads assay with mass spectrometry detection of kinases (Activity levels are given in 0.1 μM ranges)

| Kinase subclass | Kinase name | IPI accession number | 8 | 4 | 6 | 40 | 43 | 46 | 76 |
|---|---|---|---|---|---|---|---|---|---|
| | TBK1 | IPI00293613 | >10 | >10 | >10 | >10 | >10 | >10 | >10 |
| | ULK3 | IPI00910978 | >10 | >10 | >10 | >10 | >10 | >10 | >10 |
| | Wee1 | IPI00025830 | >10 | >10 | >10 | >10 | >10 | >10 | >10 |
| STE | GCK | IPI00149094 | >10 | >10 | >10 | >10 | >10 | >10 | >10 |
| | HPK1 | IPI00020258 | >10 | >10 | >10 | >10 | >10 | >10 | >10 |
| | KHS1 | IPI00294842 | >10 | >10 | >10 | >10 | >10 | >10 | >10 |
| | MAP2K1 | IPI00219604 | n.d. | >10 | n.d. | >10 | >10 | >10 | >10 |
| | MAP2K2 | IPI00003783 | n.d. | >10 | n.d. | >10 | >10 | >10 | >10 |
| | MAP2K5 | IPI00158248 | >10 | >10 | >10 | >10 | >10 | >10 | >10 |
| | MAP3K1 | IPI00855985 | >10 | >10 | >10 | >10 | >10 | >10 | >10 |
| | MAP3K2 | IPI00513803 | >10 | >10 | >10 | >10 | >10 | >10 | >10 |
| | MAP3K3 | IPI00181703 | n.d. | n.d. | n.d. | >10 | n.d. | n.d. | >10 |
| | MAP3K4 | IPI00386260 | >10 | >10 | >10 | >10 | >10 | >10 | >10 |
| | MAP3K5 | IPI00412433 | n.d. | >10 | n.d. | >10 | n.d. | n.d. | >10 |
| | MST1 | IPI00011488 | >10 | >10 | >10 | >10 | >10 | >10 | >10 |
| | MST2 | IPI00411984 | n.d. | n.d. | n.d. | >10 | >10 | >10 | n.d. |
| | PAK4 | IPI00014068 | >10 | >10 | >10 | >10 | >10 | >10 | >10 |
| | SLK | IPI00022827 | n.d. | >10 | n.d. | n.d. | n.d. | n.d. | n.d. |
| | TAO2 | IPI00006283 | >10 | >10 | >10 | >10 | >10 | >10 | >10 |
| | TAO3 | IPI00410485 | >10 | >10 | >10 | >10 | >10 | >10 | >10 |
| TK | ABL | IPI00221171 | n.d. | >10 | n.d. | >10 | n.d. | n.d. | >10 |
| | ACK | IPI00552750 | >10 | >10 | >10 | >10 | >10 | >10 | >10 |
| | ARG | IPI00329488 | >10 | >10 | >10 | >10 | >10 | >10 | >10 |
| | BLK | IPI00554756 | >10 | >10 | >10 | >10 | >10 | >10 | >10 |
| | BTK | IPI00029132 | >10 | >10 | >10 | >10 | >10 | >10 | >10 |
| | CSK | IPI00013212 | >10 | >10 | >10 | >10 | >10 | >10 | >10 |
| | DDR1 | IPI00657861 | n.d. | >10 | >10 | >10 | >10 | >10 | >10 |
| | EphA3 | IPI00298105 | >10 | >10 | n.d. | >10 | >10 | >10 | n.d. |
| | EphB2 | IPI00021275 | >10 | >10 | >10 | >10 | >10 | >10 | >10 |
| | EphB6 | IPI00005222 | n.d. | >10 | >10 | >10 | n.d. | >10 | n.d. |
| | FAK | IPI00413961 | >10 | >10 | >10 | >10 | >10 | >10 | >10 |
| | FER | IPI00029263 | >10 | >10 | >10 | >10 | >10 | >10 | >10 |
| | FGR | IPI00016871 | >10 | >10 | >10 | >10 | >10 | >10 | >10 |
| | FYN | IPI00219012 | >10 | >10 | >10 | >10 | >10 | >10 | >10 |
| | INSR | IPI00025803 | n.d. | >10 | n.d. | >10 | n.d. | n.d. | n.d. |
| | ITK | IPI00004566 | >10 | >10 | >10 | >10 | >10 | >10 | >10 |
| | JAK1 | IPI00784013 | >10 | >10 | >10 | >10 | >10 | >10 | >10 |
| | JAK2 | IPI00031016 | n.d. | n.d. | n.d. | >10 | n.d. | >10 | n.d. |
| | JAK3 | IPI00219418 | n.d. | n.d. | >10 | >10 | >10 | >10 | >10 |
| | KIT | IPI00022296 | n.d. | n.d. | n.d. | >10 | >10 | >10 | n.d. |
| | LCK | IPI00515097 | n.d. | >10 | >10 | >10 | >10 | >10 | >10 |
| | LYN | IPI00298625 | >10 | >10 | >10 | >10 | >10 | >10 | >10 |
| | PYK2 | IPI00029702 | >10 | >10 | >10 | >10 | >10 | >10 | >10 |
| | SRC | IPI00328867 | >10 | >10 | >10 | >10 | >10 | >10 | >10 |
| | SYK | IPI00018597 | >10 | >10 | >10 | >10 | >10 | >10 | >10 |
| | TEC | IPI00000878 | >10 | >10 | >10 | >10 | >10 | >10 | >10 |
| | TYK2 | IPI00022353 | >10 | >10 | >10 | >10 | >10 | >10 | >10 |
| | YES | IPI00013981 | >10 | >10 | >10 | >10 | >10 | >10 | >10 |
| | ZAP70 | IPI00329789 | n.d. | >10 | n.d. | >10 | >10 | >10 | n.d. |
| TKL | ACTR2B | IPI00437565 | >10 | >10 | >10 | >10 | >10 | >10 | >10 |
| | ALK2 | IPI00029219 | >10 | >10 | >10 | >10 | >10 | >10 | >10 |
| | ALK4 | IPI00005732 | >10 | >10 | >10 | >10 | n.d. | >10 | >10 |
| | ARAF | IPI00020578 | >10 | >10 | >10 | >10 | >10 | >10 | >10 |
| | BMPR1A | IPI00005731 | >10 | n.d. | >10 | n.d. | >10 | n.d. | >10 |
| | BMPR2 | IPI00783156 | n.d. | n.d. | n.d. | >10 | n.d. | n.d. | n.d. |
| | BRAF | IPI00303797 | >10 | >10 | >10 | >10 | >10 | >10 | >10 |
| | ILK | IPI00013219 | >10 | >10 | n.d. | >10 | >10 | n.d. | >10 |
| | IRAK1 | IPI00293652 | n.d. | >10 | n.d. | >10 | >10 | >10 | >10 |
| | LIMK1 | IPI00291702 | >10 | >10 | >10 | >10 | >10 | >10 | >10 |
| | LIMK2 | IPI00025698 | >10 | >10 | >10 | >10 | >10 | >10 | >10 |
| | MLK3 | IPI00000977 | >10 | >10 | >10 | >10 | >10 | n.d. | n.d. |
| | RIPK2 | IPI00021917 | >10 | >10 | >10 | >10 | >10 | >10 | >10 |
| | RIPK3 | IPI00847572 | >10 | >10 | >10 | >10 | >10 | >10 | >10 |
| | TESK1 | IPI00018182 | >10 | >10 | >10 | >10 | >10 | >10 | n.d. |
| | TESK2 | IPI00102677 | >10 | >10 | >10 | >10 | >10 | >10 | >10 |
| | TGFbR1 | IPI00005733 | >10 | >10 | >10 | >10 | >10 | >10 | >10 |
| | TGFbR2 | IPI00164934 | n.d. | >10 | >10 | >10 | n.d. | >10 | >10 |
| | ZAK | IPI00329638 | >10 | >10 | >10 | >10 | >10 | >10 | >10 |

In Vitro Phospho-S6 and Phospho-Akt Cellular Assay

Activation of mTOR signaling results in phosphorylation of several downstream targets. In cells, mTOR exists in two different protein complexes. The mTOR Complex-1 (mTORC1) phosphorylates and activates S6 Kinase 1 (S6K1) and S6 Kinase 2 (S6K2) (also known as p70S6K) which then phosphorylate S6 Ribosomal Protein (S6RP) (also known as RPS6). S6RP is phosphorylated on serine 235, serine 236, serine 240 and serine 244 by both pS6K1 and pS6K2. The mTOR Complex-2 (mTORC2) phosphorylates AKT on serine 473 which activates the AKT signaling pathway.

The assay measures a test compound's inhibition of S6RP serine-240/244 phosphorylation and inhibition of Akt serine-473 phosphorylation in human embryonic kidney derived HEK293T/17 cells (ATCC CRL-11268).

The HEK293T/17 cell line is maintained in DMEM media (Invitrogen catalogue number 41965-039) supplemented with 10% FCS at 37° C. in a 5% CO2 humidified incubator.

Cells are seeded in 96-well plates at 40,000 cells/well (pS6RP S240/244 assay) or 80,000 cells/well (pAkt S473 assay) in 90 µl growth media (DMEM, 2% FCS). Plates are incubated for 1 hour in a humidified incubator to allow the cells to adhere. Cells are treated with 8 concentrations of test compounds or DMSO alone for controls (final DMSO concentration 0.1%) and incubated at 37° C. for 2 hours. Then 20 µl of 5× concentrated lysis buffer (750 mM NaCl, 100 mM Tris pH7.4, 5 mM EDTA, 5 mM EGTA, 5% Triton X-100) is added, plates are sealed and incubated for 15 minutes at 4° C. with gentle shaking. After cell lysis, 25 µl cell lysate is transferred to a MesoScale plate coated with an antibody to pS6RP Ser240/244 (MesoScale Discovery K150DGD-3) or an antibody to pAkt Ser 473 (MesoScale Discovery K151DGD-3). Plates have been blocked before by incubation with 150 µl MesoScale Discovery Blocking Solution-A for 1 hour at room temperature followed by washing with 150 µl 1× Tris wash buffer per well. After the transfer of the cell lysate to the MSD plate, the pS6RP (or pAkt) protein is captured on the coated antibody by incubation at room temperature for 1 hour with gentle shaking. After the capture step the plate is washed three times with 150 µl of 1× Tris wash buffer per well. Then 25 µl detection antibody conjugated with a Sulfo-Tag is added and incubated for 1 hour at room temperature with gentle shaking. Subsequently the antibody solution is removed and the plate is washed 3 times with 150 µl 1× Tris wash buffer per well and 150 µl Read buffer is added. The plates are analysed on a MSD 2400 Plate Reader (MesoScale Discovery). Data analysis is performed using nonlinear regression for a sigmoidal dose-response with a variable slope.

TABLE 6

Phospho-Akt and phospho-S6 cell assay data
(Activity level: A < 0.1 µM; 0.1 µM ≤ B < 1 µM; 1µM ≤ C < 10 µM; D ≥ 10 µM).

| Example Number. | pAKT | pS6 |
| --- | --- | --- |
| 2 | A | A |
| 3 | — | A |
| 4 | — | A |
| 6 | A | A |
| 7 | — | B |
| 14 | — | B |
| 15 | — | B |
| 21 | B | A |
| 22 | — | B |
| 23 | A | B |
| 24 | — | B |
| 25 | — | B |
| 26 | — | B |
| 28 | — | C |
| 29 | — | B |
| 30 | — | C |
| 34 | — | B |
| 35 | — | B |
| 37 | — | B |
| 38 | — | B |
| 39 | — | B |
| 40 | A | A |
| 41 | A | A |
| 42 | A | B |
| 43 | A | A |
| 44 | A | A |
| 45 | | B |
| 46 | A | A |
| 47 | A | A |
| 48 | | B |
| 49 | | B |
| 50 | | B |
| 51 | | B |
| 52 | | B |
| 53 | | B |
| 54 | | B |
| 55 | | B |
| 56 | | B |
| 57 | | B |
| 58 | | B |
| 59 | | B |
| 60 | A | A |
| 61 | A | A |
| 62 | A | B |
| 63 | | B |
| 64 | A | A |
| 65 | — | B |
| 66 | — | B |
| 67 | — | B |
| 68 | — | B |
| 69 | — | A |
| 70 | — | B |
| 71 | — | A |
| 72 | — | B |
| 73 | — | A |
| 74 | A | A |
| 75 | — | B |
| 76 | A | A |
| 77 | A | A |
| 78 | A | A |
| 79 | — | B |
| 80 | — | A |
| 81 | — | A |
| 82 | — | A |
| 83 | — | A |
| 84 | — | C |
| 86 | — | B |
| 87 | — | A |
| 88 | — | A |

The invention claimed is:
1. A compound of formula (I)

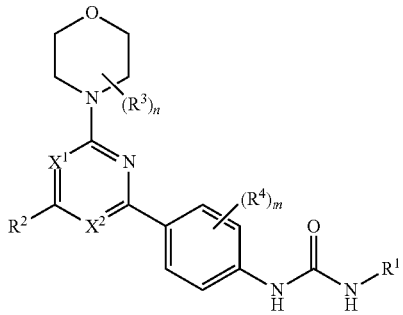

or a pharmaceutically acceptable salt thereof, wherein
$R^1$ is H; $T^1$; or $C_{1-6}$ alkyl; wherein $C_{1-6}$ alkyl is optionally substituted with one or more $R^5$, which are the same or different;
$R^5$ is halogen; CN; $OR^6$; $C(O)N(R^6R^{6a})$; $N(R^{6a})C(O)R^6$; or $N(R^6R^{6a})$;
$T^1$ is phenyl; 4 to 7 membered heterocyclyl; or $C_{3-7}$ cycloalkyl, wherein $T^1$ is optionally substituted with one or more $R^{5a}$, which are the same or different;
$R^{5a}$ is halogen; CN; $OR^6$; $N(R^6R^{6a})$; or $C_{1-6}$ alkyl, wherein $C_{1-6}$ alkyl is optionally substituted with one or more $R^{5b}$, which are the same or different;
$R^{5b}$ is halogen; or $OR^6$;
$R^6$, $R^{6a}$ are independently selected from the group consisting of H; and $C_{1-6}$ alkyl, wherein $C_{1-6}$ alkyl is optionally substituted with one or more halogen, which are the same or different;
$R^2$ is $T^2$;
$T^2$ is phenyl or 5 to 6 membered aromatic heterocyclyl, wherein $T^2$ is substituted with 1 or 2 $R^7$, and wherein at least one $R^7$ is $S(O)R^8$;
$R^7$ is halogen; CN; $OR^8$; $CO(O)R^8$; $C(O)N(R^8R^{8a})$; $S(O)_2N(R^8R^{8a})$; $S(O)N(R^8R^{8a})$; $S(O)_2R^8$; $S(O)R^8$; $N(R^8R^{8a})$; $N(R^8)C(O)R^{8a}$; $N(R^8)S(O)_2R^{8a}$; $N(R^8)S(O)R^{8a}$; $N(R^8)C(O)N(R^{8a}R^{8b})$; $N(R^8)C(O)OR^{8a}$; $OC(O)N(R^8R^{8a})$; or $C_{1-6}$ alkyl; wherein $C_{1-6}$ alkyl is optionally substituted with one or more $R^9$, which are the same or different;
$R^8$, $R^{8a}$, $R^{8b}$ are independently selected from the group consisting of H; $C_{1-6}$ alkyl; and 5 to 6 membered heterocyclyl, wherein $C_{1-6}$ alkyl is optionally substituted with one or more $R^9$, which are the same or different and wherein 5 to 6 membered heterocyclyl is optionally substituted with one or more $R^{9a}$, which are the same or different;
$R^9$ is halogen; CN; $OR^{10}$; $C(O)OR^{10}$; $C(O)R^{10}$; $C(O)N(R^{10}R^{10a})$; $S(O)_2N(R^{10}R^{10a})$; $S(O)N(R^{10}R^{10a})$; $S(O)_2R^{10}$; $N(R^{10}R^{10a})$; $OC(O)R^{10}$; $N(R^{10})C(O)R^{10a}$; $N(R^{10})S(O)_2R^{10a}$; $N(R^{10})S(O)R^{10a}$; $N(R^{10})C(O)N(R^{10a}R^{10b})$; $N(R^{10})C(O)OR^{10a}$; $OC(O)N(R^{10}R^{10a})$; or 5 to 6 membered heterocyclyl, wherein 5 to 6 membered heterocyclyl is optionally substituted with one or more $R^{11}$, which are the same or different;
$R^{9a}$ is halogen; CN; $C(O)OR^{10}$; $OR^{10}$; oxo (=O), where the ring is at least partially saturated; $C(O)R^{10}$; $C(O)N(R^{10}R^{10a})$; $S(O)_2N(R^{10}R^{10a})$; $S(O)N(R^{10}R^{10a})$; $S(O)_2R^{10}$; $N(R^{10}R^{10a})$; $OC(O)R^{10}$; $N(R^{10})C(O)R^{10a}$; $N(R^{10})S(O)_2R^{10a}$; $N(R^{10})S(O)R^{10a}$; $N(R^{10})C(O)N(R^{10a}R^{10b})$; $N(R^{10})C(O)OR^{10a}$; $OC(O)N(R^{10}R^{10a})$; or $C_{1-6}$ alkyl, wherein $C_{1-6}$ alkyl is optionally substituted with one or more $R^{11a}$, which are the same or different;
$R^{10}$, $R^{10a}$, $R^{10b}$ are independently selected from the group consisting of H; and $C_{1-6}$ alkyl, wherein $C_{1-6}$ alkyl is optionally substituted with one or more halogen, which are the same or different;
$R^{11}$, $R^{11a}$ are independently selected from the group consisting of halogen; and $C_{1-6}$ alkyl, wherein $C_{1-6}$ alkyl is optionally substituted with one or more halogen, which are the same or different;
Each $R^3$ is independently $C_{1-6}$ alkyl, wherein $R^3$ is optionally substituted with one or more halogen, which are the same or different;
Optionally two $R^3$ are joined together with the atoms to which they are attached to form a ring $T^3$;
$T^3$ is $C_{3-7}$ cycloalkyl; 4 to 7 membered heterocyclyl; or phenyl, wherein $T^3$ is optionally substituted with one or more $C_{1-6}$ alkyl, which are the same or different and optionally substituted with one or more halogen, which are the same or different;
Each $R^4$ is independently halogen;
m is 0, 1 or 2;
n is 0, 1 or 2;
One of $X^1$, $X^2$ is $C(R^{12})$ and the other is N;
$R^{12}$ is H; halogen; CN; or $C_{1-6}$ alkyl, wherein $C_{1-6}$ alkyl is optionally substituted with one or more halogen, which are the same or different.

2. A compound of claim 1, wherein $R^1$ is H; or $C_{1-6}$ alkyl, wherein $C_{1-6}$ alkyl is optionally substituted with one or more $R^5$, which are the same or different; or $C_{3-7}$ cycloalkyl, wherein $C_{3-7}$ cycloalkyl is optionally substituted with one or more $R^{5a}$, which are the same or different.

3. A compound of claim 1, wherein $R^5$ is halogen; CN; $OR^6$; $C(O)N(R^6R^{6a})$; or $N(R^6R^{6a})$.

4. A compound of claim 1, wherein $R^5$ is halogen; CN; $OR^6$; or $N(R^6R^{6a})$.

5. A compound of claim 1, wherein $R^{5a}$ is halogen; CN; $OR^6$; $N(R^6R^{6a})$; or $C_{1-6}$ alkyl, wherein $C_{1-6}$ alkyl is optionally substituted with one or more halogen, which are the same or different.

6. A compound of claim 1, wherein $R^3$ is methyl.

7. A compound of claim 1, wherein n is 0; n is 1 and $R^3$ is methyl; or n is 2 and the two $R^3$ are joined together with the morpholine ring to form an 8-oxa-3-azabicyclo[3.2.1]octan-3-yl ring.

8. A compound of claim 1, wherein $R^4$ is F.

9. A compound of claim 1, wherein m, n are independently selected from the group consisting of 0 and 1.

10. A compound of claim 1, wherein $X^1$ is N.

11. A compound of claim 1, wherein $R^{12}$ is H.

12. A compound of claim 1 selected from the group consisting of
(S)-1-ethyl-3-(4-(6-(5-fluoro-2-(methylsulfonyl)phenyl)-2-(3-methylmorpholino)pyrimidin-4-yl)phenyl)urea;
(S)-1-cyclopropyl-3-(4-(2-(3-methylmorpholino)-6-(2-(methylsulfonyl)phenyl)pyrimidin-4-yl)phenyl)urea;
(S)-1-cyclopropyl-3-(4-(6-(3-methylmorpholino)-2-(3-(methylsulfonyl)phenyl)pyrimidin-4-yl)phenyl)urea;
(S)-1-cyclopropyl-3-(4-(4-(3-methylmorpholino)-6-(2-(methylsulfonyl)phenyl)pyrimidin-2-yl)phenyl)urea;
(S)-1-ethyl-3-(4-(2-(3-methylmorpholino)-6-(5-(methylsulfonyl)pyridin-3-yl)pyrimidin-4-yl)phenyl)urea;
1-ethyl-3-(4-(6-(2-(methylsulfonyl)phenyl)-2-morpholinopyrimidin-4-yl)phenyl)urea;
(S)-1-cyclopropyl-3-(4-(6-(3-methylmorpholino)-2-(5-(methylsulfonyl)pyridin-3-yl)pyrimidin-4-yl)phenyl)urea;

(S)-1-cyclopropyl-3-(4-(6-(5-fluoro-2-(methylsulfonyl)phenyl)-2-(3-methylmorpholino)pyrimidin-4-yl)phenyl)urea;

(S)-1-(4-(6-(5-fluoro-2-(methylsulfonyl)phenyl)-2-(3-methylmorpholino)pyrimidin-4-yl)phenyl)-3-(2-hydroxyethyl)urea;

(S)-1-(4-(6-(5-fluoro-2-(methylsulfonyl)phenyl)-2-(3-methylmorpholino)pyrimidin-4-yl)phenyl)-3-(2-fluoroethyl)urea;

(S)-1-cyclopropyl-3-(4-(2-(3-methylmorpholino)-6-(2-(methylsulfonyl)pyridin-3-yl)pyrimidin-4-yl)phenyl)urea;

(S)-1-(2,2-difluoroethyl)-3-(4-(6-(5-fluoro-2-(methylsulfonyl)phenyl)-2-(3-methylmorpholino)pyrimidin-4-yl)phenyl)urea;

1-(4-(6-(5-fluoro-2-(methylsulfonyl)phenyl)-2-morpholinopyrimidin-4-yl)phenyl)-3-(2-hydroxyethyl)urea;

(S)-1-(4-(6-(5-fluoro-2-(methylsulfonyl)phenyl)-2-(3-methylmorpholino)pyrimidin-4-yl)phenyl)-3-(3-hydroxypropyl)urea;

(S)-1-cyclopropyl-3-(3-fluoro-4-(4-(5-fluoro-2-(methylsulfonyl)phenyl)-6-(3-methylmorpholino)pyrimidin-2-yl)phenyl)urea;

(S)-1-(3-fluoro-4-(4-(5-fluoro-2-(methylsulfonyl)phenyl)-6-(3-methylmorpholino)pyrimidin-2-yl)phenyl)-3-(2-fluoroethyl)urea;

(S)-1-(4-(6-(5-fluoro-2-(methylsulfonyl)phenyl)-2-(3-methylmorpholino)pyrimidin-4-yl)phenyl)-3-(1-hydroxy-2-methylpropan-2-yl)urea;

(S)-2-(3-(4-(6-(5-fluoro-2-(methylsulfonyl)phenyl)-2-(3-methylmorpholino)pyrimidin-4-yl)phenyl)ureido)acetamide;

1-(4-(6-(5-fluoro-2-(methylsulfonyl)phenyl)-2-((S)-3-methylmorpholino)pyrimidin-4-yl)phenyl)-3-(2-hydroxypropyl)urea;

(S)-1-(3-fluoro-4-(4-(5-fluoro-2-(methylsulfonyl)phenyl)-6-(3-methylmorpholino)pyrimidin-2-yl)phenyl)-3-(2-hydroxyethyl)urea;

1-(4-(6-(5-fluoro-2-(methylsulfonyl)phenyl)-2-((S)-3-methylmorpholino)pyrimidin-4-yl)phenyl)-3-((R)-1-hydroxypropan-2-yl)urea;

1-(4-(6-(5-fluoro-2-(methylsulfonyl)phenyl)-2-((S)-3-methylmorpholino)pyrimidin-4-yl)phenyl)-3-((S)-1-hydroxypropan-2-yl)urea;

(S)-1-(4-(6-(5-fluoro-2-(methylsulfonyl)phenyl)-2-(3-methylmorpholino)pyrimidin-4-yl)phenyl)-3-(1-(hydroxymethyl)cyclobutyl)urea;

1-(4-(6-(5-fluoro-2-(methylsulfonyl)phenyl)-2-((S)-3-methylmorpholino)pyrimidin-4-yl)phenyl)-3-((1S,2S)-2-hydroxycyclopentyl)urea;

(S)-1-cyclopropyl-3-(4-(4-(5-fluoro-2-(methylsulfonyl)phenyl)-6-(3-methylmorpholino)pyrimidin-2-yl)phenyl)urea;

(S)-1-(4-(4-(5-fluoro-2-(methylsulfonyl)phenyl)-6-(3-methylmorpholino)pyrimidin-2-yl)phenyl)-3-(2-hydroxyethyl)urea;

(S)-1-(4-(6-(5-fluoro-2-(methylsulfonyl)phenyl)-2-(3-methylmorpholino)pyrimidin-4-yl)phenyl)-3-(3-methoxycyclobutyl)urea;

(S)-1-(2-hydroxyethyl)-3-(4-(4-(3-methylmorpholino)-6-(2-(methylsulfonyl)phenyl)pyrimidin-2-yl)phenyl)urea;

1-(4-(2-(8-oxa-3-azabicyclo[3.2.1]octan-3-yl)-6-(5-fluoro-2-(methylsulfonyl)phenyl)pyrimidin-4-yl)phenyl)-3-cyclopropylurea;

1-(4-(6-(5-fluoro-2-(methylsulfonyl)phenyl)-2-((S)-3-methylmorpholino)pyrimidin-4-yl)phenyl)-3-((R)-2-hydroxypropyl)urea;

1-(4-(6-(5-fluoro-2-(methylsulfonyl)phenyl)-2-((S)-3-methylmorpholino)pyrimidin-4-yl)phenyl)-3-((S)-2-hydroxypropyl)urea;

(S)-1-(2-aminoethyl)-3-(4-(6-(5-fluoro-2-(methylsulfonyl)phenyl)-2-(3-methylmorpholino)pyrimidin-4-yl)phenyl)urea;

(S)—N-(2-(3-(4-(6-(5-fluoro-2-(methylsulfonyl)phenyl)-2-(3-methylmorpholino)pyrimidin-4-yl)phenyl)ureido)ethyl)acetamide;

(S)-1-(4-(6-(5-fluoro-2-(methylsulfonyl)phenyl)-2-(3-methylmorpholino)pyrimidin-4-yl)phenyl)-3-(oxetan-3-yl)urea;

(S)-1-cyclopropyl-3-(4-(6-(2-(ethylsulfonyl)phenyl)-2-(3-methylmorpholino)pyrimidin-4-yl)phenyl)urea; and (S)-1-cyclopropyl-3-(4-(2-(3-methylmorpholino)-6-(2-(pyrrolidin-1-ylsulfonyl)phenyl)pyrimidin-4-yl)phenyl)urea.

13. A pharmaceutical composition comprising a compound or a pharmaceutically acceptable salt thereof of claim 1 together with a pharmaceutically acceptable carrier, optionally in combination with one or more other pharmaceutical compositions.

14. A method for treating in a mammalian patient in need thereof one or more conditions selected from the group consisting of diseases and disorders associated with mTOR, the method comprising the administration to said patient a therapeutically effective amount of a compound of claim 1 or a pharmaceutically acceptable salt thereof.

15. A method for the preparation of a compound of claim 1, comprising the steps of (a)
reacting a compound of formula (II)

(II)

wherein $R^3$, n, $X^1$, $X^2$ have the meaning as indicated in claim 1 and R2' is Cl with a compound of formula (III)

(III)

wherein $R^1$, $R^4$, m have the meaning as indicated in claim 1 and X is a boronic acid or ester in a Suzuki reaction to yield a compound of formula (I), or (a')
reacting the compound of formula (II) in two Suzuki reactions with a compound of
formula $R^2$—X, wherein X is a boronic acid or boronic ester, and subsequently with a compound of formula (III) to yield a compound of formula (I).

16. The method of claim 14 wherein the one or more conditions is selected from the group consisting of an immunological, inflammatory, autoimmune, or allergic disorder or disease or a transplant rejection or a Graft-versus host disease.

17. The method of claim 14 wherein the one or more condition is a proliferative disease.

18. The method of claim 17, wherein the disease is cancer.

19. The method of claim 14 wherein the one or more conditions is selected from the group consisting of a cardiovascular disease, a metabolic disease or a neurodegenerative disease.

20. The method of claim 14 wherein the one or more conditions is an autophagy associated disease.

21. The method of claim 14 wherein the one or more conditions is a viral infection.

* * * * *